United States Patent
Boesen

(10) Patent No.: US 11,141,455 B2
(45) Date of Patent: Oct. 12, 2021

(54) PEPTIDE ANALOGUES WITH BRANCHED AMINO ACID PROBE(S)

(71) Applicant: TXP Pharma GmbH, Baar (CH)

(72) Inventor: Thomas Boesen, Copenhagen (DK)

(73) Assignee: TXP Pharma GmbH, Baar (CH)

( * ) Notice: Subject to any disclaimer, the term of this patent is extended or adjusted under 35 U.S.C. 154(b) by 0 days.

(21) Appl. No.: 15/917,223

(22) Filed: Mar. 9, 2018

(65) Prior Publication Data

US 2019/0030115 A1 Jan. 31, 2019

Related U.S. Application Data

(62) Division of application No. 14/693,810, filed on Apr. 22, 2015, now Pat. No. 9,950,027.

(60) Provisional application No. 61/982,709, filed on Apr. 22, 2014.

(51) Int. Cl.
| | |
|---|---|
| *A61K 38/10* | (2006.01) |
| *C07K 14/605* | (2006.01) |
| *A61K 38/07* | (2006.01) |
| *A61K 38/05* | (2006.01) |
| *A61K 38/06* | (2006.01) |
| *A61K 38/095* | (2019.01) |
| *A61K 38/00* | (2006.01) |

(52) U.S. Cl.
CPC .............. *A61K 38/10* (2013.01); *A61K 38/05* (2013.01); *A61K 38/06* (2013.01); *A61K 38/07* (2013.01); *A61K 38/095* (2019.01); *C07K 14/605* (2013.01); *A61K 38/00* (2013.01)

(58) Field of Classification Search
CPC ........................... A61K 38/2278; A61K 38/26
See application file for complete search history.

(56) References Cited

U.S. PATENT DOCUMENTS

| | | | |
|---|---|---|---|
| 4,166,452 A | 9/1979 | Generales | |
| 4,265,874 A | 5/1981 | Bonsen et al. | |
| 4,356,108 A | 10/1982 | Schwab et al. | |
| 7,169,603 B2 | 1/2007 | Hedley et al. | |
| 9,217,023 B2 * | 12/2015 | Boesen | C07K 14/685 |
| 9,486,495 B2 | 11/2016 | Boesen | |
| 9,950,027 B2 * | 4/2018 | Boesen | A61P 19/06 |
| 9,951,116 B2 * | 4/2018 | Boesen | C07K 14/685 |
| 2007/0041951 A1 * | 2/2007 | Egan | A61P 3/10 424/93.7 |
| 2011/0071088 A1 | 3/2011 | Benowitz | |
| 2014/0155328 A1 | 6/2014 | Boesen | |
| 2015/0297671 A1 | 10/2015 | Boesen | |
| 2015/0297672 A1 | 10/2015 | Boesen | |
| 2015/0376254 A1 | 12/2015 | Boesen | |
| 2016/0074469 A1 | 3/2016 | Boesen | |
| 2017/0174738 A1 | 6/2017 | Boesen | |

FOREIGN PATENT DOCUMENTS

| | | |
|---|---|---|
| JP | 2009-505994 A | 2/2009 |
| WO | WO 1996/039161 A1 | 12/1996 |
| WO | WO 1998/027113 A1 | 6/1998 |
| WO | WO 1999/046283 A1 | 9/1999 |
| WO | WO 1999/057148 A1 | 11/1999 |
| WO | WO 2007/008704 A2 | 1/2007 |
| WO | WO 2007/022774 A1 | 3/2007 |
| WO | WO 2014/060606 A1 | 4/2014 |
| WO | WO 2015/162485 A1 | 10/2015 |

OTHER PUBLICATIONS

Gómara et al., "Assessment of synthetic chimeric multichain antigenic peptides for diagnosis of GB virus C infection", Analytical Biochemistry, 2010, pp. 51-58 (Year: 2010).*
Bon et al., "Peptide-Derivatized SB105-A10 Dendrimer Inhibits the Infectivity of R5 and X4 HIV-1 Strains in Primary PBMCs and Cervicovaginal Histocultures", PLOS One, Oct. 2013, pp. 1-13 (Year: 2013).*
Abstract ATTS Meeting, May 2012.
Akasheh, R., et al., "Increased Adiposity in Annexin A1-Deficient Mice," Plos One, vol. 8, Issue 12, Dec. 2013, 8 pages.
Bard, David R. "Potential imaging agents for melanoma based on an active analogue of α-melanocyte-stimulating hormone." Drug Delivery (1995); 2.1 : 73-80.
Botte, D. A. C., et al. "Alpha-melanocyte stimulating hormone ameliorates disease activity in an induced murine lupus-like model." Clinical & Experimental Immunology (2014); 177.2: 381-390.
Bowie, James U., et al. "Deciphering the message in protein sequences: tolerance to amino acid substitutions." Science (1990); 247.4948: 1306-1310.
Bracci, Luisa, et al. "Synthetic peptides in the form of dendrimers become resistant to protease activity." Journal of Biological Chemistry (2003); 278.47: 46590-46595.
Cai et al., "Novel 3D pharmacophore of α-MSH/γ-MSH hybrids leads to selective human MC1R and MC3R analogues." Journal of Medicinal Chemistry (2005); 48(6): 1839-1848.
Catania, A., "The Melanocortin System in Control of Inflammation." The Scientific World Journal (2010), 14(10): 1840-1853.
Catania, A., "The melanocortin system in leukocyte biology." Journal of Leukocyte Biology (2007), 81(2): 383-392.
Doi et al., "AP214, an analogue of alpha-melanocyte-stimulating hormone, ameliorates sepsis-induced acute kidney injury and mortality," Kidney International (2008), 73: 1266-1274; advance online publication, Mar. 19, 2008.
EP 13189492.5, Extended European Search Report dated Jan. 17, 2014, 5 pages.
EP 15157262.5, Extended European Search Report dated Aug. 19, 2015, 6 pages.
EP 13189492 Office Action dated Feb. 21, 2014.
Facio, F., et al., "Annexin 1 Mimetic Peptide Protects Against Renal Ischemia/Reperfusion Injury in Rats," J. Mol. Med. 89, 2011, pp. 51-63.

(Continued)

*Primary Examiner* — Lianko G Garyu
(74) *Attorney, Agent, or Firm* — Cooley LLP

(57) ABSTRACT

The present invention relates to peptide analogues comprising one or more branched amino acid probes and a peptide, native or variants thereof.

18 Claims, 1 Drawing Sheet
Specification includes a Sequence Listing.

(56) References Cited

OTHER PUBLICATIONS

Gong, R., "Leveraging melanocortin pathways to treat glomerular diseases." Advances in Chronic Kidney Disease (2014), 21(2): 134-151.
Gong, R., "The renaissance of corticotropin therapy in proteinuric nephropathies." Nature Reviews Nephrology (2011), 8(2):122-128.
Grieco, "D-Amino acid scan of gamma-melanocyte-stimulating hormone: importance of Trp(8) on human MC3 receptor selectivity." Journal of Medicinal Chemistry (2000), 43(26): 4998-5002 (2000).
Haskell-Luevano et al., "Biological and conformational examination of stereochemical modifications using the template melanotropin peptide, Ac-Nle-c[Asp-His-Phe-Arg-Trp-Ala-Lys]-NH2, on human melanocortin receptors." J. Med. Chem. (1997), 40: 1738-1748.
Higuchi et al., "Pro-drugs as novel drug delivery systems." [TOC only] ACS Symposium Series, vol. 14; American Chemical Society, Washington, DC (1975).
Holder et al., "Melanocortin ligands: 30 years of structure-activity relationship (SAR) studies." Med Res Rev. (2004), 24(3): 325-356.
Hunt et al., "Alpha-Melanocyte stimulating hormone and its analogue Nle4DPhe7a-MSH affect morphology, tyrosinase activity and melanogenesis in cultured human melanocytes." Journal of Cell Science (1994), 107: 205-211. Retrieved from URL:<http://jcs.biologists.org/content/107/1/205.full.pdf>.
International Preliminary Report on Patentability for International Application No. PCT/IB2015/000553, dated Oct. 25, 2016, 7 pages.
International Search Report and Written Opinion for International Application No. PCT/IB2015/000553, dated Oct. 8, 2015, 11 pages.
La, M. et al., "Annexin 1 Peptides Protect Against Experimental Myocardial Ischemia-Reperfusion: Analysis of their Mechanism of Action," The FASEB journal vol. 15, No. 12, pp. 2247-2256, Sep. 2017.
Luger and Brzoska. "α-MSH related peptides: a new class of anti-inflammatory and immunomodulating drugs." Ann. Rheum Dis. 66(Suppl III):iii52-iii55.
March et al., "March's advanced organic chemistry, 5th Ed." [TOC only] John Wiley & Sons. (2001).
Mima and Shigeno, "Lipocortin-1 Fails to Ameliorate Ischemic Brain Edema in the Cat." Acta Neurochir (2000); 76: 303-306.
Montero-Melendez et al., "The melanocortin agonist AP214 exerts antiinflammatory and proresolvinq properties." The American Journal of Pathology (2011); 179(1): 259-269.
Ngo, J. Thomas, et al. "Computational complexity, protein structure prediction, and the Levinthal paradox." The protein folding problem and tertiary structure prediction. Merz et al., eds, Birkhauser Boston (19940; pp. 433-506.

PCT Application No. PCT/EP2013/071935, International Preliminary Report on Patentability dated Jan. 21, 2015, 11 pages.
PCT Application No. PCT/EP2013/071935, International Search Report dated Dec. 20, 2013.
PCT Application No. PCT/EP2013/071935, Written Opinion dated Dec. 20, 2013, 6 pages.
Purvis, G., et al., "Endogenous Annexin-A1 is a Protective Determinant in HFD-induced Insulin Resistance and Diabetic Nephropathy," The FASEB Journal, vol. 31, No. 1, Supplement 853.3, Apr. 2017, 1 page.
Raposinho et al., "A 99mTc(CO)3-labeled pyrazolyl-α-melanocyte-stimulating hormone analog conjugate for melanoma targeting," Nuclear Medicine and Biology 35 (2008) 91-99.
Rinne, Petteri, et al. "Pharmacological activation of the melanocortin system limits plaque inflammation and ameliorates vascular dysfunction in atherosclerotic mice." Arteriosclerosis, Thrombosis, and Vascular Biology (2014); 34.7: 1346-1354.
Roche, "Bioreversible carriers in drug design." [TOC only] New York: Pergamon Press (1987).
Steinbruchel et al., "Safety, pharmacokinetics and efficacy of AP214, a novel melanocortin receptor agonist, in patients undergoing cardiac surgery on cadiopulmonary bypass." Abstract TH-P0363, American Society of Nephrology Meeting, Nov. 2011; J Am Soc Nephrol. 22: 2011, p. 196A.
UniProtKB-P04083 (ANXA 1_HUMAN), pp. 1-19; www.uniprot.org/uniprot/P04083#ptm_processing; accessed Apr. 29, 2017; pp. 1-19.
U.S. Appl. No. 14/693,822, Office Action dated Jul. 6, 2016, 19 pages.
U.S. Appl. No. 14/058,790, Notice of Allowance dated Aug. 14, 2015, 8 pages.
U.S. Appl. No. 14/058,790, Office Action dated Apr. 9, 2015, 7 pages.
U.S. Appl. No. 14/951,305, Notice of Allowance dated Jul. 15, 2016, 8 pages.
U.S. Appl. No. 14/693,810, Office Action dated May 4, 2017, 22 pages.
Wang, De-an, et al. "A single amino acid determines lysophospholipid specificity of the S1P1 (EDG1) and LPA1 (EDG2) phospholipid growth factor receptors." Journal of Biological Chemistry (2001); 276.52: 49213-49220.
Wells, James A. "Additivity of mutational effects in proteins." Biochemistry (1990); 29.37: 8509-8517.
Wiggins, RC., "The spectrum of podocytopathies: a unifying view of glomerular diseases." Kidney International (2007), 71(12): 1205-1214.

* cited by examiner

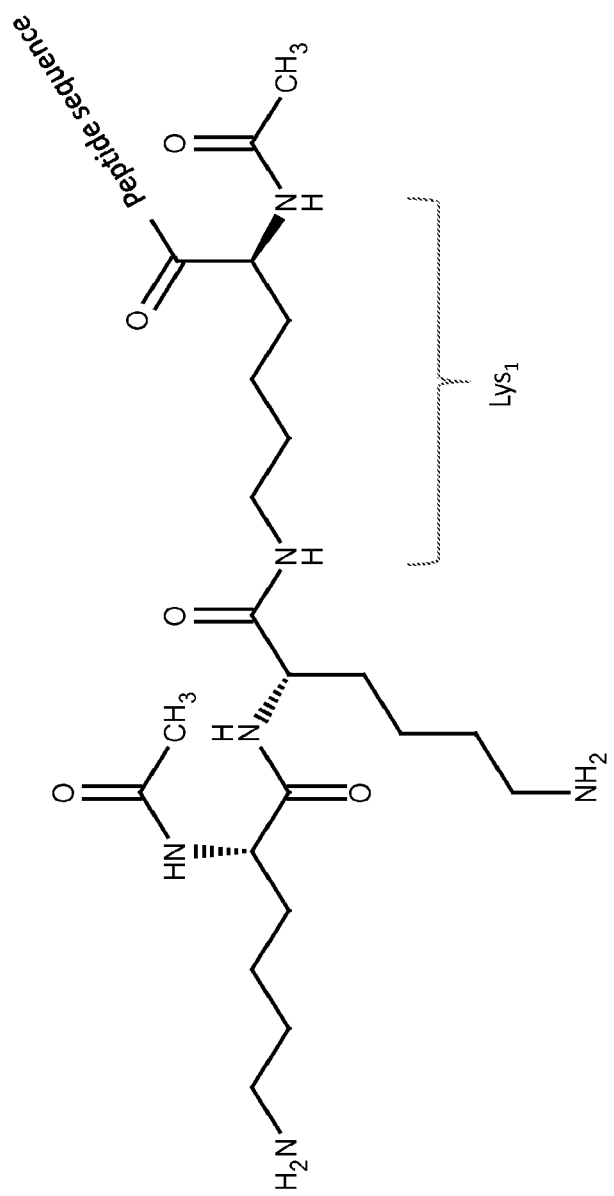

SEQUENCE LISTING

```
<160> NUMBER OF SEQ ID NOS: 201

<210> SEQ ID NO 1
<211> LENGTH: 13
<212> TYPE: PRT
<213> ORGANISM: Homo sapiens

<400> SEQUENCE: 1

Ser Tyr Ser Met Glu His Phe Arg Trp Gly Lys Pro Val
1               5                   10

<210> SEQ ID NO 2
<211> LENGTH: 12
<212> TYPE: PRT
<213> ORGANISM: Homo sapiens

<400> SEQUENCE: 2

Tyr Val Met Gly His Phe Arg Trp Asp Arg Phe Gly
1               5                   10

<210> SEQ ID NO 3
<211> LENGTH: 11
<212> TYPE: PRT
<213> ORGANISM: Homo sapiens

<400> SEQUENCE: 3

Tyr Val Met Gly His Phe Arg Trp Asp Arg Phe
1               5                   10

<210> SEQ ID NO 4
<211> LENGTH: 4
<212> TYPE: PRT
<213> ORGANISM: Homo sapiens

<400> SEQUENCE: 4

His Phe Arg Trp
1
```

```
<210> SEQ ID NO 5
<211> LENGTH: 4
<212> TYPE: PRT
<213> ORGANISM: Artificial Sequence
<220> FEATURE:
<223> OTHER INFORMATION: Synthesized melanocortin peptide fragment
<220> FEATURE:
<221> NAME/KEY: MOD_RES
<222> LOCATION: (2)..(2)
<223> OTHER INFORMATION: D-form phenylalanine

<400> SEQUENCE: 5

His Phe Arg Trp
1

<210> SEQ ID NO 6
<211> LENGTH: 4
<212> TYPE: PRT
<213> ORGANISM: Artificial Sequence
<220> FEATURE:
<223> OTHER INFORMATION: Synthesized melanocortin peptide fragment
<220> FEATURE:
<221> NAME/KEY: MOD_RES
<222> LOCATION: (3)..(3)
<223> OTHER INFORMATION: D-form arginine

<400> SEQUENCE: 6

His Phe Arg Trp
1

<210> SEQ ID NO 7
<211> LENGTH: 4
<212> TYPE: PRT
<213> ORGANISM: Artificial Sequence
<220> FEATURE:
<223> OTHER INFORMATION: Synthesized melanocortin peptide fragment
<220> FEATURE:
<221> NAME/KEY: MOD_RES
<222> LOCATION: (4)..(4)
<223> OTHER INFORMATION: D-form tryptophan

<400> SEQUENCE: 7

His Phe Arg Trp
1

<210> SEQ ID NO 8
<211> LENGTH: 4
<212> TYPE: PRT
<213> ORGANISM: Artificial Sequence
<220> FEATURE:
<223> OTHER INFORMATION: Synthesized melanocortin peptide fragment
<220> FEATURE:
<221> NAME/KEY: MOD_RES
<222> LOCATION: (2)..(2)
<223> OTHER INFORMATION: D-form phenylalanine
<220> FEATURE:
<221> NAME/KEY: MOD_RES
<222> LOCATION: (4)..(4)
<223> OTHER INFORMATION: D-form tryptophan

<400> SEQUENCE: 8

His Phe Arg Trp
1

<210> SEQ ID NO 9
<211> LENGTH: 4
<212> TYPE: PRT
<213> ORGANISM: Artificial Sequence
<220> FEATURE:
```

```
<223> OTHER INFORMATION: Synthesized melanocortin peptide fragment
<220> FEATURE:
<221> NAME/KEY: MOD_RES
<222> LOCATION: (2)..(2)
<223> OTHER INFORMATION: beta-2-naphthyl-alanine

<400> SEQUENCE: 9

His Xaa Arg Trp
1

<210> SEQ ID NO 10
<211> LENGTH: 4
<212> TYPE: PRT
<213> ORGANISM: Artificial Sequence
<220> FEATURE:
<223> OTHER INFORMATION: Synthesized melanocortin peptide fragment
<220> FEATURE:
<221> NAME/KEY: MOD_RES
<222> LOCATION: (2)..(2)
<223> OTHER INFORMATION: D-form beta-2-naphthyl-alanine

<400> SEQUENCE: 10

His Xaa Arg Trp
1

<210> SEQ ID NO 11
<211> LENGTH: 5
<212> TYPE: PRT
<213> ORGANISM: Artificial Sequence
<220> FEATURE:
<223> OTHER INFORMATION: Synthesized melanocortin peptide fragment

<400> SEQUENCE: 11

Ser Tyr Ser Asn Glu
1               5

<210> SEQ ID NO 12
<211> LENGTH: 5
<212> TYPE: PRT
<213> ORGANISM: Artificial sequence
<220> FEATURE:
<223> OTHER INFORMATION: Synthesized melanocortin peptide fragment
<220> FEATURE:
<221> NAME/KEY: MOD_RES
<222> LOCATION: (4)..(4)
<223> OTHER INFORMATION: Nle

<400> SEQUENCE: 12

Ser Tyr Ser Xaa Glu
1               5

<210> SEQ ID NO 13
<211> LENGTH: 5
<212> TYPE: PRT
<213> ORGANISM: Artificial Sequence
<220> FEATURE:
<223> OTHER INFORMATION: Synthesized melanocortin peptide fragment

<400> SEQUENCE: 13

Ser Ser Ile Ile Ser
1               5

<210> SEQ ID NO 14
<211> LENGTH: 4
<212> TYPE: PRT
<213> ORGANISM: Artificial Sequence
<220> FEATURE:
<223> OTHER INFORMATION: Synthesized melanocortin peptide fragment
```

```
<400> SEQUENCE: 14

Tyr Val Asn Gly
1

<210> SEQ ID NO 15
<211> LENGTH: 4
<212> TYPE: PRT
<213> ORGANISM: Artificial Sequence
<220> FEATURE:
<223> OTHER INFORMATION: Synthesized melanocortin peptide fragment
<220> FEATURE:
<221> NAME/KEY: MOD_RES
<222> LOCATION: (3)..(3)
<223> OTHER INFORMATION: Nle

<400> SEQUENCE: 15

Tyr Val Xaa Gly
1

<210> SEQ ID NO 16
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (7)..(7)
<223> OTHER INFORMATION: D-form phenylalanine

<400> SEQUENCE: 16

Ser Tyr Ser Met Glu His Phe Arg Trp Gly Lys Pro Val
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (8)..(8)
<223> OTHER INFORMATION: D-form arginine

<400> SEQUENCE: 17

Ser Tyr Ser Met Glu His Phe Arg Trp Gly Lys Pro Val
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (9)..(9)
<223> OTHER INFORMATION: D-form tryptophan

<400> SEQUENCE: 18

Ser Tyr Ser Met Glu His Phe Arg Trp Gly Lys Pro Val
1               5                   10

<210> SEQ ID NO 19
<211> LENGTH: 13
<212> TYPE: PRT
<213> ORGANISM: Artificial Sequence
<220> FEATURE:
```

<223> OTHER INFORMATION: Synthesized melanocortin analogue
<220> FEATURE:
<221> NAME/KEY: MOD_RES
<222> LOCATION: (7)..(7)
<223> OTHER INFORMATION: D-form phenylalanine
<220> FEATURE:
<221> NAME/KEY: MOD_RES
<222> LOCATION: (9)..(9)
<223> OTHER INFORMATION: D-form tryptophan

<400> SEQUENCE: 19

Ser Tyr Ser Met Glu His Phe Arg Trp Gly Lys Pro Val
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (7)..(7)
<223> OTHER INFORMATION: beta-2-naphthyl-alanine

<400> SEQUENCE: 20

Ser Tyr Ser Met Glu His Xaa Arg Trp Gly Lys Pro Val
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (7)..(7)
<223> OTHER INFORMATION: D-form beta-2-naphthyl-alanine

<400> SEQUENCE: 21

Ser Tyr Ser Met Glu His Xaa Arg Trp Gly Lys Pro Val
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (13)..(13)
<223> OTHER INFORMATION: D-form valine

<400> SEQUENCE: 22

Ser Tyr Ser Met Glu His Phe Arg Trp Gly Lys Pro Val
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (7)..(7)
<223> OTHER INFORMATION: D-form phenylalanine
<220> FEATURE:
<221> NAME/KEY: MOD_RES
<222> LOCATION: (13)..(13)
<223> OTHER INFORMATION: D-form valine

<400> SEQUENCE: 23

Ser Tyr Ser Met Glu His Phe Arg Trp Gly Lys Pro Val
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (8)..(8)
<223> OTHER INFORMATION: D-form arginine
<220> FEATURE:
<221> NAME/KEY: MOD_RES
<222> LOCATION: (13)..(13)
<223> OTHER INFORMATION: D-form valine

<400> SEQUENCE: 24

Ser Tyr Ser Met Glu His Phe Arg Trp Gly Lys Pro Val
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (9)..(9)
<223> OTHER INFORMATION: D-form tyrptophan
<220> FEATURE:
<221> NAME/KEY: MOD_RES
<222> LOCATION: (13)..(13)
<223> OTHER INFORMATION: D-form valine

<400> SEQUENCE: 25

Ser Tyr Ser Met Glu His Phe Arg Trp Gly Lys Pro Val
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (7)..(7)
<223> OTHER INFORMATION: D-form phenylalanine
<220> FEATURE:
<221> NAME/KEY: MOD_RES
<222> LOCATION: (9)..(9)
<223> OTHER INFORMATION: D-form tyrptophan
<220> FEATURE:
<221> NAME/KEY: MOD_RES
<222> LOCATION: (13)..(13)
<223> OTHER INFORMATION: D-form valine

<400> SEQUENCE: 26

Ser Tyr Ser Met Glu His Phe Arg Trp Gly Lys Pro Val
1               5                   10

<210> SEQ ID NO 27
<211> LENGTH: 13
<212> TYPE: PRT

```
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (7)..(7)
<223> OTHER INFORMATION: beta-2-naphthyl-alanine
<220> FEATURE:
<221> NAME/KEY: MOD_RES
<222> LOCATION: (13)..(13)
<223> OTHER INFORMATION: D-form valine

<400> SEQUENCE: 27

Ser Tyr Ser Met Glu His Xaa Arg Trp Gly Lys Pro Val
1               5                   10

<210> SEQ ID NO 28
<211> LENGTH: 13
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: D-form beta-2-naphthyl-alanine
<220> FEATURE:
<221> NAME/KEY: MOD_RES
<222> LOCATION: (13)..(13)
<223> OTHER INFORMATION: D-form valine

<400> SEQUENCE: 28

Ser Tyr Ser Met Glu His Xaa Arg Trp Gly Lys Pro Val
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (4)..(4)
<223> OTHER INFORMATION: Nle

<400> SEQUENCE: 29

Ser Tyr Ser Xaa Glu His Phe Arg Trp Gly Lys Pro Val
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D-form phenylalanine

<400> SEQUENCE: 30

Ser Tyr Ser Xaa Glu His Phe Arg Trp Gly Lys Pro Val
1               5                   10

<210> SEQ ID NO 31
<211> LENGTH: 13
<212> TYPE: PRT
<213> ORGANISM: Artificial Sequence
```

```
<220> FEATURE:
<223> OTHER INFORMATION: Synthesized melanocortin analogue
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (8)..(8)
<223> OTHER INFORMATION: D-form arginine

<400> SEQUENCE: 31

Ser Tyr Ser Xaa Glu His Phe Arg Trp Gly Lys Pro Val
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (9)..(9)
<223> OTHER INFORMATION: D-form tryptophan

<400> SEQUENCE: 32

Ser Tyr Ser Xaa Glu His Phe Arg Trp Gly Lys Pro Val
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (9)..(9)
<223> OTHER INFORMATION: D-form tryptophan

<400> SEQUENCE: 33

Ser Tyr Ser Xaa Glu His Phe Arg Trp Gly Lys Pro Val
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: beta-2-naphthyl-alanine

<400> SEQUENCE: 34

Ser Tyr Ser Xaa Glu His Xaa Arg Trp Gly Lys Pro Val
1               5                   10
```

```
<210> SEQ ID NO 35
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D-form beta-2-naphthyl-alanine

<400> SEQUENCE: 35

Ser Tyr Ser Xaa Glu His Xaa Arg Trp Gly Lys Pro Val
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (13)..(13)
<223> OTHER INFORMATION: D-form valine

<400> SEQUENCE: 36

Ser Tyr Ser Xaa Glu His Phe Arg Trp Gly Lys Pro Val
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D-form phenylalanine
<220> FEATURE:
<221> NAME/KEY: MOD_RES
<222> LOCATION: (13)..(13)
<223> OTHER INFORMATION: D-form valine

<400> SEQUENCE: 37

Ser Tyr Ser Xaa Glu His Phe Arg Trp Gly Lys Pro Val
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (4)..(4)
<223> OTHER INFORMATION: Nle
<220> FEATURE:
```

```
<221> NAME/KEY: MOD_RES
<222> LOCATION: (8)..(8)
<223> OTHER INFORMATION: D-form arginine
<220> FEATURE:
<221> NAME/KEY: MOD_RES
<222> LOCATION: (13)..(13)
<223> OTHER INFORMATION: D-form valine

<400> SEQUENCE: 38

Ser Tyr Ser Xaa Glu His Phe Arg Trp Gly Lys Pro Val
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (9)..(9)
<223> OTHER INFORMATION: D-form tryptophan
<220> FEATURE:
<221> NAME/KEY: MOD_RES
<222> LOCATION: (13)..(13)
<223> OTHER INFORMATION: D-form valine

<400> SEQUENCE: 39

Ser Tyr Ser Xaa Glu His Phe Arg Trp Gly Lys Pro Val
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D-form phenylalanine
<220> FEATURE:
<221> NAME/KEY: MOD_RES
<222> LOCATION: (9)..(9)
<223> OTHER INFORMATION: D-form tryptophan
<220> FEATURE:
<221> NAME/KEY: MOD_RES
<222> LOCATION: (13)..(13)
<223> OTHER INFORMATION: D-form valine

<400> SEQUENCE: 40

Ser Tyr Ser Xaa Glu His Phe Arg Trp Gly Lys Pro Val
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (4)..(4)
<223> OTHER INFORMATION: Nle
<220> FEATURE:
```

```
<221> NAME/KEY: MOD_RES
<222> LOCATION: (7)..(7)
<223> OTHER INFORMATION: beta-2-naphthyl-alanine
<220> FEATURE:
<221> NAME/KEY: MOD_RES
<222> LOCATION: (13)..(13)
<223> OTHER INFORMATION: D-form valine

<400> SEQUENCE: 41

Ser Tyr Ser Xaa Glu His Xaa Arg Trp Gly Lys Pro Val
1               5                   10

<210> SEQ ID NO 42
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (7)..(7)
<223> OTHER INFORMATION: D-form beta-2-naphthyl-alanine
<220> FEATURE:
<221> NAME/KEY: MOD_RES
<222> LOCATION: (13)..(13)
<223> OTHER INFORMATION: D-form valine

<400> SEQUENCE: 42

Ser Tyr Ser Xaa Glu His Xaa Arg Trp Gly Lys Pro Val
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Synthesized melanocortin analogue

<400> SEQUENCE: 43

Ser Ser Ile Ile Ser His Phe Arg Trp Gly Lys Pro Val
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (7)..(7)
<223> OTHER INFORMATION: D-form phenylalanine

<400> SEQUENCE: 44

Ser Ser Ile Ile Ser His Phe Arg Trp Gly Lys Pro Val
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (8)..(8)
<223> OTHER INFORMATION: D-form arginine
```

```
<400> SEQUENCE: 45

Ser Ser Ile Ile Ser His Phe Arg Trp Gly Lys Pro Val
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (9)..(9)
<223> OTHER INFORMATION: D-form tryptophan

<400> SEQUENCE: 46

Ser Ser Ile Ile Ser His Phe Arg Trp Gly Lys Pro Val
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (7)..(7)
<223> OTHER INFORMATION: D-form phenylalanine
<220> FEATURE:
<221> NAME/KEY: MOD_RES
<222> LOCATION: (9)..(9)
<223> OTHER INFORMATION: D-form tryptophan

<400> SEQUENCE: 47

Ser Ser Ile Ile Ser His Phe Arg Trp Gly Lys Pro Val
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (7)..(7)
<223> OTHER INFORMATION: beta-2-naphthyl-alanine

<400> SEQUENCE: 48

Ser Ser Ile Ile Ser His Xaa Arg Trp Gly Lys Pro Val
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (7)..(7)
<223> OTHER INFORMATION: D-form beta-2-naphthyl-alanine

<400> SEQUENCE: 49

Ser Ser Ile Ile Ser His Xaa Arg Trp Gly Lys Pro Val
1               5                   10
```

```
<210> SEQ ID NO 50
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (13)..(13)
<223> OTHER INFORMATION: D-form valine

<400> SEQUENCE: 50

Ser Ser Ile Ile Ser His Phe Arg Trp Gly Lys Pro Val
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (7)..(7)
<223> OTHER INFORMATION: D-form phenylalanine
<220> FEATURE:
<221> NAME/KEY: MOD_RES
<222> LOCATION: (13)..(13)
<223> OTHER INFORMATION: D-form valine

<400> SEQUENCE: 51

Ser Ser Ile Ile Ser His Phe Arg Trp Gly Lys Pro Val
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (8)..(8)
<223> OTHER INFORMATION: D-form arginine
<220> FEATURE:
<221> NAME/KEY: MOD_RES
<222> LOCATION: (13)..(13)
<223> OTHER INFORMATION: D-form valine

<400> SEQUENCE: 52

Ser Ser Ile Ile Ser His Phe Arg Trp Gly Lys Pro Val
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (9)..(9)
<223> OTHER INFORMATION: D-form tryptophan
<220> FEATURE:
<221> NAME/KEY: MOD_RES
<222> LOCATION: (13)..(13)
<223> OTHER INFORMATION: D-form valine

<400> SEQUENCE: 53

Ser Ser Ile Ile Ser His Phe Arg Trp Gly Lys Pro Val
1               5                   10
```

```
<210> SEQ ID NO 54
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (7)..(7)
<223> OTHER INFORMATION: D-form phenylalanine
<220> FEATURE:
<221> NAME/KEY: MOD_RES
<222> LOCATION: (9)..(9)
<223> OTHER INFORMATION: D-form tryptophan
<220> FEATURE:
<221> NAME/KEY: MOD_RES
<222> LOCATION: (13)..(13)
<223> OTHER INFORMATION: D-form valine

<400> SEQUENCE: 54

Ser Ser Ile Ile Ser His Phe Arg Trp Gly Lys Pro Val
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (7)..(7)
<223> OTHER INFORMATION: beta-2-naphthyl-alanine
<220> FEATURE:
<221> NAME/KEY: MOD_RES
<222> LOCATION: (13)..(13)
<223> OTHER INFORMATION: D-form valine

<400> SEQUENCE: 55

Ser Ser Ile Ile Ser His Xaa Arg Trp Gly Lys Pro Val
1               5                   10

<210> SEQ ID NO 56
<211> LENGTH: 13
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (7)..(7)
<223> OTHER INFORMATION: D-form beta-2-naphthyl-alanine
<220> FEATURE:
<221> NAME/KEY: MOD_RES
<222> LOCATION: (13)..(13)
<223> OTHER INFORMATION: D-form valine

<400> SEQUENCE: 56

Ser Ser Ile Ile Ser His Xaa Arg Trp Gly Lys Pro Val
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (6)..(6)
<223> OTHER INFORMATION: D-form phenylalanine
```

-continued

<400> SEQUENCE: 57

Tyr Val Met Gly His Phe Arg Trp Asp Arg Phe Gly
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (7)..(7)
<223> OTHER INFORMATION: D-form arginine

<400> SEQUENCE: 58

Tyr Val Met Gly His Phe Arg Trp Asp Arg Phe Gly
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (8)..(8)
<223> OTHER INFORMATION: D-form tryptophan

<400> SEQUENCE: 59

Tyr Val Met Gly His Phe Arg Trp Asp Arg Phe Gly
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (6)..(6)
<223> OTHER INFORMATION: D-form phenylalanine
<220> FEATURE:
<221> NAME/KEY: MOD_RES
<222> LOCATION: (8)..(8)
<223> OTHER INFORMATION: D-form tryptophan

<400> SEQUENCE: 60

Tyr Val Met Gly His Phe Arg Trp Asp Arg Phe Gly
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (6)..(6)
<223> OTHER INFORMATION: beta-2-naphthyl-alanine

<400> SEQUENCE: 61

Tyr Val Met Gly His Xaa Arg Trp Asp Arg Phe Gly
1               5                   10

<210> SEQ ID NO 62

```
<211> LENGTH: 12
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (6)..(6)
<223> OTHER INFORMATION: D-form beta-2-naphthyl-alanine

<400> SEQUENCE: 62

Tyr Val Met Gly His Xaa Arg Trp Asp Arg Phe Gly
1               5                   10

<210> SEQ ID NO 63
<211> LENGTH: 12
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (11)..(11)
<223> OTHER INFORMATION: D-form phenylalanine

<400> SEQUENCE: 63

Tyr Val Met Gly His Phe Arg Trp Asp Arg Phe Gly
1               5                   10

<210> SEQ ID NO 64
<211> LENGTH: 12
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (6)..(6)
<223> OTHER INFORMATION: D-form phenylalanine
<220> FEATURE:
<221> NAME/KEY: MOD_RES
<222> LOCATION: (11)..(11)
<223> OTHER INFORMATION: D-form phenylalanine

<400> SEQUENCE: 64

Tyr Val Met Gly His Phe Arg Trp Asp Arg Phe Gly
1               5                   10

<210> SEQ ID NO 65
<211> LENGTH: 12
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (7)..(7)
<223> OTHER INFORMATION: D-form arginine
<220> FEATURE:
<221> NAME/KEY: MOD_RES
<222> LOCATION: (11)..(11)
<223> OTHER INFORMATION: D-form phenylalanine

<400> SEQUENCE: 65

Tyr Val Met Gly His Phe Arg Trp Asp Arg Phe Gly
1               5                   10

<210> SEQ ID NO 66
<211> LENGTH: 12
<212> TYPE: PRT
<213> ORGANISM: Artificial Sequence
```

```
<220> FEATURE:
<223> OTHER INFORMATION: Synthesized melanocortin analogue
<220> FEATURE:
<221> NAME/KEY: MOD_RES
<222> LOCATION: (8)..(8)
<223> OTHER INFORMATION: D-form tryptophan
<220> FEATURE:
<221> NAME/KEY: MOD_RES
<222> LOCATION: (11)..(11)
<223> OTHER INFORMATION: D-form phenylalanine

<400> SEQUENCE: 66

Tyr Val Met Gly His Phe Arg Trp Asp Arg Phe Gly
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (6)..(6)
<223> OTHER INFORMATION: D-form phenylalanine
<220> FEATURE:
<221> NAME/KEY: MOD_RES
<222> LOCATION: (8)..(8)
<223> OTHER INFORMATION: D-form tryptophan
<220> FEATURE:
<221> NAME/KEY: MOD_RES
<222> LOCATION: (11)..(11)
<223> OTHER INFORMATION: D-form phenylalanine

<400> SEQUENCE: 67

Tyr Val Met Gly His Phe Arg Trp Asp Arg Phe Gly
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (6)..(6)
<223> OTHER INFORMATION: beta-2-naphthyl-alanine
<220> FEATURE:
<221> NAME/KEY: MOD_RES
<222> LOCATION: (11)..(11)
<223> OTHER INFORMATION: D-form phenylalanine

<400> SEQUENCE: 68

Tyr Val Met Gly His Xaa Arg Trp Asp Arg Phe Gly
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (6)..(6)
<223> OTHER INFORMATION: D-form beta-2-naphthyl-alanine
<220> FEATURE:
<221> NAME/KEY: MOD_RES
<222> LOCATION: (11)..(11)
<223> OTHER INFORMATION: D-form phenylalanine

<400> SEQUENCE: 69
```

Tyr Val Met Gly His Xaa Arg Trp Asp Arg Phe Gly
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (3)..(3)
<223> OTHER INFORMATION: Nle

<400> SEQUENCE: 70

Tyr Val Xaa Gly His Phe Arg Trp Asp Arg Phe Gly
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (6)..(6)
<223> OTHER INFORMATION: D-form phenylalanine

<400> SEQUENCE: 71

Tyr Val Xaa Gly His Phe Arg Trp Asp Arg Phe Gly
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (7)..(7)
<223> OTHER INFORMATION: D-form arginine

<400> SEQUENCE: 72

Tyr Val Xaa Gly His Phe Arg Trp Asp Arg Phe Gly
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (8)..(8)
<223> OTHER INFORMATION: D-form tryptophan

```
<400> SEQUENCE: 73

Tyr Val Xaa Gly His Phe Arg Trp Asp Arg Phe Gly
1               5                   10

<210> SEQ ID NO 74
<211> LENGTH: 12
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (6)..(6)
<223> OTHER INFORMATION: D-form phenylalanine
<220> FEATURE:
<221> NAME/KEY: MOD_RES
<222> LOCATION: (8)..(8)
<223> OTHER INFORMATION: D-form tryptophan

<400> SEQUENCE: 74

Tyr Val Xaa Gly His Phe Arg Trp Asp Arg Phe Gly
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (6)..(6)
<223> OTHER INFORMATION: beta-2-naphthyl-alanine

<400> SEQUENCE: 75

Tyr Val Xaa Gly His Xaa Arg Trp Asp Arg Phe Gly
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (6)..(6)
<223> OTHER INFORMATION: D-form beta-2-naphthyl-alanine

<400> SEQUENCE: 76

Tyr Val Xaa Gly His Xaa Arg Trp Asp Arg Phe Gly
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Synthesized melanocortin analogue
```

```
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (11)..(11)
<223> OTHER INFORMATION: D-form phenylalanine

<400> SEQUENCE: 77

Tyr Val Xaa Gly His Phe Arg Trp Asp Arg Phe Gly
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (6)..(6)
<223> OTHER INFORMATION: D-form phenylalanine
<220> FEATURE:
<221> NAME/KEY: MOD_RES
<222> LOCATION: (11)..(11)
<223> OTHER INFORMATION: D-form phenylalanine

<400> SEQUENCE: 78

Tyr Val Xaa Gly His Phe Arg Trp Asp Arg Phe Gly
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (7)..(7)
<223> OTHER INFORMATION: D-form arginine
<220> FEATURE:
<221> NAME/KEY: MOD_RES
<222> LOCATION: (11)..(11)
<223> OTHER INFORMATION: D-form phenylalanine

<400> SEQUENCE: 79

Tyr Val Xaa Gly His Phe Arg Trp Asp Arg Phe Gly
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (8)..(8)
<223> OTHER INFORMATION: D-form tryptophan
```

```
<220> FEATURE:
<221> NAME/KEY: MOD_RES
<222> LOCATION: (11)..(11)
<223> OTHER INFORMATION: D-form phenylalanine

<400> SEQUENCE: 80

Tyr Val Xaa Gly His Phe Arg Trp Asp Arg Phe Gly
1               5                   10

<210> SEQ ID NO 81
<211> LENGTH: 12
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (6)..(6)
<223> OTHER INFORMATION: D-form phenylalanine
<220> FEATURE:
<221> NAME/KEY: MOD_RES
<222> LOCATION: (8)..(8)
<223> OTHER INFORMATION: D-form tryptophan
<220> FEATURE:
<221> NAME/KEY: MOD_RES
<222> LOCATION: (11)..(11)
<223> OTHER INFORMATION: D-form phenylalanine

<400> SEQUENCE: 81

Tyr Val Xaa Gly His Phe Arg Trp Asp Arg Phe Gly
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (6)..(6)
<223> OTHER INFORMATION: beta-2-naphthyl-alanine
<220> FEATURE:
<221> NAME/KEY: MOD_RES
<222> LOCATION: (11)..(11)
<223> OTHER INFORMATION: D-form phenylalanine

<400> SEQUENCE: 82

Tyr Val Xaa Gly His Xaa Arg Trp Asp Arg Phe Gly
1               5                   10

<210> SEQ ID NO 83
<211> LENGTH: 12
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (6)..(6)
<223> OTHER INFORMATION: D-form beta-2-naphthyl-alanine
```

```
<220> FEATURE:
<221> NAME/KEY: MOD_RES
<222> LOCATION: (11)..(11)
<223> OTHER INFORMATION: D-form phenylalanine

<400> SEQUENCE: 83

Tyr Val Xaa Gly His Xaa Arg Trp Asp Arg Phe Gly
1               5                   10

<210> SEQ ID NO 84
<211> LENGTH: 11
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (6)..(6)
<223> OTHER INFORMATION: D-form phenylalanine

<400> SEQUENCE: 84

Tyr Val Met Gly His Phe Arg Trp Asp Arg Phe
1               5                   10

<210> SEQ ID NO 85
<211> LENGTH: 11
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (7)..(7)
<223> OTHER INFORMATION: D-form arginine

<400> SEQUENCE: 85

Tyr Val Met Gly His Phe Arg Trp Asp Arg Phe
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (8)..(8)
<223> OTHER INFORMATION: D-form tryptophan

<400> SEQUENCE: 86

Tyr Val Met Gly His Phe Arg Trp Asp Arg Phe
1               5                   10

<210> SEQ ID NO 87
<211> LENGTH: 11
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (6)..(6)
<223> OTHER INFORMATION: D-form phenylalanine
<220> FEATURE:
<221> NAME/KEY: MOD_RES
<222> LOCATION: (8)..(8)
<223> OTHER INFORMATION: D-form tryptophan

<400> SEQUENCE: 87
```

Tyr Val Met Gly His Phe Arg Trp Asp Arg Phe
1               5                   10

<210> SEQ ID NO 88
<211> LENGTH: 11
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (6)..(6)
<223> OTHER INFORMATION: beta-2-naphthyl-alanine

<400> SEQUENCE: 88

Tyr Val Met Gly His Xaa Arg Trp Asp Arg Phe
1               5                   10

<210> SEQ ID NO 89
<211> LENGTH: 11
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (6)..(6)
<223> OTHER INFORMATION: D-form beta-2-naphthyl-alanine

<400> SEQUENCE: 89

Tyr Val Met Gly His Xaa Arg Trp Asp Arg Phe
1               5                   10

<210> SEQ ID NO 90
<211> LENGTH: 11
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (11)..(11)
<223> OTHER INFORMATION: D-form phenylalanine

<400> SEQUENCE: 90

Tyr Val Met Gly His Phe Arg Trp Asp Arg Phe
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (6)..(6)
<223> OTHER INFORMATION: D-form phenylalanine
<220> FEATURE:
<221> NAME/KEY: MOD_RES
<222> LOCATION: (11)..(11)
<223> OTHER INFORMATION: D-form phenylalanine

<400> SEQUENCE: 91

Tyr Val Met Gly His Phe Arg Trp Asp Arg Phe
1               5                   10

<210> SEQ ID NO 92
<211> LENGTH: 11
<212> TYPE: PRT

```
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (7)..(7)
<223> OTHER INFORMATION: D-form arginine
<220> FEATURE:
<221> NAME/KEY: MOD_RES
<222> LOCATION: (11)..(11)
<223> OTHER INFORMATION: D-form phenylalanine

<400> SEQUENCE: 92

Tyr Val Met Gly His Phe Arg Trp Asp Arg Phe
1               5                   10

<210> SEQ ID NO 93
<211> LENGTH: 11
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (8)..(8)
<223> OTHER INFORMATION: D-form tryptophan
<220> FEATURE:
<221> NAME/KEY: MOD_RES
<222> LOCATION: (11)..(11)
<223> OTHER INFORMATION: D-form phenylalanine

<400> SEQUENCE: 93

Tyr Val Met Gly His Phe Arg Trp Asp Arg Phe
1               5                   10

<210> SEQ ID NO 94
<211> LENGTH: 11
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (6)..(6)
<223> OTHER INFORMATION: D-form phenylalanine
<220> FEATURE:
<221> NAME/KEY: MOD_RES
<222> LOCATION: (8)..(8)
<223> OTHER INFORMATION: D-form tryptophan
<220> FEATURE:
<221> NAME/KEY: MOD_RES
<222> LOCATION: (11)..(11)
<223> OTHER INFORMATION: D-form phenylalanine

<400> SEQUENCE: 94

Tyr Val Met Gly His Phe Arg Trp Asp Arg Phe
1               5                   10

<210> SEQ ID NO 95
<211> LENGTH: 11
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (6)..(6)
<223> OTHER INFORMATION: beta-2-naphthyl-alanine
<220> FEATURE:
<221> NAME/KEY: MOD_RES
<222> LOCATION: (11)..(11)
<223> OTHER INFORMATION: D-form phenylalanine
```

```
<400> SEQUENCE: 95

Tyr Val Met Gly His Xaa Arg Trp Asp Arg Phe
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (6)..(6)
<223> OTHER INFORMATION: D-form beta-2-naphthyl-alanine
<220> FEATURE:
<221> NAME/KEY: MOD_RES
<222> LOCATION: (11)..(11)
<223> OTHER INFORMATION: D-form phenylalanine

<400> SEQUENCE: 96

Tyr Val Met Gly His Xaa Arg Trp Asp Arg Phe
1               5                   10

<210> SEQ ID NO 97
<211> LENGTH: 11
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (3)..(3)
<223> OTHER INFORMATION: Nle

<400> SEQUENCE: 97

Tyr Val Xaa Gly His Phe Arg Trp Asp Arg Phe
1               5                   10

<210> SEQ ID NO 98
<211> LENGTH: 11
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (6)..(6)
<223> OTHER INFORMATION: D-form phenylalanine

<400> SEQUENCE: 98

Tyr Val Xaa Gly His Phe Arg Trp Asp Arg Phe
1               5                   10

<210> SEQ ID NO 99
<211> LENGTH: 11
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (7)..(7)
<223> OTHER INFORMATION: D-form arginine
```

<400> SEQUENCE: 99

Tyr Val Xaa Gly His Phe Arg Trp Asp Arg Phe
1               5                   10

<210> SEQ ID NO 100
<211> LENGTH: 11
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (8)..(8)
<223> OTHER INFORMATION: D-form tryptophan

<400> SEQUENCE: 100

Tyr Val Xaa Gly His Phe Arg Trp Asp Arg Phe
1               5                   10

<210> SEQ ID NO 101
<211> LENGTH: 11
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (6)..(6)
<223> OTHER INFORMATION: D-form phenylalanine
<220> FEATURE:
<221> NAME/KEY: MOD_RES
<222> LOCATION: (8)..(8)
<223> OTHER INFORMATION: D-form tryptophan

<400> SEQUENCE: 101

Tyr Val Xaa Gly His Phe Arg Trp Asp Arg Phe
1               5                   10

<210> SEQ ID NO 102
<211> LENGTH: 11
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (6)..(6)
<223> OTHER INFORMATION: beta-2-naphthyl-alanine

<400> SEQUENCE: 102

Tyr Val Xaa Gly His Xaa Arg Trp Asp Arg Phe
1               5                   10

<210> SEQ ID NO 103
<211> LENGTH: 11
<212> TYPE: PRT
<213> ORGANISM: Artificial Sequence
<220> FEATURE:

```
<223> OTHER INFORMATION: Synthesized melanocortin analogue
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (6)..(6)
<223> OTHER INFORMATION: D-form beta-2-naphthyl-alanine

<400> SEQUENCE: 103

Tyr Val Xaa Gly His Xaa Arg Trp Asp Arg Phe
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (11)..(11)
<223> OTHER INFORMATION: D-form phenylalanine

<400> SEQUENCE: 104

Tyr Val Xaa Gly His Phe Arg Trp Asp Arg Phe
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (6)..(6)
<223> OTHER INFORMATION: D-form phenylalanine
<220> FEATURE:
<221> NAME/KEY: MOD_RES
<222> LOCATION: (11)..(11)
<223> OTHER INFORMATION: D-form phenylalanine

<400> SEQUENCE: 105

Tyr Val Xaa Gly His Phe Arg Trp Asp Arg Phe
1               5                   10

<210> SEQ ID NO 106
<211> LENGTH: 11
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (7)..(7)
<223> OTHER INFORMATION: D-form arginine
<220> FEATURE:
<221> NAME/KEY: MOD_RES
<222> LOCATION: (11)..(11)
```

```
<223> OTHER INFORMATION: D-form phenylalanine

<400> SEQUENCE: 106

Tyr Val Xaa Gly His Phe Arg Trp Asp Arg Phe
1               5                   10

<210> SEQ ID NO 107
<211> LENGTH: 11
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (8)..(8)
<223> OTHER INFORMATION: D-form tryptophan
<220> FEATURE:
<221> NAME/KEY: MOD_RES
<222> LOCATION: (11)..(11)
<223> OTHER INFORMATION: D-form phenylalanine

<400> SEQUENCE: 107

Tyr Val Xaa Gly His Phe Arg Trp Asp Arg Phe
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (6)..(6)
<223> OTHER INFORMATION: D-form phenylalanine
<220> FEATURE:
<221> NAME/KEY: MOD_RES
<222> LOCATION: (8)..(8)
<223> OTHER INFORMATION: D-form tryptophan
<220> FEATURE:
<221> NAME/KEY: MOD_RES
<222> LOCATION: (11)..(11)
<223> OTHER INFORMATION: D-form phenylalanine

<400> SEQUENCE: 108

Tyr Val Xaa Gly His Phe Arg Trp Asp Arg Phe
1               5                   10

<210> SEQ ID NO 109
<211> LENGTH: 11
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (6)..(6)
<223> OTHER INFORMATION: beta-2-naphthyl-alanine
<220> FEATURE:
<221> NAME/KEY: MOD_RES
<222> LOCATION: (11)..(11)
```

<223> OTHER INFORMATION: D-form phenylalanine

<400> SEQUENCE: 109

Tyr Val Xaa Gly His Xaa Arg Trp Asp Arg Phe
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Synthesized melanocortin analogue
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (6)..(6)
<223> OTHER INFORMATION: D-form beta-2-naphthyl-alanine
<220> FEATURE:
<221> NAME/KEY: MOD_RES
<222> LOCATION: (11)..(11)
<223> OTHER INFORMATION: D-form phenylalanine

<400> SEQUENCE: 110

Tyr Val Xaa Gly His Xaa Arg Trp Asp Arg Phe
1               5                   10

<210> SEQ ID NO 111
<211> LENGTH: 7
<212> TYPE: PRT
<213> ORGANISM: Artificial Sequence
<220> FEATURE:
<223> OTHER INFORMATION: Synthesized cyclic lactam analogue
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: D-form phenylalanine

<400> SEQUENCE: 111

Xaa Asp His Phe Arg Trp Lys
1               5

<210> SEQ ID NO 112
<211> LENGTH: 31
<212> TYPE: PRT
<213> ORGANISM: Homo sapiens

<400> SEQUENCE: 112

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 113
<211> LENGTH: 34
<212> TYPE: PRT
<213> ORGANISM: Homo sapiens

<400> SEQUENCE: 113

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr

```
                20                  25                  30

Asp Arg

<210> SEQ ID NO 114
<211> LENGTH: 6
<212> TYPE: PRT
<213> ORGANISM: Artificial Sequence
<220> FEATURE:
<223> OTHER INFORMATION: Synthesized control peptide

<400> SEQUENCE: 114

Trp Lys Tyr Met Val Met
1               5

<210> SEQ ID NO 115
<211> LENGTH: 25
<212> TYPE: PRT
<213> ORGANISM: Homo sapiens

<400> SEQUENCE: 115

Ala Met Val Ser Glu Phe Leu Lys Gln Ala Trp Phe Ile Glu Asn Glu
1               5                   10                  15

Glu Gln Glu Tyr Val Gln Thr Val Lys
            20                  25

<210> SEQ ID NO 116
<211> LENGTH: 11
<212> TYPE: PRT
<213> ORGANISM: Homo sapiens

<400> SEQUENCE: 116

Ala Met Val Ser Glu Phe Leu Lys Gln Ala Trp
1               5                   10

<210> SEQ ID NO 117
<211> LENGTH: 4
<212> TYPE: PRT
<213> ORGANISM: Artificial Sequence
<220> FEATURE:
<223> OTHER INFORMATION: Synthesized peptide analogue

<400> SEQUENCE: 117

Lys Lys Lys Lys
1

<210> SEQ ID NO 118
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(1)
<223> OTHER INFORMATION: ACETYLATION

<400> SEQUENCE: 118

Lys Lys Lys Lys
1

<210> SEQ ID NO 119
<211> LENGTH: 4
<212> TYPE: PRT
<213> ORGANISM: Artificial Sequence
<220> FEATURE:
<223> OTHER INFORMATION: Synthesized peptide analogue
```

```
<220> FEATURE:
<221> NAME/KEY: MOD_RES
<222> LOCATION: (1)..(1)
<223> OTHER INFORMATION: Xaa is Arg, His, Gly or Ala

<400> SEQUENCE: 119

Xaa Lys Lys Lys
1

<210> SEQ ID NO 120
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(2)
<223> OTHER INFORMATION: Xaa is Arg, His, Gly or Ala

<400> SEQUENCE: 120

Xaa Xaa Lys Lys
1

<210> SEQ ID NO 121
<211> LENGTH: 5
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(2)
<223> OTHER INFORMATION: Xaa is Arg, His, Gly or Ala

<400> SEQUENCE: 121

Xaa Xaa Lys Lys Lys
1               5

<210> SEQ ID NO 122
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(3)
<223> OTHER INFORMATION: Xaa is Arg, His, Gly or Ala

<400> SEQUENCE: 122

Xaa Xaa Xaa Lys
1

<210> SEQ ID NO 123
<211> LENGTH: 5
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(3)
<223> OTHER INFORMATION: Xaa is Arg, His, Gly or Ala

<400> SEQUENCE: 123

Xaa Xaa Xaa Lys Lys
1               5
```

-continued

```
<210> SEQ ID NO 124
<211> LENGTH: 6
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(3)
<223> OTHER INFORMATION: Xaa is Arg, His, Gly or Ala

<400> SEQUENCE: 124

Xaa Xaa Xaa Lys Lys Lys
1               5

<210> SEQ ID NO 125
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (2)..(4)
<223> OTHER INFORMATION: Xaa is Arg, His, Gly or Ala

<400> SEQUENCE: 125

Lys Xaa Xaa Xaa
1

<210> SEQ ID NO 126
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (3)..(4)
<223> OTHER INFORMATION: Xaa is Arg, His, Gly or Ala

<400> SEQUENCE: 126

Lys Lys Xaa Xaa
1

<210> SEQ ID NO 127
<211> LENGTH: 5
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (3)..(5)
<223> OTHER INFORMATION: Xaa is Arg, His, Gly or Ala

<400> SEQUENCE: 127

Lys Lys Xaa Xaa Xaa
1               5

<210> SEQ ID NO 128
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (4)..(4)
<223> OTHER INFORMATION: Xaa is Arg, His, Gly or Ala
```

```
<400> SEQUENCE: 128

Lys Lys Lys Xaa
1

<210> SEQ ID NO 129
<211> LENGTH: 5
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (4)..(5)
<223> OTHER INFORMATION: Xaa is Arg, His, Gly or Ala

<400> SEQUENCE: 129

Lys Lys Lys Xaa Xaa
1               5

<210> SEQ ID NO 130
<211> LENGTH: 6
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (4)..(6)
<223> OTHER INFORMATION: Xaa is Arg, His, Gly or Ala

<400> SEQUENCE: 130

Lys Lys Lys Xaa Xaa Xaa
1               5

<210> SEQ ID NO 131
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(1)
<223> OTHER INFORMATION: Xaa is Arg, His, Gly or Ala
<220> FEATURE:
<221> NAME/KEY: MOD_RES
<222> LOCATION: (3)..(3)
<223> OTHER INFORMATION: Xaa is Arg, His, Gly or Ala

<400> SEQUENCE: 131

Xaa Lys Xaa Lys
1

<210> SEQ ID NO 132
<211> LENGTH: 6
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(1)
<223> OTHER INFORMATION: Xaa is Arg, His, Gly or Ala
<220> FEATURE:
<221> NAME/KEY: MOD_RES
<222> LOCATION: (3)..(3)
<223> OTHER INFORMATION: Xaa is Arg, His, Gly or Ala
<220> FEATURE:
<221> NAME/KEY: MOD_RES
<222> LOCATION: (5)..(5)
<223> OTHER INFORMATION: Xaa is Arg, His, Gly or Ala
```

<400> SEQUENCE: 132

Xaa Lys Xaa Lys Xaa Lys
1               5

<210> SEQ ID NO 133
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (2)..(2)
<223> OTHER INFORMATION: Xaa is Arg, His, Gly or Ala
<220> FEATURE:
<221> NAME/KEY: MOD_RES
<222> LOCATION: (4)..(4)
<223> OTHER INFORMATION: Xaa is Arg, His, Gly or Ala

<400> SEQUENCE: 133

Lys Xaa Lys Xaa
1

<210> SEQ ID NO 134
<211> LENGTH: 6
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (2)..(2)
<223> OTHER INFORMATION: Xaa is Arg, His, Gly or Ala
<220> FEATURE:
<221> NAME/KEY: MOD_RES
<222> LOCATION: (4)..(4)
<223> OTHER INFORMATION: Xaa is Arg, His, Gly or Ala
<220> FEATURE:
<221> NAME/KEY: MOD_RES
<222> LOCATION: (6)..(6)
<223> OTHER INFORMATION: Xaa is Arg, His, Gly or Ala

<400> SEQUENCE: 134

Lys Xaa Lys Xaa Lys Xaa
1               5

<210> SEQ ID NO 135
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(4)
<223> OTHER INFORMATION: Orn

<400> SEQUENCE: 135

Xaa Xaa Xaa Xaa
1

<210> SEQ ID NO 136
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(1)

```
<223> OTHER INFORMATION: Xaa is Arg, His, Gly or Ala
<220> FEATURE:
<221> NAME/KEY: MOD_RES
<222> LOCATION: (2)..(4)
<223> OTHER INFORMATION: Orn

<400> SEQUENCE: 136

Xaa Xaa Xaa Xaa
1

<210> SEQ ID NO 137
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(2)
<223> OTHER INFORMATION: Xaa is Arg, His, Gly or Ala
<220> FEATURE:
<221> NAME/KEY: MOD_RES
<222> LOCATION: (3)..(4)
<223> OTHER INFORMATION: Orn

<400> SEQUENCE: 137

Xaa Xaa Xaa Xaa
1

<210> SEQ ID NO 138
<211> LENGTH: 5
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(2)
<223> OTHER INFORMATION: Xaa is Arg, His, Gly or Ala
<220> FEATURE:
<221> NAME/KEY: MOD_RES
<222> LOCATION: (3)..(5)
<223> OTHER INFORMATION: Orn

<400> SEQUENCE: 138

Xaa Xaa Xaa Xaa Xaa
1               5

<210> SEQ ID NO 139
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(3)
<223> OTHER INFORMATION: Xaa is Arg, His, Gly or Ala
<220> FEATURE:
<221> NAME/KEY: MOD_RES
<222> LOCATION: (4)..(4)
<223> OTHER INFORMATION: Orn

<400> SEQUENCE: 139

Xaa Xaa Xaa Xaa
1

<210> SEQ ID NO 140
<211> LENGTH: 5
<212> TYPE: PRT
<213> ORGANISM: Artificial Sequence
```

```
<220> FEATURE:
<223> OTHER INFORMATION: Synthesized peptide analogue
<220> FEATURE:
<221> NAME/KEY: MOD_RES
<222> LOCATION: (1)..(3)
<223> OTHER INFORMATION: Xaa is Arg, His, Gly or Ala
<220> FEATURE:
<221> NAME/KEY: MOD_RES
<222> LOCATION: (4)..(5)
<223> OTHER INFORMATION: Orn

<400> SEQUENCE: 140

Xaa Xaa Xaa Xaa Xaa
1               5

<210> SEQ ID NO 141
<211> LENGTH: 6
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(3)
<223> OTHER INFORMATION: Xaa is Arg, His, Gly or Ala
<220> FEATURE:
<221> NAME/KEY: MOD_RES
<222> LOCATION: (4)..(6)
<223> OTHER INFORMATION: Orn

<400> SEQUENCE: 141

Xaa Xaa Xaa Xaa Xaa Xaa
1               5

<210> SEQ ID NO 142
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(1)
<223> OTHER INFORMATION: Orn
<220> FEATURE:
<221> NAME/KEY: MOD_RES
<222> LOCATION: (2)..(4)
<223> OTHER INFORMATION: Xaa is Arg, His, Gly or Ala

<400> SEQUENCE: 142

Xaa Xaa Xaa Xaa
1

<210> SEQ ID NO 143
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(2)
<223> OTHER INFORMATION: Orn
<220> FEATURE:
<221> NAME/KEY: MOD_RES
<222> LOCATION: (3)..(4)
<223> OTHER INFORMATION: Xaa is Arg, His, Gly or Ala

<400> SEQUENCE: 143

Xaa Xaa Xaa Xaa
1
```

```
<210> SEQ ID NO 144
<211> LENGTH: 5
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(2)
<223> OTHER INFORMATION: Orn
<220> FEATURE:
<221> NAME/KEY: MOD_RES
<222> LOCATION: (3)..(5)
<223> OTHER INFORMATION: Xaa is Arg, His, Gly or Ala

<400> SEQUENCE: 144

Xaa Xaa Xaa Xaa Xaa
1               5

<210> SEQ ID NO 145
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(3)
<223> OTHER INFORMATION: Orn
<220> FEATURE:
<221> NAME/KEY: MOD_RES
<222> LOCATION: (4)..(4)
<223> OTHER INFORMATION: Xaa is Arg, His, Gly or Ala

<400> SEQUENCE: 145

Xaa Xaa Xaa Xaa
1

<210> SEQ ID NO 146
<211> LENGTH: 5
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(3)
<223> OTHER INFORMATION: Orn
<220> FEATURE:
<221> NAME/KEY: MOD_RES
<222> LOCATION: (4)..(5)
<223> OTHER INFORMATION: Xaa is Arg, His, Gly or Ala

<400> SEQUENCE: 146

Xaa Xaa Xaa Xaa Xaa
1               5

<210> SEQ ID NO 147
<211> LENGTH: 6
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(3)
<223> OTHER INFORMATION: Orn
<220> FEATURE:
<221> NAME/KEY: MOD_RES
<222> LOCATION: (4)..(6)
<223> OTHER INFORMATION: Xaa is Arg, His, Gly or Ala
```

```
<400> SEQUENCE: 147

Xaa Xaa Xaa Xaa Xaa Xaa
1               5

<210> SEQ ID NO 148
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(1)
<223> OTHER INFORMATION: Xaa is Arg, His, Gly or Ala
<220> FEATURE:
<221> NAME/KEY: MOD_RES
<222> LOCATION: (2)..(2)
<223> OTHER INFORMATION: Orn
<220> FEATURE:
<221> NAME/KEY: MOD_RES
<222> LOCATION: (3)..(3)
<223> OTHER INFORMATION: Xaa is Arg, His, Gly or Ala
<220> FEATURE:
<221> NAME/KEY: MOD_RES
<222> LOCATION: (4)..(4)
<223> OTHER INFORMATION: Orn

<400> SEQUENCE: 148

Xaa Xaa Xaa Xaa
1

<210> SEQ ID NO 149
<211> LENGTH: 6
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(1)
<223> OTHER INFORMATION: Xaa is Arg, His, Gly or Ala
<220> FEATURE:
<221> NAME/KEY: MOD_RES
<222> LOCATION: (2)..(2)
<223> OTHER INFORMATION: Orn
<220> FEATURE:
<221> NAME/KEY: MOD_RES
<222> LOCATION: (3)..(3)
<223> OTHER INFORMATION: Xaa is Arg, His, Gly or Ala
<220> FEATURE:
<221> NAME/KEY: MOD_RES
<222> LOCATION: (4)..(4)
<223> OTHER INFORMATION: Orn
<220> FEATURE:
<221> NAME/KEY: MOD_RES
<222> LOCATION: (5)..(5)
<223> OTHER INFORMATION: Xaa is Arg, His, Gly or Ala
<220> FEATURE:
<221> NAME/KEY: MOD_RES
<222> LOCATION: (6)..(6)
<223> OTHER INFORMATION: Orn

<400> SEQUENCE: 149

Xaa Xaa Xaa Xaa Xaa Xaa
1               5

<210> SEQ ID NO 150
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
```

```
<221> NAME/KEY: MOD_RES
<222> LOCATION: (1)..(1)
<223> OTHER INFORMATION: Orn
<220> FEATURE:
<221> NAME/KEY: MOD_RES
<222> LOCATION: (2)..(2)
<223> OTHER INFORMATION: Xaa is Arg, His, Gly or Ala
<220> FEATURE:
<221> NAME/KEY: MOD_RES
<222> LOCATION: (3)..(3)
<223> OTHER INFORMATION: Orn
<220> FEATURE:
<221> NAME/KEY: MOD_RES
<222> LOCATION: (4)..(4)
<223> OTHER INFORMATION: Xaa is Arg, His, Gly or Ala

<400> SEQUENCE: 150

Xaa Xaa Xaa Xaa
1

<210> SEQ ID NO 151
<211> LENGTH: 6
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(1)
<223> OTHER INFORMATION: Orn
<220> FEATURE:
<221> NAME/KEY: MOD_RES
<222> LOCATION: (2)..(2)
<223> OTHER INFORMATION: Xaa is Arg, His, Gly or Ala
<220> FEATURE:
<221> NAME/KEY: MOD_RES
<222> LOCATION: (3)..(3)
<223> OTHER INFORMATION: Orn
<220> FEATURE:
<221> NAME/KEY: MOD_RES
<222> LOCATION: (4)..(4)
<223> OTHER INFORMATION: Xaa is Arg, His, Gly or Ala
<220> FEATURE:
<221> NAME/KEY: MOD_RES
<222> LOCATION: (5)..(5)
<223> OTHER INFORMATION: Orn
<220> FEATURE:
<221> NAME/KEY: MOD_RES
<222> LOCATION: (6)..(6)
<223> OTHER INFORMATION: Xaa is Arg, His, Gly or Ala

<400> SEQUENCE: 151

Xaa Xaa Xaa Xaa Xaa Xaa
1               5

<210> SEQ ID NO 152
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(1)
<223> OTHER INFORMATION: Orn

<400> SEQUENCE: 152

Xaa Lys Lys Lys
1

<210> SEQ ID NO 153
<211> LENGTH: 4
<212> TYPE: PRT
```

```
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(2)
<223> OTHER INFORMATION: Orn

<400> SEQUENCE: 153

Xaa Xaa Lys Lys
1

<210> SEQ ID NO 154
<211> LENGTH: 5
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(2)
<223> OTHER INFORMATION: Orn

<400> SEQUENCE: 154

Xaa Xaa Lys Lys Lys
1               5

<210> SEQ ID NO 155
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(3)
<223> OTHER INFORMATION: Orn

<400> SEQUENCE: 155

Xaa Xaa Xaa Lys
1

<210> SEQ ID NO 156
<211> LENGTH: 5
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(3)
<223> OTHER INFORMATION: Orn

<400> SEQUENCE: 156

Xaa Xaa Xaa Lys Lys
1               5

<210> SEQ ID NO 157
<211> LENGTH: 6
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(3)
<223> OTHER INFORMATION: Orn

<400> SEQUENCE: 157

Xaa Xaa Xaa Lys Lys Lys
```

```
1               5

<210> SEQ ID NO 158
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (2)..(4)
<223> OTHER INFORMATION: Orn

<400> SEQUENCE: 158

Lys Xaa Xaa Xaa
1

<210> SEQ ID NO 159
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (3)..(4)
<223> OTHER INFORMATION: Orn

<400> SEQUENCE: 159

Lys Lys Xaa Xaa
1

<210> SEQ ID NO 160
<211> LENGTH: 5
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (3)..(5)
<223> OTHER INFORMATION: Orn

<400> SEQUENCE: 160

Lys Lys Xaa Xaa Xaa
1               5

<210> SEQ ID NO 161
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (4)..(4)
<223> OTHER INFORMATION: Orn

<400> SEQUENCE: 161

Lys Lys Lys Xaa
1

<210> SEQ ID NO 162
<211> LENGTH: 5
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
```

-continued

<222> LOCATION: (4)..(5)
<223> OTHER INFORMATION: Orn

<400> SEQUENCE: 162

Lys Lys Lys Xaa Xaa
1               5

<210> SEQ ID NO 163
<211> LENGTH: 6
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (4)..(6)
<223> OTHER INFORMATION: Orn

<400> SEQUENCE: 163

Lys Lys Lys Xaa Xaa Xaa
1               5

<210> SEQ ID NO 164
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(1)
<223> OTHER INFORMATION: Orn
<220> FEATURE:
<221> NAME/KEY: MOD_RES
<222> LOCATION: (3)..(3)
<223> OTHER INFORMATION: Orn

<400> SEQUENCE: 164

Xaa Lys Xaa Lys
1

<210> SEQ ID NO 165
<211> LENGTH: 6
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(1)
<223> OTHER INFORMATION: Orn
<220> FEATURE:
<221> NAME/KEY: MOD_RES
<222> LOCATION: (3)..(3)
<223> OTHER INFORMATION: Orn
<220> FEATURE:
<221> NAME/KEY: MOD_RES
<222> LOCATION: (5)..(5)
<223> OTHER INFORMATION: Orn

<400> SEQUENCE: 165

Xaa Lys Xaa Lys Xaa Lys
1               5

<210> SEQ ID NO 166
<211> LENGTH: 4
<212> TYPE: PRT
<213> ORGANISM: Artificial Sequence
<220> FEATURE:
<223> OTHER INFORMATION: Synthesized peptide analogue
<220> FEATURE:

```
<221> NAME/KEY: MOD_RES
<222> LOCATION: (2)..(2)
<223> OTHER INFORMATION: Orn
<220> FEATURE:
<221> NAME/KEY: MOD_RES
<222> LOCATION: (4)..(4)
<223> OTHER INFORMATION: Orn

<400> SEQUENCE: 166

Lys Xaa Lys Xaa
1

<210> SEQ ID NO 167
<211> LENGTH: 6
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (2)..(2)
<223> OTHER INFORMATION: Orn
<220> FEATURE:
<221> NAME/KEY: MOD_RES
<222> LOCATION: (4)..(4)
<223> OTHER INFORMATION: Orn
<220> FEATURE:
<221> NAME/KEY: MOD_RES
<222> LOCATION: (6)..(6)
<223> OTHER INFORMATION: Orn

<400> SEQUENCE: 167

Lys Xaa Lys Xaa Lys Xaa
1               5

<210> SEQ ID NO 168
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(4)
<223> OTHER INFORMATION: Xaa is an amino-alkyl amino acid residue

<400> SEQUENCE: 168

Xaa Xaa Xaa Xaa
1

<210> SEQ ID NO 169
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(1)
<223> OTHER INFORMATION: Xaa is Arg, His, Gly or Ala
<220> FEATURE:
<221> NAME/KEY: MOD_RES
<222> LOCATION: (2)..(4)
<223> OTHER INFORMATION: Xaa is an amino-alkyl amino acid residue

<400> SEQUENCE: 169

Xaa Xaa Xaa Xaa
1

<210> SEQ ID NO 170
<211> LENGTH: 4
```

```
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(2)
<223> OTHER INFORMATION: Xaa is Arg, His, Gly or Ala
<220> FEATURE:
<221> NAME/KEY: MOD_RES
<222> LOCATION: (3)..(4)
<223> OTHER INFORMATION: Xaa is an amino-alkyl amino acid residue

<400> SEQUENCE: 170

Xaa Xaa Xaa Xaa
1

<210> SEQ ID NO 171
<211> LENGTH: 5
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(2)
<223> OTHER INFORMATION: Xaa is Arg, His, Gly or Ala
<220> FEATURE:
<221> NAME/KEY: MOD_RES
<222> LOCATION: (3)..(5)
<223> OTHER INFORMATION: Xaa is an amino-alkyl amino acid residue

<400> SEQUENCE: 171

Xaa Xaa Xaa Xaa Xaa
1               5

<210> SEQ ID NO 172
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(3)
<223> OTHER INFORMATION: Xaa is Arg, His, Gly or Ala
<220> FEATURE:
<221> NAME/KEY: MOD_RES
<222> LOCATION: (4)..(4)
<223> OTHER INFORMATION: Xaa is an amino-alkyl amino acid residue

<400> SEQUENCE: 172

Xaa Xaa Xaa Xaa
1

<210> SEQ ID NO 173
<211> LENGTH: 5
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(3)
<223> OTHER INFORMATION: Xaa is Arg, His, Gly or Ala
<220> FEATURE:
<221> NAME/KEY: MOD_RES
<222> LOCATION: (4)..(5)
<223> OTHER INFORMATION: Xaa is an amino-alkyl amino acid residue

<400> SEQUENCE: 173

Xaa Xaa Xaa Xaa Xaa
```

<210> SEQ ID NO 174
<211> LENGTH: 6
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(3)
<223> OTHER INFORMATION: Xaa is Arg, His, Gly or Ala
<220> FEATURE:
<221> NAME/KEY: MOD_RES
<222> LOCATION: (4)..(6)
<223> OTHER INFORMATION: Xaa is an amino-alkyl amino acid residue

<400> SEQUENCE: 174

Xaa Xaa Xaa Xaa Xaa Xaa
1               5

<210> SEQ ID NO 175
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(1)
<223> OTHER INFORMATION: Xaa is an amino-alkyl amino acid residue
<220> FEATURE:
<221> NAME/KEY: MOD_RES
<222> LOCATION: (2)..(4)
<223> OTHER INFORMATION: Xaa is Arg, His, Gly or Ala

<400> SEQUENCE: 175

Xaa Xaa Xaa Xaa
1

<210> SEQ ID NO 176
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(2)
<223> OTHER INFORMATION: Xaa is an amino-alkyl amino acid residue
<220> FEATURE:
<221> NAME/KEY: MOD_RES
<222> LOCATION: (3)..(4)
<223> OTHER INFORMATION: Xaa is Arg, His, Gly or Ala

<400> SEQUENCE: 176

Xaa Xaa Xaa Xaa
1

<210> SEQ ID NO 177
<211> LENGTH: 5
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(2)
<223> OTHER INFORMATION: Xaa is an amino-alkyl amino acid residue
<220> FEATURE:
<221> NAME/KEY: MOD_RES
<222> LOCATION: (3)..(5)

<223> OTHER INFORMATION: Xaa is Arg, His, Gly or Ala

<400> SEQUENCE: 177

Xaa Xaa Xaa Xaa Xaa
1               5

<210> SEQ ID NO 178
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(3)
<223> OTHER INFORMATION: Xaa is an amino-alkyl amino acid residue
<220> FEATURE:
<221> NAME/KEY: MOD_RES
<222> LOCATION: (4)..(4)
<223> OTHER INFORMATION: Xaa is Arg, His, Gly or Ala

<400> SEQUENCE: 178

Xaa Xaa Xaa Xaa
1

<210> SEQ ID NO 179
<211> LENGTH: 5
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(3)
<223> OTHER INFORMATION: Xaa is an amino-alkyl amino acid residue
<220> FEATURE:
<221> NAME/KEY: MOD_RES
<222> LOCATION: (4)..(5)
<223> OTHER INFORMATION: Xaa is Arg, His, Gly or Ala

<400> SEQUENCE: 179

Xaa Xaa Xaa Xaa Xaa
1               5

<210> SEQ ID NO 180
<211> LENGTH: 6
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(3)
<223> OTHER INFORMATION: Xaa is an amino-alkyl amino acid residue
<220> FEATURE:
<221> NAME/KEY: MOD_RES
<222> LOCATION: (4)..(6)
<223> OTHER INFORMATION: Xaa is Arg, His, Gly or Ala

<400> SEQUENCE: 180

Xaa Xaa Xaa Xaa Xaa Xaa
1               5

<210> SEQ ID NO 181
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES

```
<222> LOCATION: (1)..(1)
<223> OTHER INFORMATION: Xaa is Arg, His, Gly or Ala
<220> FEATURE:
<221> NAME/KEY: MOD_RES
<222> LOCATION: (2)..(2)
<223> OTHER INFORMATION: Xaa is an amino-alkyl amino acid residue
<220> FEATURE:
<221> NAME/KEY: MOD_RES
<222> LOCATION: (3)..(3)
<223> OTHER INFORMATION: Xaa is Arg, His, Gly or Ala
<220> FEATURE:
<221> NAME/KEY: MOD_RES
<222> LOCATION: (4)..(4)
<223> OTHER INFORMATION: Xaa is an amino-alkyl amino acid residue

<400> SEQUENCE: 181

Xaa Xaa Xaa Xaa
1

<210> SEQ ID NO 182
<211> LENGTH: 6
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(1)
<223> OTHER INFORMATION: Xaa is Arg, His, Gly or Ala
<220> FEATURE:
<221> NAME/KEY: MOD_RES
<222> LOCATION: (2)..(2)
<223> OTHER INFORMATION: Xaa is an amino-alkyl amino acid residue
<220> FEATURE:
<221> NAME/KEY: MOD_RES
<222> LOCATION: (3)..(3)
<223> OTHER INFORMATION: Xaa is Arg, His, Gly or Ala
<220> FEATURE:
<221> NAME/KEY: MOD_RES
<222> LOCATION: (4)..(4)
<223> OTHER INFORMATION: Xaa is an amino-alkyl amino acid residue
<220> FEATURE:
<221> NAME/KEY: MOD_RES
<222> LOCATION: (5)..(5)
<223> OTHER INFORMATION: Xaa is Arg, His, Gly or Ala
<220> FEATURE:
<221> NAME/KEY: MOD_RES
<222> LOCATION: (6)..(6)
<223> OTHER INFORMATION: Xaa is an amino-alkyl amino acid residue

<400> SEQUENCE: 182

Xaa Xaa Xaa Xaa Xaa Xaa
1               5

<210> SEQ ID NO 183
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(1)
<223> OTHER INFORMATION: Xaa is an amino-alkyl amino acid residue
<220> FEATURE:
<221> NAME/KEY: MOD_RES
<222> LOCATION: (2)..(2)
<223> OTHER INFORMATION: Xaa is Arg, His, Gly or Ala
<220> FEATURE:
<221> NAME/KEY: MOD_RES
<222> LOCATION: (3)..(3)
<223> OTHER INFORMATION: Xaa is an amino-alkyl amino acid residue
<220> FEATURE:
<221> NAME/KEY: MOD_RES
<222> LOCATION: (4)..(4)
```

<223> OTHER INFORMATION: Xaa is Arg, His, Gly or Ala

<400> SEQUENCE: 183

Xaa Xaa Xaa Xaa
1

<210> SEQ ID NO 184
<211> LENGTH: 6
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(1)
<223> OTHER INFORMATION: Xaa is an amino-alkyl amino acid residue
<220> FEATURE:
<221> NAME/KEY: MOD_RES
<222> LOCATION: (2)..(2)
<223> OTHER INFORMATION: Xaa is Arg, His, Gly or Ala
<220> FEATURE:
<221> NAME/KEY: MOD_RES
<222> LOCATION: (3)..(3)
<223> OTHER INFORMATION: Xaa is an amino-alkyl amino acid residue
<220> FEATURE:
<221> NAME/KEY: MOD_RES
<222> LOCATION: (4)..(4)
<223> OTHER INFORMATION: Xaa is Arg, His, Gly or Ala
<220> FEATURE:
<221> NAME/KEY: MOD_RES
<222> LOCATION: (5)..(5)
<223> OTHER INFORMATION: Xaa is an amino-alkyl amino acid residue
<220> FEATURE:
<221> NAME/KEY: MOD_RES
<222> LOCATION: (6)..(6)
<223> OTHER INFORMATION: Xaa is Arg, His, Gly or Ala

<400> SEQUENCE: 184

Xaa Xaa Xaa Xaa Xaa Xaa
1               5

<210> SEQ ID NO 185
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(4)
<223> OTHER INFORMATION: Xaa is L-lysine, D-lysine, L-ornithine or
      D-ornithine

<400> SEQUENCE: 185

Xaa Xaa Xaa Xaa
1

<210> SEQ ID NO 186
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(1)
<223> OTHER INFORMATION: Xaa is Arg, His, Gly or Ala
<220> FEATURE:
<221> NAME/KEY: MOD_RES
<222> LOCATION: (2)..(4)
<223> OTHER INFORMATION: Xaa is L-lysine, D-lysine, L-ornithine or
      D-ornithine

```
<400> SEQUENCE: 186

Xaa Xaa Xaa Xaa
1

<210> SEQ ID NO 187
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(2)
<223> OTHER INFORMATION: Xaa is Arg, His, Gly or Ala
<220> FEATURE:
<221> NAME/KEY: MOD_RES
<222> LOCATION: (3)..(4)
<223> OTHER INFORMATION: Xaa is L-lysine, D-lysine, L-ornithine or
      D-ornithine

<400> SEQUENCE: 187

Xaa Xaa Xaa Xaa
1

<210> SEQ ID NO 188
<211> LENGTH: 5
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(2)
<223> OTHER INFORMATION: Xaa is Arg, His, Gly or Ala
<220> FEATURE:
<221> NAME/KEY: MOD_RES
<222> LOCATION: (3)..(5)
<223> OTHER INFORMATION: Xaa is L-lysine, D-lysine, L-ornithine or
      D-ornithine

<400> SEQUENCE: 188

Xaa Xaa Xaa Xaa Xaa
1               5

<210> SEQ ID NO 189
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(3)
<223> OTHER INFORMATION: Xaa is Arg, His, Gly or Ala
<220> FEATURE:
<221> NAME/KEY: MOD_RES
<222> LOCATION: (4)..(4)
<223> OTHER INFORMATION: Xaa is L-lysine, D-lysine, L-ornithine or
      D-ornithine

<400> SEQUENCE: 189

Xaa Xaa Xaa Xaa
1

<210> SEQ ID NO 190
<211> LENGTH: 5
<212> TYPE: PRT
<213> ORGANISM: Artificial Sequence
<220> FEATURE:
<223> OTHER INFORMATION: Synthesized peptide analogue
<220> FEATURE:
```

```
<221> NAME/KEY: MOD_RES
<222> LOCATION: (1)..(3)
<223> OTHER INFORMATION: Xaa is Arg, His, Gly or Ala
<220> FEATURE:
<221> NAME/KEY: MOD_RES
<222> LOCATION: (4)..(5)
<223> OTHER INFORMATION: Xaa is L-lysine, D-lysine, L-ornithine or
      D-ornithine

<400> SEQUENCE: 190

Xaa Xaa Xaa Xaa Xaa
1               5

<210> SEQ ID NO 191
<211> LENGTH: 6
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(3)
<223> OTHER INFORMATION: Xaa is Arg, His, Gly or Ala
<220> FEATURE:
<221> NAME/KEY: MOD_RES
<222> LOCATION: (4)..(6)
<223> OTHER INFORMATION: Xaa is L-lysine, D-lysine, L-ornithine or
      D-ornithine

<400> SEQUENCE: 191

Xaa Xaa Xaa Xaa Xaa Xaa
1               5

<210> SEQ ID NO 192
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(1)
<223> OTHER INFORMATION: Xaa is L-lysine, D-lysine, L-ornithine or
      D-ornithine
<220> FEATURE:
<221> NAME/KEY: MOD_RES
<222> LOCATION: (2)..(4)
<223> OTHER INFORMATION: Xaa is Arg, His, Gly or Ala

<400> SEQUENCE: 192

Xaa Xaa Xaa Xaa
1

<210> SEQ ID NO 193
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(2)
<223> OTHER INFORMATION: Xaa is L-lysine, D-lysine, L-ornithine or
      D-ornithine
<220> FEATURE:
<221> NAME/KEY: MOD_RES
<222> LOCATION: (3)..(4)
<223> OTHER INFORMATION: Xaa is Arg, His, Gly or Ala

<400> SEQUENCE: 193

Xaa Xaa Xaa Xaa
1
```

```
<210> SEQ ID NO 194
<211> LENGTH: 5
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(2)
<223> OTHER INFORMATION: Xaa is an amino-alkyl amino acid residue
<220> FEATURE:
<221> NAME/KEY: MOD_RES
<222> LOCATION: (1)..(2)
<223> OTHER INFORMATION: Xaa is L-lysine, D-lysine, L-ornithine or
      D-ornithine
<220> FEATURE:
<221> NAME/KEY: MOD_RES
<222> LOCATION: (3)..(5)
<223> OTHER INFORMATION: Xaa is Arg, His, Gly or Ala

<400> SEQUENCE: 194

Xaa Xaa Xaa Xaa Xaa
1               5

<210> SEQ ID NO 195
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(3)
<223> OTHER INFORMATION: Xaa is L-lysine, D-lysine, L-ornithine or
      D-ornithine
<220> FEATURE:
<221> NAME/KEY: MOD_RES
<222> LOCATION: (4)..(4)
<223> OTHER INFORMATION: Xaa is Arg, His, Gly or Ala

<400> SEQUENCE: 195

Xaa Xaa Xaa Xaa
1

<210> SEQ ID NO 196
<211> LENGTH: 5
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(3)
<223> OTHER INFORMATION: Xaa is L-lysine, D-lysine, L-ornithine or
      D-ornithine
<220> FEATURE:
<221> NAME/KEY: MOD_RES
<222> LOCATION: (4)..(5)
<223> OTHER INFORMATION: Xaa is Arg, His, Gly or Ala

<400> SEQUENCE: 196

Xaa Xaa Xaa Xaa Xaa
1               5

<210> SEQ ID NO 197
<211> LENGTH: 6
<212> TYPE: PRT
<213> ORGANISM: Artificial Sequence
<220> FEATURE:
<223> OTHER INFORMATION: Synthesized peptide analogue
<220> FEATURE:
```

```
<221> NAME/KEY: MOD_RES
<222> LOCATION: (1)..(3)
<223> OTHER INFORMATION: Xaa is L-lysine, D-lysine, L-ornithine or
      D-ornithine
<220> FEATURE:
<221> NAME/KEY: MOD_RES
<222> LOCATION: (4)..(6)
<223> OTHER INFORMATION: Xaa is Arg, His, Gly or Ala

<400> SEQUENCE: 197

Xaa Xaa Xaa Xaa Xaa Xaa
1               5

<210> SEQ ID NO 198
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(1)
<223> OTHER INFORMATION: Xaa is Arg, His, Gly or Ala
<220> FEATURE:
<221> NAME/KEY: MOD_RES
<222> LOCATION: (2)..(2)
<223> OTHER INFORMATION: Xaa is L-lysine, D-lysine, L-ornithine or
      D-ornithine
<220> FEATURE:
<221> NAME/KEY: MOD_RES
<222> LOCATION: (3)..(3)
<223> OTHER INFORMATION: Xaa is Arg, His, Gly or Ala
<220> FEATURE:
<221> NAME/KEY: MOD_RES
<222> LOCATION: (4)..(4)
<223> OTHER INFORMATION: Xaa is L-lysine, D-lysine, L-ornithine or
      D-ornithine

<400> SEQUENCE: 198

Xaa Xaa Xaa Xaa
1

<210> SEQ ID NO 199
<211> LENGTH: 6
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(1)
<223> OTHER INFORMATION: Xaa is Arg, His, Gly or Ala
<220> FEATURE:
<221> NAME/KEY: MOD_RES
<222> LOCATION: (2)..(2)
<223> OTHER INFORMATION: Xaa is L-lysine, D-lysine, L-ornithine or
      D-ornithine
<220> FEATURE:
<221> NAME/KEY: MOD_RES
<222> LOCATION: (3)..(3)
<223> OTHER INFORMATION: Xaa is Arg, His, Gly or Ala
<220> FEATURE:
<221> NAME/KEY: MOD_RES
<222> LOCATION: (4)..(4)
<223> OTHER INFORMATION: Xaa is L-lysine, D-lysine, L-ornithine or
      D-ornithine
<220> FEATURE:
<221> NAME/KEY: MOD_RES
<222> LOCATION: (5)..(5)
<223> OTHER INFORMATION: Xaa is Arg, His, Gly or Ala
<220> FEATURE:
<221> NAME/KEY: MOD_RES
<222> LOCATION: (6)..(6)
<223> OTHER INFORMATION: Xaa is L-lysine, D-lysine, L-ornithine or
      D-ornithine
```

```
<400> SEQUENCE: 199

Xaa Xaa Xaa Xaa Xaa Xaa
1               5

<210> SEQ ID NO 200
<211> LENGTH: 4
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(1)
<223> OTHER INFORMATION: Xaa is L-lysine, D-lysine, L-ornithine or
      D-ornithine
<220> FEATURE:
<221> NAME/KEY: MOD_RES
<222> LOCATION: (2)..(2)
<223> OTHER INFORMATION: Xaa is Arg, His, Gly or Ala
<220> FEATURE:
<221> NAME/KEY: MOD_RES
<222> LOCATION: (3)..(3)
<223> OTHER INFORMATION: Xaa is L-lysine, D-lysine, L-ornithine or
      D-ornithine
<220> FEATURE:
<221> NAME/KEY: MOD_RES
<222> LOCATION: (4)..(4)
<223> OTHER INFORMATION: Xaa is Arg, His, Gly or Ala

<400> SEQUENCE: 200

Xaa Xaa Xaa Xaa
1

<210> SEQ ID NO 201
<211> LENGTH: 6
<212> TYPE: PRT
<213> ORGANISM: Artificial Sequence
<220> FEATURE:
<223> OTHER INFORMATION: Synthesized peptide analogue
<220> FEATURE:
<221> NAME/KEY: MOD_RES
<222> LOCATION: (1)..(1)
<223> OTHER INFORMATION: Xaa is L-lysine, D-lysine, L-ornithine or
      D-ornithine
<220> FEATURE:
<221> NAME/KEY: MOD_RES
<222> LOCATION: (2)..(2)
<223> OTHER INFORMATION: Xaa is Arg, His, Gly or Ala
<220> FEATURE:
<221> NAME/KEY: MOD_RES
<222> LOCATION: (3)..(3)
<223> OTHER INFORMATION: Xaa is L-lysine, D-lysine, L-ornithine or
      D-ornithine
<220> FEATURE:
<221> NAME/KEY: MOD_RES
<222> LOCATION: (4)..(4)
<223> OTHER INFORMATION: Xaa is Arg, His, Gly or Ala
<220> FEATURE:
<221> NAME/KEY: MOD_RES
<222> LOCATION: (5)..(5)
<223> OTHER INFORMATION: Xaa is L-lysine, D-lysine, L-ornithine or
      D-ornithine
<220> FEATURE:
<221> NAME/KEY: MOD_RES
<222> LOCATION: (6)..(6)
<223> OTHER INFORMATION: Xaa is Arg, His, Gly or Ala

<400> SEQUENCE: 201

Xaa Xaa Xaa Xaa Xaa Xaa
1               5
```

PEPTIDE ANALOGUES WITH BRANCHED AMINO ACID PROBE(S)

CROSS-REFERENCE

This application is a divisional of U.S. application Ser. No. 14/693,810, filed Apr. 22, 2015, now issued as U.S. Pat. No. 9,950,027, which application claims the benefit of U.S. Provisional Application No. 61/982,709, filed Apr. 22, 2014, which are herein incorporated by reference in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is TXPP_001_02US_ST25.txt. The text file is 68 KB, was created on May 4, 2021, and is being submitted electronically via EFS-Web.

FIELD OF INVENTION

The present invention relates to branched amino acid probes which are added to native peptides, or variants of said peptides, to produce peptide analogues or conjugates comprising a peptide and one or more branched amino acid probes.

BACKGROUND OF THE INVENTION

Proteins and peptides are widely employed for therapeutic purposes whether in their native forms, variant forms or analogues thereof. Protein therapeutics tend to be specific for their targets, leading to potentially fewer side effects, but often with lower bioavailability, poorer membrane permeability, and metabolic instability, as compared to small molecules. Protein-based drugs are generally referred to as 'biologics' and include molecules such as insulin, growth factors, and engineered antibodies.

Proteinaceous molecules typically require injection; nevertheless, biologics have been an extremely successful class of therapeutics including antibodies for treatment of arthritis and various cancers, soluble proteins for diabetes, myelosuppression and renal anemia; as well as short injectable peptides for multiple sclerosis, cancers, endometriosis and fibroids and acromegaly.

Peptides represent a class of molecules that have the specificity and potency of larger protein biologics, but are smaller in size and more accessible and cheaper to manufacture using chemical methods, thus potentially combining some of the advantages of proteins with those of small molecules.

Protein and peptide compounds can be modified in various ways in order to improve one or more features of the compound, or address one or more potential draw-backs of the compound. For example, a stabilizing peptide sequence may be added to the N- and/or C-terminus of pharmacologically active peptides potentially making them less susceptible to degradation (WO 99/46283). Further, a linear amino acid probe of 6 amino acids selected from Lys or Glu added to the N-terminus of α-MSH potentially increases efficacy compared to the native peptide (WO 07/22774). Known peptide-drug conjugates further include addition of polycationic peptides CPP (cell-penetrating peptides) to improve transport across the cell lipid bi-layer.

SUMMARY OF THE INVENTION

The present invention provides peptide analogues comprising a peptide or protein, native or naturally occurring, or biologically active variants thereof, and one or more branched amino acid probes (abbreviated BAP herein). Modification of peptides by addition of one or more branched amino acid probes has not previously been disclosed.

In some embodiments, the peptide analogues provided herein have one or more improved properties compared to the native peptide. For example, in some embodiments, addition of one or more branched amino acid probes to a peptide potentially improves one or more features of the peptide, such as

- improve or increase an inherent effect of the peptide (including for example increasing the activity, affinity and/or efficacy of a pharmacologically active peptide; improved binding to and/or activation of one or more relevant receptors);
- alter an inherent effect of the peptide (including for example an altered receptor binding profile), or
- improve or alter an external effect of the peptide (including for example increased stability, reduced degradation, altered configuration and/or altered solubility).

Thus, the present invention relates to a peptide analogue comprising a peptide and one or more branched amino acid probes, wherein said branched amino acid probe comprises a first amino-alkyl amino acid residue, said first amino-alkyl amino acid residue optionally being covalently linked to a second amino-alkyl amino acid residue, or to a second and a third amino-alkyl amino acid residue, to form a linear chain of 2 or 3 amino-alkyl amino acid residues, wherein the side chain(s) of one or more of said first, second and/or third amino-alkyl amino acid residues are each modified by attaching to the side chain amino group a molecule independently selected from the group consisting of $AAA_q$-AAA (SEQ ID NO: 168); $(aa_3)_p$-$AAA_q$ (SEQ ID NOs: 169-174); $AAA_q$-$(aa_3)_p$ (SEQ ID NOs: 175-180); $[(aa_3)$-$AAA]_p$ (SEQ ID NOs: 181 and 182) and $[AAA$-$(aa_3)]p$ (SEQ ID NOs: 183 and 184);

wherein q is a number selected from 0, 1, 2 and 3; p is a number selected from 1, 2 and 3; AAA is an amino-alkyl amino acid residue; and $(aa_3)$ is an amino acid residue independently selected from Arg, His, Gly and Ala, wherein said amino-alkyl amino acid residues are optionally acetylated, wherein said first amino-alkyl amino acid residue is covalently linked to the N-terminus of said peptide, covalently linked to the C-terminus of said peptide, and/or attached to the side chain amino group of an amino-alkyl amino acid residue within said peptide, with the proviso that said branched amino acid probe consists of 2 to 9 amino acid residues.

The present invention also encompasses pharmaceutical compositions comprising the peptide analogues of the present invention, as well as the analogues of the present invention for use as a medicament.

DESCRIPTION OF DRAWINGS

FIG. 1: Schematic representation of the branched amino acid probe Ac-(Ac-Lys-Lys)Lys-, showing the first amino-alkyl amino acid residue being a lysine residue ($Lys_1$)

attached to the N-terminus of a peptide sequence via a regular peptide bond, said first lysine being acetylated (COCH$_3$), and said first lysine modified by attaching to the ε-amino group of said first lysine residue two further lysine residues wherein one is also acetylated (the outermost).

DETAILED DESCRIPTION OF THE INVENTION

Peptide Analogues

It is an aspect of the present invention to provide peptide analogues modified by addition of one or more branched amino acid probes. The peptide analogues may comprise any peptide, polypeptide or protein, native or naturally occurring, or biologically active variants or fragments thereof, which are modified by addition of one or more branched amino acid probes (abbreviated BAP herein). Thus in one embodiment the peptide analogues are conjugates comprising a peptide sequence and one or more branched amino acid probes.

The terms 'peptide analogue' and 'protein analogue' may be used interchangeably herein. The terms 'peptide' and 'protein' may be used interchangeably herein. The terms 'peptide' and 'peptide sequence' may be used interchangeably herein. The terms 'peptide sequence' and 'amino acid sequence' may be used interchangeably herein.

In some embodiments, the peptide analogues provided herein have certain improved properties, for instance with respect to binding affinity and/or activation of one or more receptors. Still further, in another embodiment, the peptide analogues provided herein are more stable, such as less susceptible to proteases.

It is an aspect of the present invention to provide a peptide analogue comprising a peptide and one or more branched amino acid probes, wherein said branched amino acid probe comprises a first amino-alkyl amino acid residue, said first amino-alkyl amino acid residue optionally being covalently linked to a second amino-alkyl amino acid residue, or to a second and a third amino-alkyl amino acid residue, to form a linear chain of 2 or 3 amino-alkyl amino acid residues, wherein the side chain(s) of one or more of said first, second and/or third amino-alkyl amino acid residues are each modified by attaching to the side chain amino group a molecule independently selected from the group consisting of AAA$_q$-AAA (SEQ ID NO: 168); (aa$_3$)$_p$-AAA$_q$ (SEQ ID NOs: 169-174); AAA$_q$-(aa$_3$)$_p$ (SEQ ID NOs: 175-180); [(aa$_3$)-AAA]$_p$ (SEQ ID NOs: 181 and 182) and [AAA-(aa$_3$)]p (SEQ ID NOs: 183 and 184);

wherein q is a number selected from 0, 1, 2 and 3; p is a number selected from 1, 2 and 3; AAA is an amino-alkyl amino acid residue; and (aa$_3$) is an amino acid residue independently selected from Arg, His, Gly and Ala, wherein said amino-alkyl amino acid residues are optionally acetylated, wherein said first amino-alkyl amino acid residue is covalently linked to the N-terminus of said peptide, covalently linked to the C-terminus of said peptide, and/or attached to the side chain amino group of an amino-alkyl amino acid residue within said peptide, with the proviso that said branched amino acid probe consists of 2 to 9 amino acid residues.

According to the invention an amino-alkyl amino acid residue being covalently linked to further amino-alkyl amino acid residues and/or a peptide in one embodiment means that a peptide bond is present. In one embodiment, covalently linked means covalently linked by (a) peptide bond(s). In one embodiment, covalently linked implies that (a) peptide bond(s) is present.

A peptide bond (amide bond) is a covalent chemical bond formed between two molecules when the carboxyl group of one molecule reacts with the amino group of the other molecule, causing the release of a molecule of H$_2$O. The process usually occurs between amino acids.

The amino-alkyl amino acid residues (or AAA) according to the invention may each be the same (identical) or different (non-identical).

Branched Amino Acid Probe

Amino-Alkyl Amino Acid Residue

According to the present invention an 'amino-alkyl amino acid residue' (or AAA) is an amino acid having the conventional amine (—NH$_2$) and carboxylic acid (—COOH) functional groups, and a side chain attached to the first (alpha-) carbon atom, wherein the side-chain comprises an alkyl group (—C$_n$H$_{2n+1}$) and an amino group (NH$_2$); in one embodiment the side chain comprises an amino-alkyl group (—C$_n$H$_{2n}$NH$_2$).

Thus an amino-alkyl amino acid residue (or AAA) is an amino acid with a side chain comprising or consisting of an amino-alkyl group (—C$_n$H$_{2n}$NH$_2$), in one embodiment denoted a side chain amino-alkyl group.

In one embodiment the side chain alkyl group is derived from the group consisting of methyl (CH$_3$—), ethyl (C$_2$H$_5$—), propyl (C$_3$H$_7$—), butyl (C$_4$H$_9$—), pentyl (C$_5$H$_{11}$—), hexyl (C$_6$H$_{13}$—), heptyl (C$_7$H$_{15}$—), octyl (C$_8$H$_{17}$—), nonyl (C$_9$H$_{19}$—), decyl (C$_{10}$H$_{21}$—), undecyl (C$_{11}$H$_{23}$—) and dodecyl (C$_{12}$H$_{25}$—).

In one embodiment the side chain amino group (NH$_2$) of said amino-alkyl amino acid residue is the amine of methylamine, the amine of ethylamine, the amine of propylamine, the amine of n-butylamine, the amine of pentylamine, the amine of n-hexylamine, the amine of heptylamine, the amine of octylamine, the amine of nonylamine, the amine of decylamine, the amine of undecylamine or the amine of dodecylamine.

In one embodiment the side chain amino-alkyl group according to the invention is selected from the group consisting of methylamine (—CH$_2$NH$_2$), ethylamine (—C$_2$H$_4$NH$_2$), propylamine (—C$_3$H$_6$NH$_2$), n-butylamine (—C$_4$H$_8$NH$_2$), pentylamine (—C$_5$H$_{10}$NH$_2$), n-hexylamine (—C$_6$H$_{12}$NH$_2$), heptylamine (—C$_7$H$_{14}$NH$_2$), octylamine (—C$_8$H$_{16}$NH$_2$), nonylamine (—C$_9$H$_{18}$NH$_2$), decylamine (—C$_{10}$H$_{20}$NH$_2$), undecylamine (—C$_{11}$H$_{22}$NH$_2$) and dodecylamine (—C$_{12}$H$_{24}$NH$_2$).

In one embodiment the side chain amino group (NH$_2$) of said first, second and/or third amino-alkyl amino acid residues are each modified by attaching a molecule thereto.

In one embodiment the side chain amino group of said amino-alkyl amino acid residue is selected from the group consisting of the β (beta) amino group (1 methylene in the side chain; methylamine);

the γ (gamma) amino group (2 methylenes in the side chain, ethylamine);

the δ (delta) amino group (3 methylenes in the side chain, propylamine); =ornithine the ε (epsilon) amino group (4 methylenes in the side chain; n-butylamine); =lysine the ζ (zeta) amino group (5 methylenes in the side chain; pentylamine);

the η (eta) amino group (6 methylenes in the side chain; n-hexylamine);

the θ (theta) amino group (7 methylenes in the side chain; heptylamine);

the ι (iota) amino group (8 methylenes in the side chain; octylamine);

the κ (kappa) amino group (9 methylenes in the side chain; nonylamine);

the λ (lambda) amino group (10 methylenes in the side chain; decylamine);

the μ (mu) amino group (11 methylenes in the side chain; undecylamine); and the ν (nu) amino group (12 methylenes in the side chain; dodecylamine).

For example, the ε-amino group is attached to the fifth carbon beginning from (including) the α-carbon, which α-carbon is attached to the carboxyl (C=OOH) group.

An amino-alkyl amino acid residue wherein the side chain is n-butylamine and the side chain amino group is the ε (epsilon) amino group is lysine (Lys, K).

Likewise, the δ-amino group is attached to the fourth carbon beginning from the α-carbon.

An amino-alkyl amino acid residue wherein the side chain is propylamine and the side chain amino group is the δ (delta) amino group is ornithine (Orn).

Ornithine is formed in cells by deguanidation of arginine. While it is not used in proteinogenesis in vivo it is a participant in several enzyme pathways and appears to play a role in nitrogen balance in vivo as it can be gaunidated enzymatically to form arginine.

Any amino acid according to the present invention may be in the L- or D-configuration. If nothing is specified, reference to the L-isomeric form is preferably meant.

It follows that the amino-alkyl amino acid residues of the invention in one embodiment are individually in the L- or D-configuration. In one embodiment the amino-alkyl amino acid residues are in the L- configuration.

In one embodiment the amino-alkyl amino acid residues of the invention are individually selected from the group consisting of lysine and ornithine.

In one embodiment the amino-alkyl amino acid residues of the invention are individually selected from the group consisting of L-lysine, D-lysine, L-ornithine and D-ornithine.

In one embodiment the amino-alkyl amino acid residues of the invention are selected from the group consisting of L-lysine and L-ornithine.

In one embodiment the amino-alkyl amino acid residues of the invention are selected from the group consisting of L-lysine and D-lysine.

In one embodiment the amino-alkyl amino acid residues of the invention are selected from the group consisting L-ornithine and D-ornithine.

In one embodiment there is provided a peptide analogue comprising a peptide and one or more branched amino acid probes, wherein said branched amino acid probe comprises a first amino acid residue selected from lysine and ornithine, said first amino acid residue optionally being covalently linked to a second, or to a second and a third amino acid residue selected from lysine or ornithine, to form a linear chain of 2 or 3 lysine or ornithine residues, wherein the side chain(s) of one or more of said first, second and/or third lysine or ornithine residues are modified by attaching to the δ-amino group (ornithine) or the ε-amino group a molecule independently selected from the group consisting of $Lys_q$-Lys (SEQ ID NO: 117); $(aa_3)_p$-$Lys_q$ (SEQ ID NOs: 119-124); $Lys_q$-$(aa_3)_p$ (SEQ ID NOs: 125-130); $[(aa_3)$-Lys$]_p$ (SEQ ID NOs: 131 and 132); $[Lys$-$(aa_3)]_p$ (SEQ ID NOs: 133 and 134); $Orn_q$-Orn (SEQ ID NO: 135); $(aa_3)_p$-$Orn_q$ (SEQ ID NOs: 136-141); $Orn_q$-$(aa_3)_p$ (SEQ ID NOs: 142-147); $[(aa_3)$-Orn$]_p$ (SEQ ID NOs: 148 and 149) and $[Orn$-$(aa_3)]_p$ (SEQ ID NOs: 150 and 151); $Orn_p$-$Lys_p$ (SEQ ID NOs: 152-157); $Lys_p$-$Orn_p$ (SEQ ID NOs: 158-163); $[Orn$-Lys$]_p$ (SEQ ID NOs: 164 and 165) and $[Lys$-Orn$]_p$ (SEQ ID NOs: 166 and 167);

wherein q is a number selected from 0, 1, 2 and 3; p is a number selected from 1, 2 and 3; and $(aa_3)$ is an amino acid residue independently selected from Arg, His, Gly and Ala, wherein said lysine and ornithine residues are optionally acetylated, wherein said lysine and ornithine residues are in the L- or D-configuration, wherein said first lysine or ornithine residue is covalently linked to the N-terminus of said peptide, covalently linked to the C-terminus of said peptide, and/or attached to the ε-amino group of a lysine residue or the δ-amino group of an ornithine residue within said peptide, with the proviso that said branched amino acid probe consists of 2 to 9 amino acid residues.

In one embodiment there is provided a peptide analogue comprising a peptide and one or more branched amino acid probes, wherein said branched amino acid probe comprises a first lysine residue, said first lysine residue optionally being covalently linked to a second, or to a second and a third lysine residue, to form a linear chain of 2 or 3 lysine residues, wherein the side chain(s) of one or more of said first, second and/or third lysine residues are modified by attaching to the ε-amino group a molecule independently selected from the group consisting of $Lys_q$-Lys (SEQ ID NO: 117); $(aa_3)_p$-$Lys_q$ ((SEQ ID NOs: 119-124); $Lys_q$-$(aa_3)_p$ (SEQ ID NOs: 125-130); $[(aa_3)$-Lys$]_p$ (SEQ ID NOs: 131 and 132); $[Lys$-$(aa_3)]_p$ (SEQ ID NOs: 133 and 134); wherein q is a number selected from 0, 1, 2 and 3; p is a number selected from 1, 2 and 3; and $(aa_3)$ is an amino acid residue independently selected from Arg, His, Gly and Ala, wherein said lysine residues are optionally acetylated, wherein said lysine residues are in the L- or D-configuration, wherein said first lysine residue is covalently linked to the N-terminus of said peptide, covalently linked to the C-terminus of said peptide, and/or attached to the ε-amino group of a lysine residue within said peptide, with the proviso that said branched amino acid probe consists of 2 to 9 amino acid residues.

Branching the Probe

A branched amino acid probe according to the present invention in one embodiment consists of 2 to 9 amino acid residues.

In one embodiment the branched amino acid probe consist of from 2 to 3 amino acid residues, such as from 3 to 4 amino acid residues, for example from 4 to 5 amino acid residues, such as from 5 to 6 amino acid residues, for example from 6 to 7 amino acid residues, such as from 7 to 8 amino acid residues, for example from 8 to 9 amino acid residues.

In one embodiment the branched amino acid probe consist of 2 amino acid residues, such as 3 amino acid residues, for example 4 amino acid residues, such as 5 amino acid residues, for example 6 amino acid residues, such as 7 amino acid residues, for example 8 amino acid residues, such as 9 amino acid residues.

In one embodiment the branched amino acid probe comprises a first amino-alkyl amino acid residue (also denoted $AAA_1$), which first amino-alkyl amino acid residue is connected to a peptide to provide a peptide analogue according to the invention.

In one embodiment the first amino-alkyl amino acid of (each of) the one or more branched amino acid probe(s) is (are) covalently linked to the N-terminus of said peptide, covalently linked to the C-terminus of said peptide, and/or attached to the side chain amino group of an amino-alkyl amino acid residue within said peptide.

In one embodiment the first amino-alkyl amino acid of the branched amino acid probe is acetylated.

In one embodiment said first amino-alkyl amino acid residue is covalently linked to a second amino-alkyl amino acid residue to form a linear chain of 2 amino-alkyl amino acid residues.

In one embodiment the second amino-alkyl amino acid of the branched amino acid probe is acetylated.

In one embodiment said first amino-alkyl amino acid residue is covalently linked to a second and (covalently linked to) a third amino-alkyl amino acid residue to form a linear chain of 3 amino-alkyl amino acid residues. In this setting, it is understood that the first amino-alkyl amino acid residue may have the second and third amino-alkyl amino acid residues both attached at its amine group or both attached to its carboxylic acid group; or it may have the second amino-alkyl amino acid residue attached at its amine group and the third amino-alkyl amino acid residue attached at its carboxylic acid group.

In one embodiment the third amino-alkyl amino acid of the branched amino acid probe is acetylated.

The second and third amino-alkyl amino acid residues may be denoted $AAA_2$ and $AAA_3$, respectively.

In one embodiment each of said first, second and/or third amino-alkyl amino acid residues is an amino acid having a side chain amino-alkyl group selected from the group consisting of methylamine (—$CH_2NH_2$), ethylamine (—$C_2H_4NH_2$), propylamine (—$C_3H_6NH_2$), n-butylamine (—$C_4H_8NH_2$), pentylamine (—$C_5H_{10}NH_2$), n-hexylamine (—$C_6H_{12}NH_2$), heptylamine (—$C_7H_{14}NH_2$), octylamine (—$C_8H_{16}NH_2$), nonylamine (—$C_9H_{18}NH_2$), decylamine (—$C_{10}H_{20}NH_2$), undecylamine (—$C_{11}H_{22}NH_2$) and dodecylamine (—$C_{12}H_{24}NH_2$).

In one embodiment each of the first, second and/or third amino-alkyl amino acids of the branched amino acid probe are individually selected from the group consisting of L-lysine, D-lysine, L-ornithine and D-ornithine.

In one embodiment each of the first, second and third amino-alkyl amino acids of the branched amino acid probe are lysine residues (including L-lysine and D-lysine).

In one embodiment each of the first, second and third amino-alkyl amino acids of the branched amino acid probe are acetylated (Ac-AAA) ($COCH_3$).

In one embodiment, the first, the first and second, and/or the first, second and third amino-alkyl amino acid residues of the branched amino acid probe are referred to as the amino-alkyl amino acid backbone of the branched amino acid probe ($AAA_1$, $AAA_{1-2}$, $AAA_{1-3}$).

In one embodiment the first, second and third amino-alkyl amino acid residues are lysine residues. In one embodiment the first, the first and second, and/or the first, second and third lysine residues of the branched amino acid probe are referred to as the lysine backbone of the branched amino acid probe ($Lys_1$, $Lys_{1-2}$, $Lys_{1-3}$).

In one embodiment the first lysine residue, or the second lysine residue, or the third lysine residue, or the first and the second lysine residues, or the first and the third lysine residues, or the second and the third lysine residues, or the first, the second and the third lysine residues of the lysine backbone of the branched amino acid probe are acetylated (Ac-Lys).

In one embodiment each of the first, second and third lysine residues of the branched amino acid probe are acetylated (Ac-Lys).

In one embodiment the side chain(s) of one or more of each of said first, second and/or third amino-alkyl amino acid residues are modified by attaching to the side chain amino group a molecule independently selected from the group consisting of $AAA_q$-AAA (SEQ ID NO: 168); $(aa_3)_p$-$AAA_q$ (SEQ ID NOs: 169-174); $AAA_q$-$(aa_3)_p$ (SEQ ID NOs: 175-180); $[(aa_3)$-AAA$]_p$ (SEQ ID NOs: 181 and 182) and $[AAA$-$(aa_3)]_p$ (SEQ ID NOs: 183 and 184); wherein q is a number selected from 0, 1, 2 and 3; p is a number selected from 1, 2 and 3; AAA is an amino-alkyl amino acid residue; and ($aa_3$) is an amino acid residue independently selected from Arg, His, Gly and Ala.

In one embodiment the side chain(s) of one or more of each of said first, second and/or third amino-alkyl amino acid residues are modified by attaching to the side chain amino group a molecule independently selected from the group consisting of $Lys_q$-Lys (SEQ ID NO: 117); $(aa_3)_p$-$Lys_q$ (SEQ ID NOs: 119-124); $Lys_q$-$(aa_3)_p$ (SEQ ID NOs: 125-130); $[(aa_3)$-Lys$]_p$ (SEQ ID NOs: 131 and 132); $[Lys$-$(aa_3)]_p$ (SEQ ID NOs: 133 and 134); $Orn_q$-Orn (SEQ ID NO:135); $(aa_3)_p$-$Orn_q$ (SEQ ID NOs: 136-141); $Orn_q$-$(aa_3)_p$ (SEQ ID NOs: 142-147); $[(aa_3)$-Orn$]_p$ (SEQ ID NOs: 148 and 149) and $[Orn$-$(aa_3)]_p$ (SEQ ID NOs: 150 and 151); $Orn_p$-$Lys_p$ (SEQ ID NOs: 152-157); $Lys_p$-$Orn_p$ (SEQ ID NOs: 158-163); $[Orn$-Lys$]_p$ (SEQ ID NOs: 164 and 165) and $[Lys$-Orn$]_p$ (SEQ ID NOs: 166 and 167);
wherein q is a number selected from 0, 1, 2 and 3; p is a number selected from 1, 2 and 3; and ($aa_3$) is an amino acid residue independently selected from Arg, His, Gly and Ala.

In one embodiment the side chain(s) of one or more of each of said first, second and/or third amino-alkyl amino acid residues are modified by attaching to the side chain amino group a molecule independently selected from the group consisting of $Lys_q$-Lys (SEQ ID NO: 117); $(aa_3)_p$-$Lys_q$ (SEQ ID NOs: 119-124); $Lys_q$-$(aa_3)_p$ (SEQ ID NOs: 125-130); $[(aa_3)$-Lys$]_p$ (SEQ ID NOs: 131 and 132) and $[Lys$-$(aa_3)]_p$ (SEQ ID NOs: 133 and 134); wherein q is a number selected from 0, 1, 2 and 3; p is a number selected from 1, 2 and 3; Lys is a lysine residue selected from L-Lys and D-Lys; and ($aa_3$) is an amino acid residue independently selected from Arg, His, Gly and Ala.

In one embodiment the side chain(s) of one or more of each of said first, second and/or third lysine residues of the lysine backbone are modified by attaching to the ε-amino group of the side chain a molecule independently selected from the group consisting of $Lys_q$-Lys (SEQ ID NO: 117); $(aa_3)_p$-$Lys_q$ (SEQ ID NOs: 119-124); $Lys_q$-$(aa_3)_p$ (SEQ ID NOs: 125-130); $[(aa_3)$-Lys$]_p$ (SEQ ID NOs: 131 and 132) and $[Lys$-$(aa_3)]_p$ (SEQ ID NOs: 133 and 134); wherein q is a number selected from 0, 1, 2 and 3; p is a number selected from 1, 2 and 3; Lys is a lysine residue selected from L-Lys and D-Lys; and ($aa_3$) is an amino acid residue independently selected from Arg, His, Gly and Ala.

In one embodiment the side chain(s) of one or more of each of said first, second and/or third lysine residues of the lysine backbone are modified by attaching to the ε-amino group of the side chain a molecule being $Lys_q$-Lys (SEQ ID NO: 117); wherein q is a number selected from 0, 1, 2 and 3 and Lys is a lysine residue selected from L-Lys and D-Lys.

In one embodiment the side chain of i) one of said first, second and/or third amino-alkyl amino acid residues, ii) two of said first, second and/or third amino-alkyl amino acid residues, or iii) all three of the first, second and third amino-alkyl amino acid residues, are modified by attaching to the side chain amino group a molecule as defined herein.

In one embodiment the side chain of i) the first amino-alkyl amino acid residue, ii) the second amino-alkyl amino acid residue, iii) the third amino-alkyl amino acid residue, iv) the first and the second amino-alkyl amino acid residues, v) the first and the third amino-alkyl amino acid residues, vi) the second and the third amino-alkyl amino acid residues, or vii) the first, the second and the third amino-alkyl amino acid residues, are each modified by attaching to the side chain amino group a molecule as defined herein.

In one embodiment the first lysine residue, or the second lysine residue, or the third lysine residue, or the first and the second lysine residues, or the first and the third lysine residues, or the second and the third lysine residues, or the first, the second and the third lysine residues of the lysine backbone of the branched amino acid probe of the invention are each modified by attaching a molecule to the ε-amino group.

In one embodiment, the molecule to be attached to the ε-amino group(s) of the one or more lysine residues of the lysine backbone of the branched amino acid probe are independently selected from the group consisting of $Lys_q$-Lys (SEQ ID NO: 117); $(aa_3)_p$-$Lys_q$ (SEQ ID NOs: 119-124); $Lys_q$-$(aa_3)_p$ (SEQ ID NOs: 125-130); $[(aa_3)$-Lys$]_p$ (SEQ ID NOs: 131 and 132) and [Lys-$(aa_3)]_p$ (SEQ ID NOs: 133 and 134), wherein q is a number selected from 0, 1, 2 and 3; p is a number selected from 1, 2 and 3, and $(aa_3)$ is an amino acid residue independently selected from Arg, His, Gly and Ala.

It follows that in one embodiment the first lysine residue, or the second lysine residue, or the third lysine residue, or the first and the second lysine residues, or the first and the third lysine residues, or the second and the third lysine residues, or the first, the second and the third lysine residues of the branched amino acid probe are modified by attaching to the ε-amino group(s) a molecule independently selected from the group consisting of $Lys_q$-Lys (SEQ ID NO: 117); $(aa_3)_p$-$Lys_q$ (SEQ ID NOs: 119-124); $Lys_q$-$(aa_3)_p$ (SEQ ID NOs: 125-130); $[(aa_3)$-Lys$]_p$ (SEQ ID NOs: 131 and 132) and [Lys-$(aa_3)]_p$ (SEQ ID NOs: 133 and 134), wherein q is a number selected from 0, 1, 2 and 3; p is a number selected from 1, 2 and 3, and $(aa_3)$ is an amino acid residue independently selected from Arg, His, Gly and Ala.

In a particular embodiment $(aa_3)$ is an amino acid residue independently selected from Gly and Ala. In a further embodiment, $(aa_3)$ is Gly.

In one embodiment, the molecules to be attached to the side chain amino group(s) are further acetylated. In one embodiment the molecules are independently selected from the group consisting of Ac-$AAA_q$-AAA (SEQ ID NO: 168); Ac-$(aa_3)_p$-$AAA_q$ (SEQ ID NOs: 169-174); Ac-$AAA_q$-$(aa_3)_p$ (SEQ ID NOs: 175-180); Ac-$[(aa_3)$-AAA$]_p$ (SEQ ID NOs: 181 and 182) and Ac-[AAA-$(aa_3)]p$ (SEQ ID NOs: 183-184), and/or $AAA_q$-AAA (SEQ ID NO: 168); $(aa_3)_p$-$AAA_q$ (SEQ ID NOs: 169-174); $AAA_q$-$(aa_3)_p$ (SEQ ID NOs: 175-180); $[(aa_3)$-AAA$]_p$ (SEQ ID NOs: 181 and 182) and [AAA-$(aa_3)]_p$ (SEQ ID NOs: 183 and 184).

In one embodiment the molecules are independently selected from the group consisting of Ac-$Orn_q$-Orn (SEQ ID NO: 135); Ac-$(aa_3)_p$-$Orn_q$ (SEQ ID NOs: 136-141); Ac-$Orn_q$-$(aa_3)_p$ (SEQ ID NOs: 142-147); Ac-$[(aa_3)$-Orn$]_p$ (SEQ ID NOs: 148 and 149); Ac-[Orn-$(aa_3)]_p$ (SEQ ID NOs: 150 and 151); Ac-$Orn_p$-$Lys_p$ (SEQ ID NOs: 152-157); Ac-$Lys_p$-$Orn_p$ (SEQ ID NOs: 158-163); Ac-[Orn-Lys]$_p$ (SEQ ID NOs: 164 and 165) and Ac-[Lys-Orn]$_p$ (SEQ ID NOs: 166 and 167), and/or $Orn_q$-Orn (SEQE ID NO: 135); $(aa_3)_p$-$Orn_q$ (SEQ ID NOs: 136-141); $Orn_q$-$(aa_3)_p$ (SEQ ID NOs: 142-147); $[(aa_3)$-Orn$]_p$ (SEQ ID NOs: 148 and 149) and [Orn-$(aa_3)]_p$ (SEQ ID NOs: 150 and 151); $Orn_p$-$Lys_p$ (SEQ ID NOs: 152-157); $Lys_p$-$Orn_p$ (SEQ ID NOs: 158-163); [Orn-Lys]$_p$ (SEQ ID NOs: 164 and 165) and [Lys-Orn]$_p$ (SEQ ID NOs: 166 and 167).

It follows that the molecules are in one embodiment independently selected from the group consisting of Ac-$Lys_q$-Lys (SEQ ID NO: 118); Ac-$(aa_3)_p$-$Lys_q$ (SEQ ID NOs: 119-124); Ac-$Lys_q$-$(aa_3)_p$ (SEQ ID NOs: 125-130); Ac-$[(aa_3)$-Lys]p (SEQ ID NOs: 131 and 132) and Ac-[Lys-$(aa_3)]_p$ (SEQ ID NOs: 133 and 134), and/or $Lys_q$-Lys (SEQ ID NO: 117); $(aa_3)_p$-$Lys_q$ (SEQ ID NOs: 119-124); $Lys_q$-$(aa_3)_p$ (SEQ ID NOs: 125-130); $[(aa_3)$-Lys$]_p$ (SEQ ID NOs: 131 and 132) and [Lys-$(aa_3)]p$ (SEQ ID NOs: 133 and 134).

In a particular embodiment, the molecule to be attached to the side chain amino group(s) is $AAA_q$-AAA (SEQ ID NO: 168), wherein q is a number selected from 0, 1, 2 and 3.

It follows that in one embodiment the branched amino acid probe consists of 2 to 9 amino-alkyl amino acid residues. In one embodiment said 2 to 9 amino-alkyl amino acid residues are individually selected from the group consisting of L-lysine, D-lysine, L-ornithine and D-ornithine.

In a particular embodiment, the molecule to be attached to the side chain amino group(s) is $Lys_q$-Lys (SEQ ID NO: 117), wherein q is a number selected from 0, 1, 2 and 3.

It follows that in one embodiment the branched amino acid probe of the invention consists of 2 to 9 lysine residues selected from Lys and D-Lys.

In one embodiment, the branched amino acid probe comprises a maximum of 1, 2, 3 or 4 amino acids selected from Arg, His, Gly and Ala ($aa_3$), wherein the remaining amino acids are amino-alkyl amino acid residues. In another embodiment, the branched amino acid probe comprises a maximum of 1 Arg residue, and/or comprises a maximum of 1 His residue, and/or comprises a maximum of 1 Gly residue, and/or comprises a maximum of 1 Ala residue.

In one embodiment, the molecule to be attached to the side chain amino group(s) of one or more of the first, second and/or third amino-alkyl amino acid residues is selected from the group consisting of AAA, Ac-AAA, AAA-AAA, Ac-AAA-AAA, AAA-AAA-AAA, Ac-AAA-AAA-AAA, AAA-AAA-AAA-AAA (SEQ ID NO: 168), Ac-AAA-AAA-AAA-AAA (SEQ ID NO: 168), AAA-Gly-AAA, Ac-AAA-Gly-AAA, AAA-AAA-Gly, Ac-AAA-AAA-Gly, AAA-Gly, Ac-AAA-Gly, AAA-Ala-AAA, Ac-AAA-Ala-AAA, AAA-AAA-Ala, Ac-AAA-AAA-Ala, AAA-Ala, Ac-AAA-Ala, AAA-His-AAA, Ac-AAA-His-AAA, AAA-AAA-His, Ac-AAA-AAA-His, AAA-His, Ac-AAA-His, AAA-Arg-AAA, Ac-AAA-Arg-AAA, AAA-AAA-Arg, Ac-AAA-AAA-Arg, AAA-Arg and Ac-AAA-Arg; wherein AAA is an amino-alkyl amino acid residue as specified herein (optionally individually acetylated). The above-mentioned AAA, Gly, Ala, His and Arg amino acid residues may each be in the L- or D-conformation.

In one embodiment, the molecule to be attached to the side chain amino group(s) of one or more of the first, second and/or third amino-alkyl amino acid residues is selected from the group consisting of Lys, Ac-Lys, Lys-Lys, Ac-Lys-Lys, Lys-Lys-Lys, Ac-Lys-Lys-Lys, Lys-Lys-Lys-Lys (SEQ ID NO: 117), Ac-Lys-Lys-Lys-Lys (SEQ ID NO: 118), Lys-Gly-Lys, Ac-Lys-Gly-Lys, Lys-Lys-Gly, Ac-Lys-Lys-Gly, Lys-Gly, Ac-Lys-Gly, Lys-Ala-Lys, Ac-Lys-Ala-Lys, Lys-Lys-Ala, Ac-Lys-Lys-Ala, Lys-Ala, Ac-Lys-Ala, Lys-His-Lys, Ac-Lys-His-Lys, Lys-Lys-His, Ac-Lys-Lys-His, Lys-His, Ac-Lys-His, Lys-Arg-Lys, Ac-Lys-Arg-Lys, Lys-Lys-Arg, Ac-Lys-Lys-Arg, Lys-Arg and Ac-Lys-Arg.

In a particular embodiment, the molecule to be attached to the ε-amino group(s) of one or more of the first, second and/or third lysine residues is selected from the group consisting of Lys, Ac-Lys, Lys-Lys, Ac-Lys-Lys, Lys-Lys-Lys, Ac-Lys-Lys-Lys, Lys-Lys-Lys-Lys (SEQ ID NO: 117), Ac-Lys-Lys-Lys-Lys (SEQ ID NO: 118), Lys-Gly-Lys, Ac-Lys-Gly-Lys, Lys-Lys-Gly, Ac-Lys-Lys-Gly, Lys-Gly, Ac-Lys-Gly, Lys-Ala-Lys, Ac-Lys-Ala-Lys, Lys-Lys-Ala, Ac-Lys-Lys-Ala, Lys-Ala, Ac-Lys-Ala, Lys-His-Lys, Ac-Lys-His-Lys, Lys-Lys-His, Ac-Lys-Lys-His, Lys-His, Ac-Lys-His, Lys-Arg-Lys, Ac-Lys-Arg-Lys, Lys-Lys-Arg, Ac-Lys-Lys-Arg, Lys-Arg and Ac-Lys-Arg.

In a particular embodiment, the branched amino acid probe of the invention comprise or consist of a first lysine residue selected from Lys and D-Lys, said first lysine residue being optionally acetylated, wherein said first lysine residue is modified by attaching to the ε-amino group of said first lysine residue a molecule selected from the group consisting of Lys, Ac-Lys, Lys-Lys, Ac-Lys-Lys, Lys-Lys-Lys, Ac-Lys-Lys-Lys, Lys-Lys-Lys-Lys (SEQ ID NO: 117), Ac-Lys-Lys-Lys-Lys (SEQ ID NO: 118), Lys-Gly-Lys, Ac-Lys-Gly-Lys, Lys-Lys-Gly, Ac-Lys-Lys-Gly, Lys-Gly, Ac-Lys-Gly, Lys-Ala-Lys, Ac-Lys-Ala-Lys, Lys-Lys-Ala, Ac-Lys-Lys-Ala, Lys-Ala, Ac-Lys-Ala, Lys-His-Lys, Ac-Lys-His-Lys, Lys-Lys-His, Ac-Lys-Lys-His, Lys-His, Ac-Lys-His, Lys-Arg-Lys, Ac-Lys-Arg-Lys, Lys-Lys-Arg, Ac-Lys-Lys-Arg, Lys-Arg and Ac-Lys-Arg.

In a particular embodiment, the branched amino acid probe of the invention comprise or consist of a first and a second lysine residue each selected from Lys and D-Lys, said first and second lysine residues each being optionally acetylated, wherein i) said first lysine residue, ii) said second lysine residue, or iii) said first and second residue are each modified by attaching to the ε-amino group of said lysine residue a molecule selected from the group consisting of Lys, Ac-Lys, Lys-Lys, Ac-Lys-Lys, Lys-Lys-Lys, Ac-Lys-Lys-Lys, Lys-Lys-Lys-Lys (SEQ ID NO: 117), Ac-Lys-Lys-Lys-Lys (SEQ ID NO: 118), Lys-Gly-Lys, Ac-Lys-Gly-Lys, Lys-Lys-Gly, Ac-Lys-Lys-Gly, Lys-Gly, Ac-Lys-Gly, Lys-Ala-Lys, Ac-Lys-Ala-Lys, Lys-Lys-Ala, Ac-Lys-Lys-Ala, Lys-Ala, Ac-Lys-Ala, Lys-His-Lys, Ac-Lys-His-Lys, Lys-Lys-His, Ac-Lys-Lys-His, Lys-His, Ac-Lys-His, Lys-Arg-Lys, Ac-Lys-Arg-Lys, Lys-Lys-Arg, Ac-Lys-Lys-Arg, Lys-Arg and Ac-Lys-Arg.

In a particular embodiment, the branched amino acid probe of the invention comprise or consist of a first, a second and a third lysine residue each selected from Lys and D-Lys, said first, second and third lysine residue each being optionally acetylated, wherein i) said first lysine residue, ii) said second lysine residue, iii) said third lysine residue, iv) said first and second lysine residue, v) said first and third lysine residue, vi) said second and third lysine residue, or vii) said first, second and third lysine residues are each modified by attaching to the ε-amino group of said lysine residue a molecule selected from the group consisting of Lys, Ac-Lys, Lys-Lys, Ac-Lys-Lys, Lys-Lys-Lys, Ac-Lys-Lys-Lys, Lys-Lys-Lys-Lys (SEQ ID NO: 117), Ac-Lys-Lys-Lys-Lys (SEQ ID NO: 118), Lys-Gly-Lys, Ac-Lys-Gly-Lys, Lys-Lys-Gly, Ac-Lys-Lys-Gly, Lys-Gly, Ac-Lys-Gly, Lys-Ala-Lys, Ac-Lys-Ala-Lys, Lys-Lys-Ala, Ac-Lys-Lys-Ala, Lys-Ala, Ac-Lys-Ala, Lys-His-Lys, Ac-Lys-His-Lys, Lys-Lys-His, Ac-Lys-Lys-His, Lys-His, Ac-Lys-His, Lys-Arg-Lys, Ac-Lys-Arg-Lys, Lys-Lys-Arg, Ac-Lys-Lys-Arg, Lys-Arg and Ac-Lys-Arg.

In one embodiment the branched amino acid probe comprises or consists of the formula: Ac-(Ac-Lys-Lys)Lys$_1$- (identical to Ac-(Ac-Lys-Lys)Lys-), wherein Lys$_1$ is the first lysine residue, which is acetylated, and (Ac-Lys-Lys) is the molecule attached to the ε-amino group of said first lysine residue Lys$_1$. FIG. 1 illustrates this formula/structure.

In one embodiment the branched amino acid probe comprises or consists of a formula selected from the group consisting of Ac-(Ac-Lys)Lys$_1$-, Ac-(Ac-Lys-Lys)Lys$_1$-, Ac-(Ac-Lys-Lys-Lys)Lys$_1$-, Ac-(Ac-Lys-Lys-Lys-Lys)Lys$_1$-, Ac-(Ac-Lys-Gly-Lys)Lys$_1$-, Ac-(Ac-Lys-Lys-Gly)Lys$_1$-, Ac-(Ac-Lys-Gly)Lys$_1$-, Ac-(Ac-Lys-Ala-Lys)Lys$_1$-, Ac-(Ac-Lys-Lys-Ala)Lys$_1$-, Ac-(Ac-Lys-Ala)Lys$_1$-, Ac-(Ac-Lys-His-Lys)Lys$_1$-, Ac-(Ac-Lys-Lys-His)Lys$_1$-, Ac-(Ac-Lys-His)Lys$_1$-, Ac-(Ac-Lys-Arg-Lys)Lys$_1$-, Ac-(Ac-Lys-Lys-Arg)Lys$_1$-, and Ac-(Ac-Lys-Arg)Lys$_1$-.

More specifically, in one embodiment the branched amino acid probe comprises or consists of a formula selected from the group consisting of Ac-(Ac-Lys)Lys$_1$-, Ac-(Ac-Lys-Lys)Lys$_1$-, Ac-(Ac-Lys-Lys-Lys)Lys$_1$-, Ac-(Ac-Lys-Lys-Lys-Lys)Lys$_1$-, Ac-(Ac-Lys-Gly-Lys)Lys$_1$-, Ac-(Ac-Lys-Lys-Gly)Lys$_1$- and Ac-(Ac-Lys-Gly)Lys$_1$-.

In one embodiment the branched amino acid probe comprises or consists of the formula: Ac-(Ac-Lys)Lys$_2$-Lys$_1$-, wherein Lys$_1$ is the first lysine residue, which is acetylated, Lys$_2$ is the second lysine residue being attached to Lys$_1$ via a peptide bond, and (Ac-Lys) is the molecule attached to the ε-amino group of said first lysine residue Lys$_1$.

In one embodiment the branched amino acid probe comprises or consists of the formula: Ac-Lys$_2$-(Ac-Lys)Lys$_1$-, wherein the molecule (Ac-Lys) is attached to the ε-amino group of said second lysine residue Lys$_2$.

In one embodiment the branched amino acid probe(s) is selected from the group consisting of Ac-(Ac-Lys)Lys-Lys-, (Ac-Lys)Lys-Lys-, Ac-(Lys)Lys-Lys-, (Lys)Lys-Lys-; Ac-Lys-(Ac-Lys)Lys-, Lys-(Ac-Lys)Lys-, Ac-Lys-(Lys) Lys-, Lys-(Lys)Lys-; Ac-(Ac-Lys-Lys)-Lys-, (Ac-Lys-Lys)-Lys-, Ac-(Lys-Lys)-Lys- and (Lys-Lys)-Lys-.

In one embodiment the branched amino acid probe(s) is selected from the group consisting of Ac-(Ac-Lys)Lys-, Ac-(Lys)Lys- and (Lys)Lys-.

In one embodiment the branched amino acid probe is selected from the group consisting of Ac-(Ac-Lys)Lys$_2$-Lys$_1$-, Ac-(Ac-Lys-Lys)Lys$_2$-Lys$_1$-, Ac-(Ac-Lys-Gly)Lys$_2$-Lys$_1$-, Ac-(Ac-Lys-Lys-Lys)Lys$_2$-Lys$_1$-, Ac-(Ac-Lys-Lys-Lys)Lys$_2$-Lys$_1$-, Ac-Lys$_1$-(Ac-Lys)-Lys$_1$-, Ac-Lys$_2$-(Ac-Lys-Lys)-Lys$_1$-, Ac-Lys$_1$-(Ac-Lys-Gly)-Lys$_1$-, Ac-Lys$_1$-(Ac-Lys-Lys-Lys)-Lys$_1$-, Ac-Lys$_2$-(Ac-Lys-Lys-Lys-Lys)-Lys$_1$-, Ac-(Ac-Lys)Lys$_2$-(Ac-Lys-)-Lys$_1$-, Ac-(Ac-Lys)Lys$_2$-(Ac-Lys-Lys-)-Lys$_1$-, and Ac-(Ac-Lys-Lys)Lys$_2$-(Ac-Lys-Lys-)-Lys$_1$-.

More specifically, in one embodiment the branched amino acid probe is selected from the group consisting of Ac-(Ac-Lys)Lys$_2$-Lys$_1$-, Ac-(Ac-Lys-Lys)Lys$_2$-Lys$_1$-, Ac-(Ac-Lys-Gly)Lys$_2$-Lys$_1$-, Ac-Lys$_1$-(Ac-Lys)-Lys$_1$-, Ac-Lys$_1$-(Ac-Lys-Lys)-Lys$_1$-, Ac-Lys$_1$-(Ac-Lys-Gly)-Lys$_1$-, Ac-(Ac-Lys)Lys$_2$-(Ac-Lys-)-Lys$_1$-, Ac-(Ac-Lys)Lys$_2$-(Ac-Lys-Lys-)-Lys$_1$-, and Ac-(Ac-Lys-Lys)Lys$_2$-(Ac-Lys-Lys-)-Lys$_1$-.

In one embodiment the branched amino acid probe is selected from the group consisting of Ac-Lys$_3$- Lys$_1$-(Ac-Lys)Lys$_1$-, Ac-Lys$_3$-(Ac-Lys)Lys$_2$-Lys$_1$-, Ac-(Ac-Lys)Lys$_3$-Lys$_1$-Lys$_1$-, Ac-Lys$_3$-(Ac-Lys)Lys$_2$-(Ac-Lys)Lys$_1$-, Ac-(Ac-Lys)Lys$_3$-(Ac-Lys)Lys$_2$-Lys$_1$-, and Ac-(Ac-Lys)Lys$_3$-Lys$_2$-(Ac-Lys)Lys$_1$-.

In a particular embodiment the branched amino acid probe is selected from the group consisting of Ac-(Ac-Lys) Lys$_1$-, Ac-(Ac-Lys-Lys)Lys$_1$-, Ac-(Ac-Lys-Lys-Lys)Lys$_1$-, Ac-(Ac-Lys-Lys-Lys-Lys)Lys$_1$-, Ac-(Ac-Lys-Gly)Lys$_1$-, Ac-(Ac-Lys-Lys-Gly)Lys$_1$-, Ac-(Ac-Lys-Gly)Lys$_1$-, Ac-(Ac-Lys)Lys$_2$-Lys$_1$-, Ac-(Ac-Lys-Lys)Lys$_2$-Lys$_1$-, Ac-(Ac-Lys-Gly)Lys$_2$-Lys$_1$-, Ac-Lys$_2$-(Ac-Lys)-Lys$_1$-, Ac-Lys$_1$-(Ac-Lys-Lys)-Lys$_1$-, Ac-Lys$_1$-(Ac-Lys-Gly)-Lys$_1$-, Ac-(Ac-Lys)Lys$_2$-(Ac-Lys-)-Lys$_1$-, Ac-(Ac-Lys)Lys$_2$-(Ac-Lys-Lys-)-Lys$_1$-, Ac-(Ac-Lys-Lys)Lys$_2$-(Ac-Lys-Lys-)-Lys$_1$-, Ac-Lys$_3$- Lys$_1$-(Ac-Lys)Lys$_1$-, Ac-Lys$_3$-(Ac-Lys)Lys$_2$-Lys$_1$-, Ac-(Ac-Lys)Lys$_3$-Lys$_2$-Lys$_1$-, Ac-Lys$_3$-(Ac-Lys) Lys$_2$-(Ac-Lys)Lys$_1$-, Ac-(Ac-Lys)Lys$_3$-(Ac-Lys)Lys$_2$-Lys$_1$-, and Ac-(Ac-Lys)Lys$_3$-Lys$_2$-(Ac-Lys)Lys$_1$-.

In a particular embodiment, the branched amino acid probe consists of 3 lysine residues (selected from L-Lys and D-Lys).

In another embodiment, the branched amino acid probe consists of 2 lysine residues (selected from L-Lys and D-Lys).

In a particular embodiment, the branched amino acid probe consists of a first and a second lysine residue selected from Lys and D-Lys, wherein one or both of the first and second lysine residues are modified by attaching to the ε-amino group of said first and/or second lysine residue one lysine residue selected from Lys and D-Lys; wherein each of said lysine residues are optionally acetylated.

In a particular embodiment, the branched amino acid probe consists of a first lysine residue selected from Lys and D-Lys, wherein said first lysine residue is modified by attaching to the ε-amino group of said first lysine residue two lysine residues selected from Lys and D-Lys; wherein each of said lysine residues are optionally acetylated.

Linking the Branched Amino Acid Probes and the Peptide

According to the invention, the first amino-alkyl amino acid residue of each of the one or more branched amino acid probes is covalently linked to the N-terminus of a peptide, covalently linked to the C-terminus of a peptide, and/or attached to the side chain amino group of an amino-alkyl amino acid residue within a peptide to be modified according to the invention.

Attaching one or more branched amino acid probes to a peptide yields a peptide/probe-conjugate.

It is understood that covalently bound or linked to the N-terminus of a peptide means that a branched amino acid probe of the invention is linked by a peptide bond between the most N-terminal amino acid of said peptide and the first amino-alkyl amino acid residue of the branched amino acid probe.

Likewise, it is understood that covalently bound or linked to the C-terminus of a peptide means that a branched amino acid probe of the invention is linked by a peptide bond between the most C-terminal amino acid of said peptide and the first amino-alkyl amino acid residue of the branched amino acid probe.

Furthermore, it is understood that a branched amino acid probe in one embodiment is attached to the side chain amino group of an amino-alkyl amino acid residue within said peptide sequence.

In one particular embodiment said amino-alkyl amino acid residue within said peptide sequence is selected from the group consisting of an ornithine residue and a lysine residue. In one particular embodiment said amino-alkyl amino acid residue within said peptide sequence is a lysine residue.

In one embodiment the first amino-alkyl amino acid residue of the branched amino acid probe of the invention is attached to the δ-amino group of an ornithine residue within said peptide or the ε-amino group of a lysine residue within said peptide.

In one embodiment the first amino-alkyl amino acid residue of the branched amino acid probe of the invention is attached to the ε-amino group of a lysine residue within said peptide.

It is understood that an amino-alkyl amino acid residue within said peptide sequence means that the amino-alkyl amino acid residue does not form part of the branched amino acid probe per se, but is a residue occurring within the existing amino acid sequence of the peptide. Said amino-alkyl amino acid residue can be positioned at any position of the peptide, i.e. it may be the first amino acid of the peptide, the second amino acid of the peptide, the third amino acid of the peptide, the fourth amino acid of the peptide, and so forth continuing until the last amino acid residue of the peptide.

According to the invention, a peptide analogue comprising one or more branched amino acid probes means that the peptide analogue in one embodiment comprises 1 branched amino acid probe, such as 2 branched amino acid probes, for example 3 branched amino acid probes, such as 4 branched amino acid probes, for example 5 branched amino acid probes, such as 6 branched amino acid probes, for example 7 branched amino acid probes, such as 8 branched amino acid probes, for example 9 branched amino acid probes, such as 10 branched amino acid probes.

In principle the peptide analogue can comprise any number of branched amino acid probes provided they can be attached to the peptide (N-terminally, C-terminally and/or one or more amino-alkyl amino acid residues within said peptide sequence.

In one embodiment of the invention the peptide analogue of the invention comprises 1 branched amino acid probe.

In one embodiment the peptide analogue comprises 1 branched amino acid probe, which branched amino acid probe is covalently bound to the N-terminus of the peptide.

In one embodiment the peptide analogue comprises 1 branched amino acid probe, which branched amino acid probe is covalently bound to the C-terminus of the peptide.

In one embodiment the peptide analogue comprises 1 branched amino acid probe, which branched amino acid probe is attached to the side chain amino group of an amino-alkyl amino acid residue within said peptide sequence.

In one embodiment the peptide analogue comprises more than one (two or more) branched amino acid probe(s). In the embodiments wherein the peptide analogue comprises more than one branched amino acid probe it is understood that the more than one branched amino acid probes may individually be the same (identical) or different (non-identical).

In one embodiment of the invention the peptide analogue of the invention comprises 2 branched amino acid probes.

In one embodiment the peptide analogue comprises 2 branched amino acid probes, wherein one branched amino acid probe is covalently bound to the N-terminus of the peptide and another branched amino acid probe is covalently bound to the C-terminus of the peptide.

In one embodiment the peptide analogue comprises 2 branched amino acid probes, wherein one branched amino acid probe is covalently bound to the N-terminus of the peptide and another branched amino acid probe is attached to the side chain amino group of an amino-alkyl amino acid residue within said peptide sequence.

In one embodiment the peptide analogue comprises 2 branched amino acid probes, wherein one branched amino acid probe is covalently bound to the C-terminus of the peptide and another branched amino acid probe is attached to the side chain amino group of an amino-alkyl amino acid residue within said peptide sequence.

In one embodiment the peptide analogue comprises 2 branched amino acid probes, wherein each of the two branched amino acid probes are attached to the side chain amino group of different (or separate) amino-alkyl amino acid residues within said peptide sequence.

In one embodiment of the invention the peptide analogue of the invention comprises 3 branched amino acid probes.

In one embodiment the peptide analogue of the invention comprises 3 branched amino acid probes, wherein the first branched amino acid probe is covalently bound to the N-terminus of the peptide, the second branched amino acid probe is covalently bound to the C-terminus of the peptide and the third branched amino acid probe is attached to the side chain amino group of an amino-alkyl amino acid residue within said peptide sequence.

In one embodiment the peptide analogue of the invention comprises 3 branched amino acid probes, wherein the first branched amino acid probe is covalently bound to the N-terminus of the peptide, and the second and third branched amino acid probes are each attached to the side chain amino group of different amino-alkyl amino acid residues within said peptide sequence.

In one embodiment the peptide analogue of the invention comprises 3 branched amino acid probes, wherein the first branched amino acid probe is covalently bound to the C-terminus of the peptide, and the second and third branched amino acid probes are each attached to the side chain amino group of different amino-alkyl amino acid residues within said peptide sequence.

In one embodiment the peptide analogue of the invention comprises 3 branched amino acid probes, wherein each of the first, the second and the third branched amino acid probes are attached to the side chain amino group of different amino-alkyl amino acid residues within said peptide sequence.

Peptide Part of the Analogue

The peptide analogue according to the present invention comprises a peptide and one or more branched amino acid probes.

In one embodiment the peptide of the peptide analogue is any peptide, polypeptide or protein, which peptide in one embodiment is native or naturally occurring, which peptide in one embodiment is a biologically active variant of a naturally occurring peptide.

In one embodiment said peptide is a fragment of a larger polypeptide or protein.

In one embodiment said peptide is an N-terminal fragment comprising from 1-50 of the most N-terminal amino acids of said protein, such as 1-2, 2-3, 3-4, 4-5, 5-6, 6-7, 7-8, 8-9, 9-10, 10-12, 12-14,14-16, 16-18, 18-20, 20-25, 25-30, 30-35, 35-40, 40-45, 45-50 of the most N-terminal amino acids of said protein.

In one embodiment said peptide is a C-terminal fragment comprising from 1-50 of the most C-terminal amino acids of said protein, such as 1-2, 2-3, 3-4, 4-5, 5-6, 6-7, 7-8, 8-9, 9-10, 10-12, 12-14,14-16, 16-18, 18-20, 20-25, 25-30, 30-35, 35-40, 40-45, 45-50 of the most C-terminal amino acids of said protein.

In one embodiment said peptide is a fragment comprising from 1-50 consecutive amino acid residues of said protein, such as 1-2, 2-3, 3-4, 4-5, 5-6, 6-7, 7-8, 8-9, 9-10, 10-12, 12-14,14-16, 16-18, 18-20, 20-25, 25-30, 30-35, 35-40, 40-45, 45-50 consecutive amino acid residues of said protein.

In some embodiments, the peptide analogues provided herein have one or more improved properties compared to the native peptide.

A peptide is a single linear polymer chain derived from the condensation of amino acids. Peptides may be distinguished from proteins on the basis of size, and as an arbitrary benchmark can be understood to contain approximately 75 (such as 50) or fewer amino acid residues.

In one embodiment the peptide part of the peptide analogue of the present invention is a peptide having (comprising or consisting of) 2 to 100 amino acid residues, such as from 2 to 3, for example 3 to 4, such as 4 to 5, for example 5 to 6, such as 6 to 7, for example 7 to 8, such as 8 to 9, for example 9 to 10, such as 10 to 12, for example 12 to 14, such as 14 to 16, for example 16 to 18, such as 18 to 20, for example 20 to 25, such as 25 to 30, for example 30 to 40, such as 40 to 50, for example 50 to 75, such as 75 to 100 amino acid residues.

In one embodiment the peptide of the present invention is a peptide having less than 50 amino acid residues, such as less than 40, for example less than 30, amino acid residues.

The sequence of amino acid residues in a native peptide is defined by the sequence of a gene, which is encoded in the genetic code. In general, the genetic code specifies 20 standard amino acids naturally incorporated into polypeptides (proteinogenic): Ala, Arg, Asn, Asp, Cys, Gln, Glu, Gly, His, Ile, Leu, Lys, Met, Phe, Pro, Ser, Tyr, Thr, Trp, Val, and 2 which are incorporated into proteins by unique synthetic mechanisms: Sec (selenocysteine, or U) and Pyl (pyrrolysine, 0). These are all L-stereoisomers.

Aside from the 22 standard or natural amino acids, there are many other non-naturally occurring amino acids (non-proteinogenic or non-standard). They are either not found in proteins, or are not produced directly and in isolation by standard cellular machinery.

Non-standard amino acids are usually formed through modifications to standard amino acids, such as post-translational modifications. Examples of unnatural amino acid residues are Nle (Norleucine), Orn (ornithine, deguanylated Arginine), Nal (beta-2-naphthyl-alanine), D-Nal (beta-2-naphthyl-D-alanine), D-Arg, D-Trp, D-Phe and D-Val.

Any amino acids according to the present invention may be in the L- or D-configuration. If nothing is specified, reference to the L-isomeric form is preferably meant.

The term peptide also embraces post-translational modifications introduced by chemical or enzyme-catalyzed reactions, as are known in the art. Such post-translational modifications can be introduced prior to partitioning, if desired. Also, functional equivalents may comprise chemical modifications such as ubiquitination, labeling (e.g., with radionuclides, various enzymes, etc.), pegylation (derivatization with polyethylene glycol), or by insertion (or substitution by chemical synthesis) of amino acids such as ornithine, which do not normally occur in human proteins.

Peptides with N-terminal alkylations and C-terminal esterifications are also encompassed within the present invention. Functional equivalents also comprise glycosylated and covalent or aggregative conjugates formed with the same molecules, including dimers or unrelated chemical moieties. Such functional equivalents are prepared by linkage of functionalities to groups which are found in a fragment including at any one or both of the N- and C-termini, by means known in the art.

In some embodiments, the peptides according to the present invention are modified by acetylation, such as N-terminal acetylation. In some embodiments the peptides according to the present invention are modified by C-terminal amidation.

The peptides of the present invention may be any peptide known to the skilled person as having a biological effect. In one embodiment the addition of a branched amino acid probe to the peptide in question will influence said biological effect, such as enhance or improve a biological effect.

A variant of a peptide of the invention is in one embodiment a peptide derived from the native peptide by fragmentation (such as N-terminal fragments, C-terminal fragments, or fragments from within a peptide), deletion, insertion, mutation or substitution of one or more amino acid residues (such as conservative amino acid substitution or introduction of non-proteinogenic amino acid residues), and/or modulation of the peptide such as by acetylation, by insertion of an amino acid in the D-configuration, and other modifications known to the skilled person.

In one embodiment the peptide analogue of the invention comprises one or more branched amino acid probes and a peptide having an immune-modulating effect (an immune-modulating peptide), in one embodiment having an anti-inflammatory and/or pro-resolving effect.

In one embodiment the peptide analogue of the invention comprises one or more branched amino acid probes and a peptide having a metabolic effect.

In one embodiment the peptide analogue of the invention comprises one or more branched amino acid probes and a peptide having a cardiovascular effect.

In one embodiment the peptide analogue of the invention comprises one or more branched amino acid probes and a peptide having an organ protective and/or tissue protective effect.

In one embodiment the peptide analogue comprises a peptide hormone, a neurotransmitter, a neuropeptide, a lipopeptide, an enzyme, a growth factor, a metabologen, a transcription factor, a receptor agonist, a receptor antagonist, a ligand, or a carrier protein.

In one embodiment the peptide analogue comprises a peptide selected from the group consisting of VIP (Vasoactive Intestinal Peptide; PHM27), PACAP (Pituitary Adenylate Cyclase Activating Peptide), Peptide PHI 27 (Peptide Histidine Isoleucine 27), GHRH 1-24 (Growth Hormone Releasing Hormone 1-24), Glucagon, Secretin, glicentin precursor, GIP (gastric inhibitory peptide), prealbumin or transthyretin (TTR), peptide HI-27 and growth hormone releasing factor (GHRF or GHRH), incretins, glucagon-like peptide-1 (GLP-1), GLP-1 (7-37), GLP-1 (7-33), glucagon-like peptide-2 (GLP-2) and exendin-4, or variants thereof.

In one embodiment the peptide analogue comprises a peptide selected from the group consisting of somatotrophins (such as somatotropin or growth hormone (GH)), Thyrotrophins (such as Thyroid-stimulating hormone (TSH), Corticotropins (such as Adrenocorticotropic hormone (ACTH), and Beta-endorphin), Lactotrophins (such as Prolactin (PRL), Gonadotropins (such as Luteinizing hormone (LH) and Follicle-stimulating hormone (FSH)), Antidiuretic hormone (ADH or vasopressin) Oxytocin, growth hormone-releasing hormone (GHRH), somatostatin, thyrotropin-releasing hormone (TRH), corticotropin-releasing hormone (CRH) Gonadotropin-Releasing Hormone (GnRH), CREB (cAMP response element-binding protein), Lactotripeptides, Isoleucine-Proline-Proline (IPP) and Valine-Proline-Proline (VPP), and variants thereof.

In one embodiment the peptide analogue comprises a pancreatic polypeptide-related peptide including NPY (NeuroPeptide Y), PYY (Peptide YY), APP (Avian Pancreatic Polypeptide) and PPY/PP (Pancreatic Polypeptide), or variants thereof.

In one embodiment the peptide analogue comprises an opioid peptide (or opioid polypeptide hormone/opioid neuropeptide), including Proopiomelanocortin (POMC) peptides (including N-Terminal Peptide of Proopiomelanocortin (NPP, or pro-γ-MSH), γ-MSH, Corticotropin (Adrenocorticotropic Hormone, or ACTH), α-Melanotropin, α-MSH, Corticotropin-like Intermediate Peptide (CLIP), β-Lipotropin (β-LPH),Lipotropin Gamma (γ-LPH), β-MSH, β-Endorphin and [Met]Enkephalin); Enkephalin pentapeptides (Met-enkephalin and Leu-enkephalin), Prodynorphin peptides, dynorphins (dynorphin A, dynorphin B, α-neo-endorphin, β-neo-endorphin, and Big dynorphin), endorphins (beta-endorphin, Alpha-endorphin, Gamma-endorphin, α-neo-endorphin and β-neo-endorphin), Adrenorphin, Amidorphin, Leumorphin, Nociceptin, Opiorphin, and Spinorphin, or variants thereof.

In one embodiment the peptide analogue comprises a neuropeptide, or a neurotransmitter, including kinins, tachykinin neuropeptides (including substance P, kassinin, neurokinin A (NKA), neurokinin B (NKB), eledoisin and physalaemin), Bradykinin, Neuromedins/Bombesin-related peptides (including Neuromedin B (NMB), Neuromedin N, Neuromedin S and Neuromedin U (NmU)); Angiotensin, Bombesin, Calcitonin gene-related peptide (CGRP), α-CGRP, β-CGRP, Carnosine, Cocaine and amphetamine regulated transcript (CART), Delta sleep-inducing peptide (DSIP), FMRFamide, FMRFamide-related peptides (FaRPs), Galanin, Galanin-like peptide (GALP), Gastrin releasing peptide (GRP), Neuropeptide S, Neuropeptide Y, Neurophysins (Neurophysin I and Neurophysin II), Neurotensin, Pancreatic polypeptide, Pituitary adenylate cyclase activating peptide (PACAP), RVD-Hpα, hemopressin, VGF (VGF nerve growth factor inducible), and VGF-derived peptides (TLQP-21), or variants thereof.

In one embodiment the peptide analogue comprises a Calcitonin peptide, including Calcitonin, Amylin (or Islet Amyloid Polypeptide (IAPP)) and AGG01, or variants thereof.

In one embodiment the peptide analogue comprises a growth factor, including in one embodiment Adrenomedullin (AM), Angiopoietin (Ang), Autocrine motility factor, Bone morphogenetic proteins (BMPs) (BMP1, B;MP2, BMP3, BMP4, BMP5, BMP6, BMP7, BMP8a, BMP8b, BMP10, BMP15), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), Insulin-like growth factors (IGF), IGF-1, IGF-2, Migration-stimulating factor, Myostatin (GDF-8), neurotrophins, Neurotrophin-3 (NT-3), Neurotrophin-4 (NT-4), Nerve growth factor (NGF), Platelet-derived growth factor (PDGF), Thrombopoietin (TPO), Transforming growth factor alpha (TGF-α), Transforming growth factor beta (TGF-β), Tumor necrosis factor-alpha (TNF-α), Vascular endothelial growth factor (VEGF), Wnt proteins, Wnt1, Wnt2, Wnt2B, Wnt3, Wnt3A, Wnt4, Wnt5A, Wnt5B, Wnt6, Wnt7A, Wnt7B, Wnt8A, Wnt8B, Wnt9A, Wnt9B, Wnt10A, Wnt10B, Wnt11, Wnt16, placental growth factor (PGF) and Foetal Bovine Somatotrophin (FBS), or variants thereof.

In one embodiment the peptide analogue comprises a peptide of the insulin/IGF/relaxin family, including in one embodiment insulin and insulin-like growth factors, IGF-1, IGF-2, IGF-binding proteins, IGFBP1, IGFBP2, IGFBP3, IGFBP4, IGFBP5, IGFBP6, IGFBP7, Relaxin family peptide hormones, relaxin-like (RLN) peptides, insulin-like (INSL) peptides, RLN1 (relaxin 1), RLN2 (relaxin 2), RLN3 (relaxin 3), INSL3 (insulin-like peptide 3, Leydig cell-specific insulin-like peptide), INSL4 (insulin-like peptide 4, early placenta insulin-like peptide, ELIP), INSL5 (insulin-like peptide 5) and INSL6 (insulin-like peptide 6), or variants thereof.

In one embodiment the peptide analogue comprises a peptide hormone, including in one embodiment Gastrin, gastrin-34, gastrin-17, gastrin-14, pentagastrin, thyroid hormone (T4), Thyrotropin-releasing hormone (TRH), vasopressin, protein hormones, glycoprotein hormones, growth hormone (GH), insulin, LH, FSH, Thyroid-stimulating hormone (thyrotropin, TSH), Angiotensin (AGT), Angiotensin I, Angiotensin II, Angiotensin III, Angiotensin IV, Atrial natriuretic peptide (ANP), NT-proBNP, B-type Natriuretic Peptide (BNP) and Atrial natriuretic peptide (ANP), or variants thereof.

In one embodiment the peptide analogue comprises an Annexin protein, including in one embodiment annexin A-I (lipocortin I) and annexin A-II (annexin II), or variants thereof, including thereof, some of which are known in the art.

Agonist

In one embodiment the peptide analogue of the invention comprises an agonist. The term "agonist" in the present context refers to a substance or peptide as defined herein, capable of binding to, or in some embodiments, capable of binding to at least some extent and/or activating a receptor, or in some embodiments, activating a receptor to at least some extent.

An agonist may be an agonist of several different types of receptors, and thus capable of binding and/or activating several different types of receptors. Said agonist can also be a selective agonist which only binds and activates one type of receptor. The term "antagonist" in the present context refers to a substance capable of inhibiting the effect of a receptor agonist.

Full agonists bind (have affinity for) and activate a receptor, displaying full efficacy at that receptor. "Partial agonists" in the present context are peptides able to bind and activate a given receptor, but having only partial efficacy at the receptor relative to a full agonist. Partial agonists can act as antagonists when competing with a full agonist for receptor occupancy and producing a net decrease in the receptor activation compared to the effects or activation observed with the full agonist alone.

"Selective agonists" in the present context are compounds which are selective and therefore predominantly bind and activate one type of receptor.

Peptides according to the present invention are in one embodiment an agonist capable of binding and activating to some extent one or several receptors and can have different binding affinities and/or different receptor activation efficacy for different receptors, wherein affinity refers to the number and size of intermolecular forces between a peptide ligand and its receptor, and residence time of the ligand at its receptor binding site; and receptor activation efficacy refers to the ability of the peptide ligand to produce a biological response upon binding to the target receptor and the quantitative magnitude of this response.

In some embodiments, such differences in affinity and receptor activation efficacy are determined by receptor binding/activation studies which are conventional in the art, for instance by generating $EC_{50}$ and Emax values for stimulation of ligand binding in cells expressing one or several types of receptors, or on tissues expressing the different types of receptors. High affinity means that a lower concentration of a compound is needed to obtain a binding of 50% of the receptors compared to peptides which have lower affinity; high receptor activation efficacy means that a lower concentration of the peptide is needed to obtain a 50% receptor activation response (low $EC_{50}$ value), compared to peptides which have lower affinity and/or receptor activity efficacy (higher $EC_{50}$ value).

Melanocortins

In one embodiment the peptide of the peptide analogue of the invention is a melanocortin.

In one embodiment the melanocortin is selected from α-MSH, γ-MSH (comprising γ1-MSH and γ-MSH) and β-MSH, or variants thereof.

In one embodiment the melanocortin is selected from α-MSH and γ-MSH, or variants thereof.

In one embodiment, a peptide variant is a biologically active variant of the peptide, i.e. a variant which retains at least one function of the native (non-variant) peptide.

```
α-MSH
Ac-Ser-Tyr-Ser-Met-Glu-His-Phe-Arg-Trp-Gly-Lys-
Pro-Val (SEQ ID NO: 1)

SYSMEHFRWGKPV (SEQ ID NO: 1)

P01189[138-150], Pro-opiomelanocortin, Homo sapiens
aa modification: Valine amide (pos 150)

γ1-MSH
Tyr-Val-Met-Gly-His-Phe-Arg-Trp-Asp-Arg-Phe-Gly
(SEQ ID NO: 2)

YVMGHFRWDRFG (SEQ ID NO: 2)

P01189[77-88], Pro-opiomelanocortin, Homo sapiens
aa modifications: Phenylalanine amide (pos 88)

γ2-MSH
Tyr-Val-Met-Gly-His-Phe-Arg-Trp-Asp-Arg-Phe
(SEQ ID NO: 3)

YVMGHFRWDRF (SEQ ID NO: 3)

P01189[77-87], Pro-opiomelanocortin, Homo sapiens
aa modifications: Phenylalanine amide (pos 87)
```

It is thus an aspect of the present invention to provide a melanocortin analogue comprising a melanocortin peptide and one or more branched amino acid probes, wherein said branched amino acid probe comprises a first amino-alkyl amino acid residue, said first amino-alkyl amino acid residue optionally being covalently linked to a second amino-alkyl amino acid residue, or to a second and a third amino-alkyl amino acid residue, to form a linear chain of 2 or 3 amino-alkyl amino acid residues, wherein the side chain(s) of one or more of said first, second and/or third amino-alkyl amino acid residues are each modified by attaching to the side chain amino group a molecule independently selected from the group consisting of $AAA_q$-AAA; $(aa_3)_p$-$AAA_q$; $AAA_q$-$(aa_3)_p$; $[(aa_3)$-$AAA]_p$ and $[AAA$-$(aa_3)]p$;

wherein q is a number selected from 0, 1, 2 and 3; p is a number selected from 1, 2 and 3; AAA is an amino-alkyl amino acid residue; and $(aa_3)$ is an amino acid residue independently selected from Arg, His, Gly and Ala, wherein said amino-alkyl amino acid residues are optionally acetylated, wherein said first amino-alkyl amino acid residue is covalently linked to the N-terminus of said melanocortin peptide, covalently linked to the C-terminus of said melanocortin peptide, and/or attached to the side chain amino group of an amino-alkyl amino acid residue within said melanocortin peptide, with the proviso that said branched amino acid probe consists of 2 to 9 amino acid residues.

In one embodiment with the proviso that when the melanocortin analogue comprises one branched amino acid probe comprising one or more lysine residues, said branched amino acid probe is not attached to the N-terminus of said melanocortin.

In one embodiment with the proviso that when the melanocortin peptide of the analogue is α-MSH or γ-MSH, or variants thereof, said branched amino acid probe is not attached to the N-terminus of said melanocortin.

In one embodiment with the proviso that when the melanocortin analogue comprises one branched amino acid probe which comprises one or more lysine residues, and the melanocortin peptide of the analogue is α-MSH or γ-MSH, or variants thereof, said branched amino acid probe is not attached to the N-terminus of said melanocortin.

In one embodiment the first amino-alkyl amino acid residue(s) of the one or more branched amino acid probes is not covalently linked to the N-terminus of said melanocortin peptide.

In one embodiment the first amino-alkyl amino acid residue(s) of the one or more branched amino acid probes is not covalently linked to the N-terminus of said melanocortin peptide, provided i) said melanocortin analogues comprise one (1) branched amino acid probe, ii) said branched amino acid probe comprises one or more lysine residues, and/or iii) said melanocortin analogues comprise a melanocortin peptide selected from the group consisting of α-MSH and γ-MSH (comprising γ1-MSH and γ-MSH), or variants thereof.

In one embodiment said melanocortin analogue comprise one branched amino acid probe, which probe is covalently linked to the C-terminus of said peptide, or attached to the side chain amino group of an amino-alkyl amino acid residue within said melanocortin peptide.

In one embodiment the amino-alkyl amino acid residue within said melanocortin peptide is a lysine residue.

In one embodiment the amino-alkyl amino acid residue within said melanocortin peptide is an ornithine residue.

In one embodiment said melanocortin analogue is an α-MSH analogue and comprise a branched amino acid probe attached to the ε-amino group of the lysine residue (Lys) comprised in the native α-MSH peptide (underlined: Ac-Ser-Tyr-Ser-Met-Glu-His-Phe-Arg-Trp-Gly-Lys-Pro-Val) (SEQ ID NO: 1).

In one embodiment of the invention the melanocortin peptide analogue comprises 2 branched amino acid probes, wherein i) one branched amino acid probe is covalently bound to the N-terminus and another branched amino acid probe is covalently bound to the C-terminus of the melanocortin peptide; ii) one branched amino acid probe is covalently bound to the N-terminus and another branched amino acid probe is attached to the side chain amino group of an amino-alkyl amino acid residue within said melanocortin peptide; iii) one branched amino acid probe is covalently bound to the C-terminus and another branched amino acid probe is attached to the side chain amino group of an amino-alkyl amino acid residue within said melanocortin peptide; or iv) each of the two branched amino acid probes are attached to the side chain amino groups of different (or separate) amino-alkyl amino acid residues within said melanocortin peptide.

In one embodiment of the invention the peptide analogue of the invention comprises 3 branched amino acid probes, wherein each of the first, the second and the third branched amino acid probes are covalently bound to the N-terminus of the peptide, covalently bound to the C-terminus of the peptide or attached to the side chain amino group of an amino-alkyl amino acid residue within said melanocortin peptide.

In one embodiment the melanocortin analogue of the present invention comprises an α-MSH peptide, or variants thereof.

In one embodiment the melanocortin analogue of the present invention comprises a γ-MSH peptide, or variants thereof.

In one embodiment the melanocortin analogue of the present invention comprises one or more branched amino acid probes and a melanocortin peptide having the amino acid sequence:

$$(aa_1)n\text{-}Y\text{-}(aa_2)m\text{-}Z$$

wherein Y is an amino acid sequence consisting of 4 contiguous amino acid residues selected from the group consisting of His-Phe-Arg-Trp (SEQ ID NO: 4); His-(D-Phe)-Arg-Trp (SEQ ID NO: 5); His-Phe-(D-Arg)-Trp (SEQ ID NO: 6); His-Phe-Arg-(D-Trp) (SEQ ID NO: 7); His-(D-Phe)-Arg-(D-Trp) (SEQ ID NO: 8); His-Nal-Arg-Trp (SEQ ID NO: 9) and His-(D-Nal)-Arg-Trp (SEQ ID NO: 10); and wherein Z is an amino acid sequence consisting of 2 or 3 contiguous amino acid residues selected from the group consisting of Lys-Pro-Val; Lys-Pro-(D-Val); Arg-Phe-Gly; Arg-(D-Phe)-Gly; Arg-Phe and Arg-(D-Phe); and wherein n is a number selected from 0, 1, 2, 3, 4 and 5, and $(aa_1)$ independently can be any natural or unnatural amino acid residue, and wherein m is 0 or 1, and $(aa_2)$ can be any one natural or unnatural amino acid residue.

In one embodiment said melanocortin peptide is α-MSH or γ-MSH or is derived from α-MSH or γ-MSH.

In one embodiment $(aa_1)_n$ is a sequence consisting of from 0 to 5 amino acids (n=0, 1, 2, 3, 4, or 5). In a particular embodiment, $(aa_1)_n$ is a sequence consisting of 4 or 5 contiguous amino acids (n=4 or 5).

In one embodiment, $(aa_1)_n$ is selected from the group consisting of Ser-Tyr-Ser-Met-Glu (SEQ ID NO: 11), Ser-Tyr-Ser-Nle-Glu (SEQ ID NO: 12) and Ser-Ser-Ile-Ile-Ser (SEQ ID NO: 13), wherein said N-terminal Ser is optionally acetylated.

In one embodiment, $(aa_1)_n$ is selected from the group consisting of Ser-Tyr-Ser-Met-Glu (SEQ ID NO: 11), Ser-Tyr-Ser-Nle-Glu (SEQ ID NO: 12), Ser-Ser-Ile-Ile-Ser (SEQ ID NO: 13), Ac-Ser-Tyr-Ser-Met-Glu (SEQ ID NO: 11), Ac-Ser-Tyr-Ser-Nle-Glu (SEQ ID NO: 12) and Ac-Ser-Ser-Ile-Ile-Ser (SEQ ID NO: 13).

In one embodiment, $(aa_1)_n$ is selected from the group consisting of Tyr-Val-Met-Gly (SEQ ID NO: 14) and Tyr-Val-Nle-Gly (SEQ ID NO: 15).

In one embodiment $(aa_2)_m$ is selected from the group consisting of Gly and Asp. In one embodiment $(aa_2)_m$ is Gly. In another embodiment $(aa_2)_m$ is Asp.

In one embodiment, Z is Lys-Pro-Val or Lys-Pro-(D-Val). In another embodiment, Z is Arg-Phe-Gly or Arg-(D-Phe)-Gly. In yet another embodiment, Z is Arg-Phe or Arg-(D-Phe).

In one embodiment, the most carboxy terminal amino acid of the melanocortin peptide is amidated (—NH$_2$; —CONH$_2$). Thus, in one embodiment, Val or (D-Val) is a Valine amide. In another embodiment, Phe or (D-Phe) is a Phenylalanine amide. In yet another embodiment, Gly is Glycine amide.

In one embodiment the melanocortin analogue of the present invention comprises one or more branched amino acid probes and an α-MSH peptide having the amino acid sequence:

(aa$_1$)n-Y-(aa$_2$)m-Z wherein n is a number selected from 0, 1, 2, 3, 4 and 5, and (aa$_1$) independently is any natural or unnatural amino acid residue, and
wherein m is 0 or 1, and (aa$_2$) is any natural or unnatural amino acid residue, wherein Y is selected from the group consisting of His-Phe-Arg-Trp (SEQ ID NO: 4); His-(D-Phe)-Arg-Trp (SEQ ID NO: 5); His-Phe-(D-Arg)-Trp (SEQ ID NO: 6); His-Phe-Arg-(D-Trp) (SEQ ID NO: 7); His-(D-Phe)-Arg-(D-Trp) (SEQ ID NO: 8); His-Nal-Arg-Trp (SEQ ID NO: 9) and His-(D-Nal)-Arg-Trp (SEQ ID NO: 10); and wherein Z is selected from the group consisting of Lys-Pro-Val and Lys-Pro-(D-Val), and Val or (D-Val) is optionally valine amide.

In one embodiment (aa$_1$)$_n$ is selected from the group consisting of Ser-Tyr-Ser-Met-Glu (SEQ ID NO: 11), Ser-Tyr-Ser-Nle-Glu (SEQ ID NO: 12), Ser-Ser-Ile-Ile-Ser (SEQ ID NO: 13), Ac-Ser-Tyr-Ser-Met-Glu (SEQ ID NO: 11), Ac-Ser-Tyr-Ser-Nle-Glu (SEQ ID NO: 12) and Ac-Ser-Ser-Ile-Ile-Ser (SEQ ID NO: 13). In one embodiment (aa$_2$)$_m$ is Gly.

In one embodiment the melanocortin peptide is derived from α-MSH and (aa$_1$)$_n$ is Ser-Tyr-Ser-Met-Glu (SEQ ID NO: 11), Ser-Tyr-Ser-Nle-Glu (SEQ ID NO: 12) or Ser-Ser-Ile-Ile-Ser (SEQ ID NO: 13); Y is His-Phe-Arg-Trp (SEQ ID NO: 4), His-(D-Phe)-Arg-Trp (SEQ ID NO: 5) or His-Phe-Arg-(D-Trp) (SEQ ID NO: 7); (aa$_2$)$_m$ is Gly and Z is Lys-Pro-Val.

In one embodiment the melanocortin analogue of the present invention comprises one or more branched amino acid probes and an α-MSH peptide selected from the group consisting of (SEQ ID NO: 1)
Ser-Tyr-Ser-Met-Glu-His-Phe-Arg-Trp-Gly-Lys-Pro-Val, (SEQ ID NO: 16)
Ser-Tyr-Ser-Met-Glu-His-(D-Phe)-Arg-Trp-Gly-Lys-Pro-Val, (SEQ ID NO: 17)
Ser-Tyr-Ser-Met-Glu-His-Phe-(D-Arg)-Trp-Gly-Lys-Pro-Val (SEQ ID NO: 18)
Ser-Tyr-Ser-Met-Glu-His-Phe-Arg-(D-Trp)-Gly-Lys-Pro-Val, (SEQ ID NO: 19)
Ser-Tyr-Ser-Met-Glu-His-(D-Phe)-Arg-(D-Trp)-Gly-Lys-Pro-Val, (SEQ ID NO: 20)
Ser-Tyr-Ser-Met-Glu-His-Nal-Arg-Trp-Gly-Lys-Pro-Val, (SEQ ID NO: 21)
Ser-Tyr-Ser-Met-Glu-His-(D-Nal)-Arg-Trp-Gly-Lys-Pro-Val, (SEQ ID NO: 22)
Ser-Tyr-Ser-Met-Glu-His-Phe-Arg-Trp-Gly-Lys-Pro-(D-Val), (SEQ ID NO: 23)
Ser-Tyr-Ser-Met-Glu-His-(D-Phe)-Arg-Trp-Gly-Lys-Pro-(D-Val), (SEQ ID NO: 24)
Ser-Tyr-Ser-Met-Glu-His-Phe-(D-Arg)-Trp-Gly-Lys-Pro-(D-Val), (SEQ ID NO: 25)
Ser-Tyr-Ser-Met-Glu-His-Phe-Arg-(D-Trp)-Gly-Lys-Pro-(D-Val), (SEQ ID NO: 26)
Ser-Tyr-Ser-Met-Glu-His-(D-Phe)-Arg-(D-Trp)-Gly-Lys-Pro-(D-Val), (SEQ ID NO: 27)
Ser-Tyr-Ser-Met-Glu-His-Nal-Arg-Trp-Gly-Lys-Pro-(D-Val), (SEQ ID NO: 28)
Ser-Tyr-Ser-Met-Glu-His-(D-Nal)-Arg-Trp-Gly-Lys-Pro-(D-Val), (SEQ ID NO: 29)
Ser-Tyr-Ser-Nle-Glu-His-Phe-Arg-Trp-Gly-Lys-Pro-Val, (SEQ ID NO: 30)
Ser-Tyr-Ser-Nle Glu-His-(D-Phe)-Arg-Trp-Gly-Lys-Pro-Val, (SEQ ID NO: 31)
Ser-Tyr-Ser-Nle Glu-His-Phe-(D-Arg)-Trp-Gly-Lys-Pro-Val (SEQ ID NO: 32)
Ser-Tyr-Ser-Nle-Glu-His-Phe-Arg-(D-Trp)-Gly-Lys-Pro-Val, (SEQ ID NO: 33)
Ser-Tyr-Ser-Nle-Glu-His-(D-Phe)-Arg-(D-Trp)-Gly-Lys-Pro-Val, (SEQ ID NO: 34)
Ser-Tyr-Ser-Nle-Glu-His-Nal-Arg-Trp-Gly-Lys-Pro-Val, (SEQ ID NO: 35)
Ser-Tyr-Ser-Nle-Glu-His-(D-Nal)-Arg-Trp-Gly-Lys-Pro-Val, (SEQ ID NO: 36)
Ser-Tyr-Ser-Nle-Glu-His-Phe-Arg-Trp-Gly-Lys-Pro-(D-Val), (SEQ ID NO: 37)
Ser-Tyr-Ser-Nle-Glu-His-(D-Phe)-Arg-Trp-Gly-Lys-Pro-(D-Val), (SEQ ID NO: 38)
Ser-Tyr-Ser-Nle-Glu-His-Phe-(D-Arg)-Trp-Gly-Lys-Pro-(D-Val), (SEQ ID NO: 39)
Ser-Tyr-Ser-Nle Glu-His-Phe-Arg-(D-Trp)-Gly-Lys-Pro-(D-Val),

```
                                            (SEQ ID NO: 40)
Ser-Tyr-Ser-Nle-Glu-His-(D-Phe)-Arg-(D-Trp)-Gly-
Lys-Pro-(D-Val), (SEQ ID NO: 41)
Ser-Tyr-Ser-Nle-Glu-His-Nal-Arg-Trp-Gly-Lys-Pro-
(D-Val), (SEQ ID NO: 42)
Ser-Tyr-Ser-Nle-Glu-His-(D-Nal)-Arg-Trp-Gly-Lys-
Pro-(D-Val), (SEQ ID NO: 43)
Ser-Ser-Ile-Ile-Ser-His-Phe-Arg-Trp-Gly-Lys-Pro-
Val, (SEQ ID NO: 44)
Ser-Ser-Ile-Ile-Ser-His-(D-Phe)-Arg-Trp-Gly-Lys-
Pro-Val, (SEQ ID NO: 45)
Ser-Ser-Ile-Ile-Ser-His-Phe-(D-Arg)-Trp-Gly-Lys-
Pro-Val (SEQ ID NO: 46)
Ser-Ser-Ile-Ile-Ser-His-Phe-Arg-(D-Trp)-Gly-Lys-
Pro-Val, (SEQ ID NO: 47)
Ser-Ser-Ile-Ile-Ser-His-(D-Phe)-Arg-(D-Trp)-Gly-
Lys-Pro-Val, (SEQ ID NO: 48)
Ser-Ser-Ile-Ile-Ser-His-Nal-Arg-Trp-Gly-Lys-Pro-
Val, (SEQ ID NO: 49)
Ser-Ser-Ile-Ile-Ser-His-(D-Nal)-Arg-Trp-Gly-Lys-
Pro-Val, (SEQ ID NO: 50)
Ser-Ser-Ile-Ile-Ser-His-Phe-Arg-Trp-Gly-Lys-Pro-
(D-Val), (SEQ ID NO: 51)
Ser-Ser-Ile-Ile-Ser-His-(D-Phe)-Arg-Trp-Gly-Lys-
Pro-(D-Val), (SEQ ID NO: 52)
Ser-Ser-Ile-Ile-Ser-His-Phe-(D-Arg)-Trp-Gly-Lys-
Pro-(D-Val), (SEQ ID NO: 53)
Ser-Ser-Ile-Ile-Ser-His-Phe-Arg-(D-Trp)-Gly-Lys-
Pro-(D-Val), (SEQ ID NO: 54)
Ser-Ser-Ile-Ile-Ser-His-(D-Phe)-Arg-(D-Trp)-Gly-
Lys-Pro-(D-Val), (SEQ ID NO: 55)
Ser-Ser-Ile-Ile-Ser-His-Nal-Arg-Trp-Gly-Lys-Pro-
(D-Val),
and (SEQ ID NO: 56)
Ser-Ser-Ile-Ile-Ser-His-(D-Nal)-Arg-Trp-Gly-Lys-
Pro-(D-Val),
``` wherein the most carboxy terminal Val or (D-Val) is optionally a Valine amide.

In one embodiment the melanocortin analogue of the present invention comprises one or more branched amino acid probes and a γ-MSH peptide having the amino acid sequence:

$(aa_1)n$-Y-$(aa_2)m$-Z wherein n is a number selected from 0, 1, 2, 3, 4 and 5, and $(aa_1)$ independently is any natural or unnatural amino acid residue, and wherein m is 0 or 1, and $(aa_2)$ is any natural or unnatural amino acid residue, wherein Y is selected from the group consisting of His-Phe-Arg-Trp (SEQ ID NO: 4); His-(D-Phe)-Arg-Trp (SEQ ID NO: 5); His-Phe-(D-Arg)-Trp (SEQ ID NO: 6); His-Phe-Arg-(D-Trp) (SEQ ID NO: 7); His-(D-Phe)-Arg-(D-Trp) (SEQ ID NO: 8); His-Nal-Arg-Trp (SEQ ID NO: 9) and His-(D-Nal)-Arg-Trp (SEQ ID NO: 10); and wherein Z is selected from the group consisting of Arg-Phe-Gly, Arg-(D-Phe)-Gly, Arg-Phe and Arg-(D-Phe); and Phe or (D-Phe) is phenylalanine amide or Gly is glycine amide.

In one embodiment $(aa_1)_n$ is selected from the group consisting of Tyr-Val-Met-Gly (SEQ ID NO: 14) and Tyr-Val-Nle-Gly (SEQ ID NO: 15). In one embodiment $(aa_2)_m$ is Asp.

In one embodiment the melanocortin analogue of the present invention comprises one or more branched amino acid probes and a γ1-MSH peptide selected from the group consisting of

```
                                            (SEQ ID NO: 2)
Tyr-Val-Met-Gly-His-Phe-Arg-Trp-Asp-Arg-Phe-Gly, (SEQ ID NO: 57)
Tyr-Val-Met-Gly-His-(D-Phe)-Arg-Trp-Asp-Arg-Phe-
Gly, (SEQ ID NO: 58)
Tyr-Val-Met-Gly-His-Phe-(D-Arg)-Trp-Asp-Arg-Phe-
Gly, (SEQ ID NO: 59)
Tyr-Val-Met-Gly-His-Phe-Arg-(D-Trp)-Asp-Arg-Phe-
Gly, (SEQ ID NO: 60)
Tyr-Val-Met-Gly-His-(D-Phe)-Arg-(D-Trp)-Asp-Arg-
Phe-Gly, (SEQ ID NO: 61)
Tyr-Val-Met-Gly-His-Nal-Arg-Trp-Asp-Arg-Phe-Gly, (SEQ ID NO: 62)
Tyr-Val-Met-Gly-His-(D-Nal)-Arg-Trp-Asp-Arg-Phe-
Gly, (SEQ ID NO: 63)
Tyr-Val-Met-Gly-His-Phe-Arg-Trp-Asp-Arg-(D-Phe)-
Gly, (SEQ ID NO: 64)
Tyr-Val-Met-Gly-His-(D-Phe)-Arg-Trp-Asp-Arg-
(D-Phe)-Gly, (SEQ ID NO: 65)
Tyr-Val-Met-Gly-His-Phe-(D-Arg)-Trp-Asp-Arg-
(D-Phe)-Gly, (SEQ ID NO: 66)
Tyr-Val-Met-Gly-His-Phe-Arg-(D-Trp)-Asp-Arg-
(D-Phe)-Gly, (SEQ ID NO: 67)
Tyr-Val-Met-Gly-His-(D-Phe)-Arg-(D-Trp)-Asp-Arg-
(D-Phe)-Gly, (SEQ ID NO: 68)
Tyr-Val-Met-Gly-His-Nal-Arg-Trp-Asp-Arg-(D-Phe)-
Gly, (SEQ ID NO: 69)
Tyr-Val-Met-Gly-His-(D-Nal)-Arg-Trp-Asp-Arg-(D-
Phe)-Gly, (SEQ ID NO: 70)
Tyr-Val-Nle-Gly-His-Phe-Arg-Trp-Asp-Arg-Phe-Gly,
```

(SEQ ID NO: 71)
Tyr-Val-Nle-Gly-His-(D-Phe)-Arg-Trp-Asp-Arg-Phe-Gly, (SEQ ID NO: 72)
Tyr-Val-Nle-Gly-His-Phe-(D-Arg)-Trp-Asp-Arg-Phe-Gly, (SEQ ID NO: 73)
Tyr-Val-Nle-Gly-His-Phe-Arg-(D-Trp)-Asp-Arg-Phe-Gly, (SEQ ID NO: 74)
Tyr-Val-Nle-Gly-His-(D-Phe)-Arg-(D-Trp)-Asp-Arg-Phe-Gly, (SEQ ID NO: 75)
Tyr-Val-Nle-Gly-His-Nal-Arg-Trp-Asp-Arg-Phe-Gly, (SEQ ID NO: 76)
Tyr-Val-Nle-Gly-His-(D-Nal)-Arg-Trp-Asp-Arg-Phe-Gly, (SEQ ID NO: 77)
Tyr-Val-Nle-Gly-His-Phe-Arg-Trp-Asp-Arg-(D-Phe)-Gly, (SEQ ID NO: 78)
Tyr-Val-Nle-Gly-His-(D-Phe)-Arg-Trp-Asp-Arg-(D-Phe)-Gly, (SEQ ID NO: 79)
Tyr-Val-Nle-Gly-His-Phe-(D-Arg)-Trp-Asp-Arg-(D-Phe)-Gly,, (SEQ ID NO: 80)
Tyr-Val-Nle-Gly-His-Phe-Arg-(D-Trp)-Asp-Arg-(D-Phe)-Gly, (SEQ ID NO: 81)
Tyr-Val-Nle-Gly-His-(D-Phe)-Arg-(D-Trp)-Asp-Arg-(D-Phe)-Gly, (SEQ ID NO: 82)
Tyr-Val-Nle-Gly-His-Nal-Arg-Trp-Asp-Arg-(D-Phe)-Gly, and (SEQ ID NO: 83)
Tyr-Val-Nle-Gly-His-(D-Nal)-Arg-Trp-Asp-Arg-(D-Phe)-Gly, wherein the most carboxy terminal Gly is optionally glycine amide.

In one embodiment the melanocortin analogue of the present invention comprises one or more branched amino acid probes and a γ2-MSH peptide selected from the group consisting of (SEQ ID NO: 3)
Tyr-Val-Met-Gly-His-Phe-Arg-Trp-Asp-Arg-Phe, (SEQ ID NO: 84)
Tyr-Val-Met-Gly-His-(D-Phe)-Arg-Trp-Asp-Arg-Phe, (SEQ ID NO: 85)
Tyr-Val-Met-Gly-His-Phe-(D-Arg)-Trp-Asp-Arg-Phe, (SEQ ID NO: 86)
Tyr-Val-Met-Gly-His-Phe-Arg-(D-Trp)-Asp-Arg-Phe, (SEQ ID NO: 87)
Tyr-Val-Met-Gly-His-(D-Phe)-Arg-(D-Trp)-Asp-Arg-Phe, (SEQ ID NO: 88)
Tyr-Val-Met-Gly-His-Nal-Arg-Trp-Asp-Arg-Phe, (SEQ ID NO: 89)
Tyr-Val-Met-Gly-His-(D-Nal)-Arg-Trp-Asp-Arg-Phe, (SEQ ID NO: 90)
Tyr-Val-Met-Gly-His-Phe-Arg-Trp-Asp-Arg-(D-Phe), (SEQ ID NO: 91)
Tyr-Val-Met-Gly-His-(D-Phe)-Arg-Trp-Asp-Arg-(D-Phe), (SEQ ID NO: 92)
Tyr-Val-Met-Gly-His-Phe-(D-Arg)-Trp-Asp-Arg-(D-Phe), (SEQ ID NO: 93)
Tyr-Val-Met-Gly-His-Phe-Arg-(D-Trp)-Asp-Arg-(D-Phe), (SEQ ID NO: 94)
Tyr-Val-Met-Gly-His-(D-Phe)-Arg-(D-Trp)-Asp-Arg-(D-Phe), (SEQ ID NO: 95)
Tyr-Val-Met-Gly-His-Nal-Arg-Trp-Asp-Arg-(D-Phe), (SEQ ID NO: 96)
Tyr-Val-Met-Gly-His-(D-Nal)-Arg-Trp-Asp-Arg-(D-Phe), (SEQ ID NO: 97)
Tyr-Val-Nle-Gly-His-Phe-Arg-Trp-Asp-Arg-Phe, (SEQ ID NO: 98)
Tyr-Val-Nle-Gly-His-(D-Phe)-Arg-Trp-Asp-Arg-Phe, (SEQ ID NO: 99)
Tyr-Val-Nle-Gly-His-Phe-(D-Arg)-Trp-Asp-Arg-Phe, (SEQ ID NO: 100)
Tyr-Val-Nle-Gly-His-Phe-Arg-(D-Trp)-Asp-Arg-Phe, (SEQ ID NO: 101)
Tyr-Val-Nle-Gly-His-(D-Phe)-Arg-(D-Trp)-Asp-Arg-Phe, (SEQ ID NO: 102)
Tyr-Val-Nle-Gly-His-Nal-Arg-Trp-Asp-Arg-Phe, (SEQ ID NO: 103)
Tyr-Val-Nle-Gly-His-(D-Nal)-Arg-Trp-Asp-Arg-Phe, (SEQ ID NO: 104)
Tyr-Val-Nle-Gly-His-Phe-Arg-Trp-Asp-Arg-(D-Phe), (SEQ ID NO: 105)
Tyr-Val-Nle-Gly-His-(D-Phe)-Arg-Trp-Asp-Arg-(D-Phe), (SEQ ID NO: 106)
Tyr-Val-Nle-Gly-His-Phe-(D-Arg)-Trp-Asp-Arg-(D-Phe), (SEQ ID NO: 107)
Tyr-Val-Nle-Gly-His-Phe-Arg-(D-Trp)-Asp-Arg-(D-Phe), (SEQ ID NO: 108)
Tyr-Val-Nle-Gly-His-(D-Phe)-Arg-(D-Trp)-Asp-Arg-(D-Phe), (SEQ ID NO: 109)
Tyr-Val-Nle-Gly-His-Nal-Arg-Trp-Asp-Arg-(D-Phe), and (SEQ ID NO: 110)
Tyr-Val-Nle-Gly-His-(D-Nal)-Arg-Trp-Asp-Arg-(D-Phe), wherein the most carboxy terminal Phe or (D-Phe) is optionally a Phenylalanine amide.

In one embodiment the melanocortin analogue of the present invention comprises one or more branched amino acid probes and a cyclic lactam analogue of α-MSH, in one embodiment a side-chain cyclic lactam analogue of α-MSH.

In one embodiment the cyclic lactam analogue of α-MSH is selected from the group consisting of Ac-Nle-cyclo[Asp-His-D-Phe-Arg-Trp-Lys]-NH$_2$ (SEQ ID NO: 111) (MT-II, Melanotan II); SHU9005, SHU9119, [DNal(1')]-MTII, [Nal(2')]-MTII, a cyclic α-MSH(1-13) lactam analog; a side-chain cyclic lactam analogue of a fragment of α-MSH; a cyclic α-MSH(4-10) lactam analogue; MBX36; MBX37; Ac-Nle4-cyclo[Asp5, D-Phe7,Lys10] α-MSH-(4-10)-NH$_2$; cyclic disulphide α-MSH (4-10) analogue; a cyclic α-MSH (4-11) lactam analogue; Ac-[Nle4,D-Orn5,Glu8]alpha-MSH4-11-NH; Ac-[Nle4,D-Orn5,D-Phe7,Glu8]alpha-MSH4-11-NH$_2$; [N-Acetyl-Cys4,D-Phe7,Cys10]-α-MSH (4-13), cyclic; or variants thereof.

In one embodiment the melanocortin analogue of the present invention comprises one or more branched amino acid probes and a metal-cyclized α-MSH analogue; in one embodiment 1,4,7,10-tetraazacyclododecane-1,4,7,10-tetraacetic acid (DOTA) coupled ReO-cyclized [Cys3,4,10,-D-Phe7]-MSH3-13 (DOTA-ReCCMSH).

In one embodiment the melanocortin analogue of the present invention comprises one or more branched amino acid probes and a disulfide bridge providing a cyclized derivative of α-MSH, such as in one embodiment MBJ-06 (WO1998027113).

Disclaimer

In one particular embodiment, the peptide analogue of the present invention does not comprise an α-MSH and γ-MSH analogue as disclosed in PCT/EP2013/071935.

In one embodiment, the present peptide analogue does not comprise an α-MSH and/or a γ-MSH peptide, or variants thereof.

In one embodiment, the present peptide analogue comprises a peptide other than an α-MSH and/or a γ-MSH peptide, or variants thereof.

In one embodiment the peptide analogue does not comprise an α-MSH and/or γ-MSH peptide having a branched amino acid probe covalently linked (or linked by a peptide bond) to the most N-terminal amino acid of said α-MSH and/or γ-MSH peptide.

In one embodiment the peptide analogue does not comprise an α-MSH and/or γ-MSH peptide having a branched amino acid probe, which probe comprises at least one lysine residue, wherein said branched amino acid probe is covalently linked to the most N-terminal amino acid of said α-MSH and/or γ-MSH peptide.

The most N-terminal amino acid of α-MSH is Ser (underlined: Ser-Tyr-Ser-Met-Glu-His-Phe-Arg-Trp-Gly-Lys-Pro-Val (SEQ ID NO: 1).

The most N-terminal amino acid of γ-MSH is Tyr (underlined: Tyr-Val-Met-Gly-His-Phe-Arg-Trp-Asp-Arg-Phe(-Gly) (SEQ ID NO: 2)

In one embodiment wherein the peptide analogue of the invention comprises one (1) branched amino acid probe, wherein one or more (or at least one) of the amino-alkyl amino acid residues of the branched amino acid probe is lysine, and wherein the peptide is α-MSH and/or γ-MSH, or variants thereof, said branched amino acid probe is not attached to the N-terminus of said peptide.

In one embodiment the first amino-alkyl amino acid residue(s) of the one or more branched amino acid probes is not covalently linked to the N-terminus of said peptide, provided i) said peptide analogues comprise one (1) branched amino acid probe, ii) said branched amino acid probe comprises one or more lysine residues, and/or iii) said peptide analogue comprise a melanocortin peptide selected from the group consisting of α-MSH and γ-MSH (comprising γ1-MSH and γ-MSH).

In one embodiment the peptide analogue of the invention does not comprise or include:

A peptide consisting of from 8 to 22 amino acid residues comprising the amino acid sequence: X-(aa$_1$)$_n$-Y-(aa$_2$)$_m$-Z wherein X comprises a branched amino acid probe having a first lysine residue (Lys$_1$) selected from Lys and D-Lys, said first lysine residue being linked by a peptide bond to (aa$_1$)$_n$, said first lysine residue being optionally linked by peptide bonds to a second lysine residue (Lys$_1$), or to a second and third lysine residue (Lys$_3$), to form a linear chain of a total of 2 or 3 lysine residues selected from Lys and D-Lys, wherein the side chain(s) of one or more of each of said first, second and/or third lysine residues are modified by attaching to the ε-amino group of said one or more of each of said lysine residues a molecule independently selected from the group consisting of Lys$_q$-Lys (SEQ ID NO: 117); (aa$_3$)$_p$-Lys$_q$ (SEQ ID NOs: 119-124); Lys$_q$-(aa$_3$)$_p$ (SEQ ID NOs: 125-130);[(aa$_3$)-Lys]$_p$ (SEQ ID NOs: 131 and 132) and [Lys-(aa$_3$)]$_p$ (SEQ ID NOs: 133 and 134), wherein q is a number selected from 0, 1, 2 and 3; p is a number selected from 1, 2 and 3, and (aa$_3$) is an amino acid residue independently selected from Arg, His, Gly and Ala, with the proviso that X consists of from 2 to 9 amino acid residues, wherein Y comprises an amino acid sequence consisting of 4 contiguous amino acid residues selected from the group consisting of His-Phe-Arg-Trp (SEQ ID NO: 4); His-(D-Phe)-Arg-Trp (SEQ ID NO: 5); His-Phe-(D-Arg)-Trp (SEQ ID NO: 6); His-Phe-Arg-(D-Trp) (SEQ ID NO: 7); His-(D-Phe)-Arg-(D-Trp) (SEQ ID NO: 8); His-Nal-Arg-Trp (SEQ ID NO: 9) and His-(D-Nal)-Arg-Trp (SEQ ID NO: 10); and wherein Z comprises an amino acid sequence consisting of 2 or 3 contiguous amino acid residues selected from the group consisting of Lys-Pro-Val; Lys-Pro-(D-Val); Arg-Phe-Gly; Arg-(D-Phe)-Gly; Arg-Phe and Arg-(D-Phe); and wherein n is a number selected from 0, 1, 2, 3, 4 and 5, and (aa$_1$) independently can be any natural or unnatural amino acid residue, and wherein m is 0 or 1, and (aa$_2$) can be any natural or unnatural amino acid residue.

In one embodiment the peptide analogue of the invention does not comprise or include:

A peptide consisting of from 8 to 22 amino acid residues comprising the amino acid sequence: X-(aa$_1$)$_n$-Y-(aa$_2$)$_m$-Z wherein X comprises a branched amino acid probe having a first lysine residue (Lys$_1$) selected from Lys and D-Lys, said first lysine residue being linked by a peptide bond to (aa$_1$)$_n$, said first lysine residue being optionally linked by peptide bonds to a second lysine residue (Lys$_1$), or to a second and third lysine residue (Lys$_3$), to form a linear chain of a total of 2 or 3 lysine residues selected from Lys and D-Lys, wherein the side chain(s) of one or more of each of said first, second and/or third lysine residues are modified by attaching to the ε-amino group of said one or more of each of said lysine residues a molecule independently selected from the group consisting of Lys$_q$-Lys (SEQ ID NO: 117); (aa$_3$)$_p$-Lys$_q$ (SEQ ID NOs: 119-124); Lys$_q$-(aa$_3$)$_p$ (SEQ ID NOs: 125-130);[(aa$_3$)-Lys]$_p$ (SEQ ID NOs: 131 and 132) and [Lys-(aa$_3$)]$_p$ (SEQ ID NOs: 133 and 134), wherein q is a number selected from 0, 1, 2 and 3; p is a number selected from 1, 2 and 3, and (aa$_3$) is an amino acid residue independently selected from Arg, His, Gly and Ala, with the proviso that X consists of from 2 to 9 amino acid residues, wherein Y comprises an amino acid sequence consisting of 4 contiguous amino acid residues selected from the group consisting of His-Phe-Arg-Trp (SEQ ID NO: 4); His-(D-Phe)-Arg-Trp (SEQ ID NO: 5); His-Phe-(D-Arg)-Trp (SEQ ID NO: 6); His-Phe-Arg-(D-Trp) (SEQ ID NO: 7); His-(D-Phe)-Arg-(D-Trp) (SEQ ID NO: 8); His-Nal-Arg-Trp (SEQ ID NO: 9) and His-(D-Nal)-Arg-Trp (SEQ ID NO: 10); and wherein Z comprises an amino acid sequence consisting of 2 or 3 contiguous amino acid residues selected from the group consisting of Lys-Pro-Val; Lys-Pro-(D-Val); Arg-Phe-Gly; Arg-(D-Phe)-Gly; Arg-Phe and Arg-(D-Phe); and wherein $(aa_1)_n$ is selected from the group consisting of Ser-Tyr-Ser-Met-Glu (SEQ ID NO: 11), Ser-Tyr-Ser-Nle-Glu (SEQ ID NO: 12), Ser-Ser-Ile-Ile-Ser (SEQ ID NO: 13), Tyr-Val-Met-Gly (SEQ ID NO: 14) and Tyr-Val-Nle-Gly (SEQ ID NO: 15); and wherein $(aa_2)_m$ is selected from the group consisting of Gly and Asp.

Methods of Preparation

The peptide analogues according to the present invention may be prepared by any suitable methods known in the art. Thus, in some embodiments the peptide and the branched amino acid probe are each prepared by standard peptide-preparation techniques, such as solution synthesis or solid phase peptide synthesis (SPPS) such as Merrifield-type solid phase synthesis.

The peptide analogues of the invention are in one embodiment prepared by solid phase synthesis by first constructing the pharmacologically active peptide sequence, using well-known standard protection, coupling and de-protection procedures, thereafter sequentially coupling the branched amino acid probe onto the active peptide in a manner similar to the construction of the active peptide, and finally cleaving off the entire peptide analogue from the carrier. This strategy yields a peptide, wherein the branched amino acid probe is covalently bound to the pharmacologically active peptide at the N-terminal nitrogen atom of the peptide.

In one embodiment, the alpha nitrogen on the final amino acid in the branched amino acid sequence is capped with acetyl, using standard acylation techniques, prior to or after coupling of the branched amino acid sequence on the active peptide.

Reactive moieties at the N- and C-termini, which facilitates amino acid coupling during synthesis, as well as reactive side chain functional groups, can interact with free termini or other side chain groups during synthesis and peptide elongation and negatively influence yield and purity. Chemical groups are thus developed that bind to specific amino acid functional groups and block, or protect, the functional group from nonspecific reactions. Purified, individual amino acids are reacted with these protecting groups prior to synthesis and then selectively removed during specific steps of peptide synthesis. Examples of N-terminal protecting groups are t-Boc and Fmoc, commonly used in solid-phase peptide synthesis. C-terminal protecting groups are mostly used in liquid-phase synthesis. Because N-terminal deprotection occurs continuously during peptide synthesis, protecting schemes have been established in which the different types of side chain protecting groups (benzyl; Bzl or tert-butyl;tBu) are matched to either Boc or Fmoc, respectively, for optimized deprotection.

In a particular embodiment of the invention, when preparing the branched amino acid probe, exemplified by Ac(Ac-Lys-Lys)Lys-, the protection group for Lys is Mtt, which protected amino acid is commercially available (Fmoc-Lys(Mtt)-OH; N-α-Fmoc-N-ε-4-methyltrityl-L-lysine, CAS #167393-62-6). Lys(Mtt) allows for capping Lys with acetyl as it is not cleaved under the conditions that cleave Fmoc, and may be removed without cleavage of other side chain protection groups.

The method of preparation is in some embodiments optimized by routine methods in the art that may increase the yield and/or quality of the thus prepared synthetic peptide. For instance, use of pseudoproline (oxazolidine) dipeptides in the Fmoc SPPS of serine- and threonine-containing peptides may lead to improvements in quality and yield of crude products and may help avoid unnecessary repeat synthesis of failed sequences. These dipeptides are easy to use: simply substitute a serine or threonine residue together with the preceding amino acid residue in the peptide sequence with the appropriate pseudoproline dipeptide. The native sequence is regenerated on cleavage and deprotection.

In one embodiment the sequence of the pharmacologically active peptide and the branched amino acid probe (or parts thereof) are each prepared separately by for example solution synthesis, solid phase synthesis, recombinant techniques, or enzymatic synthesis, followed by coupling of the (at least) two sequences by well-known segment condensation procedures, either in solution or using solid phase techniques, or a combination thereof.

In one embodiment, the peptides are prepared by recombinant DNA methods and the branched amino acid probe is prepared by solid or solution phase synthesis. The conjugation of the peptide and the branched amino acid probe is in one embodiment carried out by using chemical ligation. This technique allows for the assembling of totally unprotected peptide segments in a highly specific manner. In another embodiment, the conjugation is performed by protease-catalysed peptide bond formation, which offers a highly specific technique to combine totally unprotected peptide segments via a peptide bond.

In one embodiment, the C-terminal amino acid of the branched amino acid probe or the C-terminal amino acid of the peptide is attached to the solid support material by means of a common linker such as 2,4-dimethoxy-4'-hydroxy-benzophenone, 4-(4-hydroxy-methyl-3-methoxyphenoxy)-butyric acid, 4-hydroxy-methylbenzoic acid, 4-hydroxymethyl-phenoxyacetic acid, 3-(4-hydroxymethylphenoxy) propionic acid, or p-{(R,S)-α-[1-(9H-Fluoren-9-yl)-methoxyformamido]-2,4-dimethoxybenzyl}-phenoxyacetic acid (Rink amide linker).

Examples of suitable solid support materials (SSM) are e.g., functionalised resins such as polystyrene, polyacrylamide, polydimethylacrylamide, polyethyleneglycol, cellulose, polyethylene, polyethyleneglycol grafted on polystyrene, latex, dynabeads, etc.

The produced peptide analogues of the invention are in some embodiment cleaved from the solid support material by means of an acid such as trifluoracetic acid, trifluoromethanesulfonic acid, hydrogen bromide, hydrogen chloride, hydrogen fluoride, etc. optionally in combination with one phenol, thioanisole, etc., or the peptide conjugate of the invention are in other embodiments cleaved from the solid support by means of a base such as ammonia, hydrazine, an alkoxide, such as sodium ethoxide, an hydroxide, such as sodium hydroxide, etc.

In other embodiments, the peptide analogues of the invention may be prepared or produced by recombinant techniques. Thus, in one aspect of the present invention the peptide is produced by host cells comprising a first nucleic acid sequence encoding the peptide or peptide analogue operably associated with a second nucleic acid capable of directing expression in said host cells. In some embodiments the second nucleic acid sequence comprises or even consists of a promoter that will direct the expression of protein of interest in said cells. A skilled person will be readily capable of identifying useful second nucleic acid sequences (e.g. vectors and plasmids) for use in a given host cell.

The process of producing a recombinant peptide in general comprises the steps of: providing a host cell, preparing a gene expression construct comprising a first nucleic acid encoding the peptide operably linked to a second nucleic acid capable of directing expression of said protein of interest in the host cell, transforming the host cell with the construct and cultivating the host cell, thereby obtaining expression of the peptide. In one embodiment of the invention, the recombinantly produced peptide is excreted by the host cells. The host cell include any suitable host cell known in the art, including prokaryotic cells, yeast cells, insect cells and mammalian cells.

In one embodiment, the recombinant peptide thus produced is isolated by any conventional method and may be linked via conventional peptide bond forming chemistry to any suitably protected branched amino peptide moiety. The skilled person will be able to identify suitable protein isolation steps for purifying the peptide.

Methods of Treatment

It is an aspect to provide peptide analogues as defined according to the present invention for use as a medicament.

In another aspect, the present invention provides methods for treatment, prevention or alleviation of a medical condition. Such methods according to the present invention in one embodiment comprise one or more steps of administration or release of an effective amount of a peptide analogue according to the present invention, or a pharmaceutical composition comprising one or more such peptides, to an individual in need thereof. In one embodiment, such steps of administration or release according to the present invention are simultaneous, sequential or separate.

An individual in need as referred to herein, is in one embodiment an individual that benefits from the administration of a peptide or pharmaceutical composition according to the present invention. Such an individual in one embodiment suffers from a disease or condition or is at risk of suffering therefrom. The individual is in one embodiment any human being, male or female, infant, middle-aged or old. The disorder to be treated or prevented in the individual in one embodiment relates to the age of the individual, the general health of the individual, the medications used for treating the individual and whether or not the individual has a prior history of suffering from diseases or disorders that may have or have induced the condition in the individual.

The terms "treatment" and "treating" as used herein refer to the management and care of a patient for the purpose of combating a condition, disease or disorder. The term is intended to include the full spectrum of treatments for a given condition from which the patient is suffering, such as administration of the peptide analogue for the purpose of: alleviating or relieving symptoms or complications; delaying the progression of the condition, partially arresting the clinical manifestations, disease or disorder; curing or eliminating the condition, disease or disorder; and/or preventing or reducing the risk of acquiring the condition, disease or disorder, wherein "preventing" or "prevention" is to be understood to refer to the management and care of a patient for the purpose of hindering the development of the condition, disease or disorder, and includes the administration of the active compounds to prevent or reduce the risk of the onset of symptoms or complications. The patient to be treated is preferably a mammal, in particular a human being. Treatment of animals, such as mice, rats, dogs, cats, cows, horses, sheep and pigs, is, however, also within the scope of the present invention. The patients to be treated according to the present invention can be of various ages, for example, adults, children, children under 16, children age 6-16, children age 2-16, children age 2 months to 6 years or children age 2 months to 5 years.

The invention is in one embodiment directed to a peptide analogue according to the present invention for use in the treatment of an ischemic condition, an inflammatory condition and/or a metabolic condition.

The invention is in one embodiment directed to a method for treatment of an ischemic condition, an inflammatory condition and/or a metabolic condition, said method comprising administering an effective amount of a peptide analogue according to the present invention to an individual in need thereof.

Further Active Ingredients

In some embodiments, the peptide analogues of the present invention are combined with or comprise one or more further active ingredients which are understood as other therapeutical compounds or pharmaceutically acceptable derivatives thereof.

Methods for treatment according to the present invention in one embodiment thus further comprise one or more steps of administration of one or more further active ingredients, either concomitantly or sequentially, and in any suitable ratios.

Methods of treatment according to the present invention in one embodiment include a step wherein the pharmaceutical composition or peptide analogue as defined herein is administered simultaneously, sequentially or separately in combination with one or more further active ingredients.

Administration and Dosage

According to the present invention, a composition comprising a peptide analogue as defined herein is in one embodiment administered to individuals in need thereof in pharmaceutically effective doses or a therapeutically effective amount.

A therapeutically effective amount of a peptide according to the present invention is in one embodiment an amount sufficient to cure, prevent, reduce the risk of, alleviate or partially arrest the clinical manifestations of a given disease or disorder and its complications. The amount that is effective for a particular therapeutic purpose will depend on the severity and the sort of the disorder as well as on the weight and general state of the subject. An amount adequate to accomplish this is defined as a "therapeutically effective amount".

In one embodiment of the present invention, the composition is administered in doses of from 1 µg/day to 100 mg/day; such as from 1 µg/day to 10 µg/day, such as 10 µg/day to 100 µg/day, such as 100 µg/day to 250 µg/day, such as 250 µg/day to 500 µg/day, such as 500 µg/day to 750 µg/day, such as 750 µg/day to 1 mg/day, such as 1 mg/day to 2 mg/day, such as 2 mg/day to 5 mg/day, or such as 5 mg/day to 10 mg/day, such as 10 mg/day to 20 mg/day, such as 20 mg/day to 30 mg/day, such as 30 mg/day to 40 mg/day, such as 40 mg/day to 50 mg/day, such as 50 mg/day to 75 mg/day, or such as 75 mg/day to 100 mg/day.

In one embodiment of the present invention, one single dose of the composition is administered and may comprise of from 1 µg/kg body weight to 100 mg/kg body weight; such as from 1 to 10 µg/kg body weight, such as 10 to 100 µg/day, such as 100 to 250 µg/kg body weight, such as 250 to 500 µg/kg body weight, such as 500 to 750 µg/kg body weight, such as 750 µg/kg body weight to 1 mg/kg body weight, such as 1 mg/kg body weight to 2 mg/kg body weight, such as 2 to 5 mg/kg body weight, such as 5 to 10 mg/kg body weight, such as 10 to 20 mg/kg body weight, such as 20 to 30 mg/kg body weight, such as 30 to 40 mg/kg body weight, such as 40 to 50 mg/kg body weight, such as 50 to 75 mg/kg body weight, or such as 75 to 100 mg/kg body weight.

In one embodiment, a dose according to the present invention is administered one or several times per day, such as from 1 to 6 times per day, such as from 1 to 5 times per day, such as from 1 to 4 times per day, such as from 1 to 3 times per day, such as from 1 to 2 times per day, such as from 2 to 4 times per day, such as from 2 to 3 times per day.

Routes of Administration

It will be appreciated that the preferred route of administration will depend on the general condition and age of the subject to be treated, the nature of the condition to be treated, the location of the tissue to be treated in the body and the active ingredient chosen.

Systemic Treatment

In one embodiment, the route of administration allows for introducing the peptide analogue into the blood stream to ultimately target the sites of desired action.

In one embodiment the routes of administration is any suitable routes, such as an enteral route (including the oral, rectal, nasal, pulmonary, buccal, sublingual, transdermal, intracisternal and intraperitoneal administration), and/or a parenteral route (including subcutaneous, intramuscular, intrathecal, intravenous and intradermal administration).

Appropriate dosage forms for such administration may be prepared by conventional techniques.

Parenteral Administration

Parenteral administration is any administration route not being the oral/enteral route whereby the medicament avoids first-pass degradation in the liver. Accordingly, parenteral administration includes any injections and infusions, for example bolus injection or continuous infusion, such as intravenous administration, intramuscular administration or subcutaneous administration. Furthermore, parenteral administration includes inhalations and topical administration.

Accordingly, the peptide analogue or composition is in one embodiment administered topically to cross any mucosal membrane of an animal to which the substance or peptide is to be given, e.g. in the nose, vagina, eye, mouth, genital tract, lungs, gastrointestinal tract, or rectum, for example the mucosa of the nose, or mouth, and accordingly, parenteral administration may also include buccal, sublingual, nasal, rectal, vaginal and intraperitoneal administration as well as pulmonal and bronchial administration by inhalation or installation. In some embodiments, the peptide analogue is administered topically to cross the skin.

In one embodiment, the intravenous, subcutaneous and intramuscular forms of parenteral administration are employed.

Local Treatment

In one embodiment, the peptide analogue or composition according to the invention is used as a local treatment, i.e. is introduced directly to the site(s) of action. Accordingly, the peptide may be applied to the skin or mucosa directly, or the peptide may be injected into the site of action, for example into the diseased tissue or to an end artery leading directly to the diseased tissue.

Pharmaceutical Formulations

In one embodiment the peptide analogues or pharmaceutically acceptable derivatives thereof are administered alone or in combination with pharmaceutically acceptable carriers or excipients, in either single or multiple doses. The pharmaceutical compositions or compounds according to the invention may be formulated with pharmaceutically acceptable carriers or diluents as well as any other known adjuvants and excipients in accordance with conventional techniques, such as those disclosed in Remington: The Science and Practice of Pharmacy, 20$^{th}$ Edition, Gennaro, Ed., Mack Publishing Co., Easton, Pa., 2000.

The term "pharmaceutically acceptable derivative" in present context includes pharmaceutically acceptable salts, which indicate a salt which is not harmful to the patient. Such salts include pharmaceutically acceptable basic or acid addition salts as well as pharmaceutically acceptable metal salts, ammonium salts and alkylated ammonium salts. A pharmaceutically acceptable derivative further includes pharmaceutically acceptable esters, prodrugs, or other precursors of a compound which may be biologically metabolized into the active compound, or crystal forms of a compound.

The pharmaceutical composition or pharmaceutically acceptable composition may be specifically formulated for administration by any suitable route, such as an enteral route, the oral, rectal, nasal, pulmonary, buccal, sublingual, transdermal, intracisternal, intraperitoneal, and parenteral (including subcutaneous, intramuscular, intrathecal, intravenous and intradermal) route.

In an embodiment of the present invention, the pharmaceutical compositions or peptides of the present invention are formulated for crossing the blood-brain-barrier.

Pharmaceutical compositions for oral administration include solid dosage forms such as hard or soft capsules, tablets, troches, dragees, pills, lozenges, powders and granules. Where appropriate, they can be prepared with coatings such as enteric coatings, or they can be formulated so as to provide controlled release of the active ingredient, such as sustained or prolonged release, according to methods well known in the art. In the same solid dosage form two active ingredients may be combined so as to provide controlled release of one active ingredient and immediate release of another active ingredient.

Liquid dosage forms for oral administration include solutions, emulsions, aqueous or oily suspensions, syrups and elixirs.

Pharmaceutical compositions for parenteral administration include sterile aqueous and non-aqueous injectable solutions, dispersions, suspensions or emulsions, as well as sterile powders to be reconstituted in sterile injectable solutions or dispersions prior to use. Depot injectable formulations are also regarded as being within the scope of the present invention.

Other suitable administration forms include suppositories, sprays, ointments, cremes/lotions, gels, inhalants, dermal patches, implants, etc.

In one embodiment, a compound or peptide for use according to the present invention is generally utilized as the free substance or as a pharmaceutically derivative such as a pharmaceutically acceptable ester or such as a salt thereof. Examples of the latter are: an acid addition salt of a compound having a free base functionality, and a base addition salt of a compound having a free acid functionality. The term "pharmaceutically acceptable salt" refers to a non-toxic salt of a compound for use according to the present invention, which salts are generally prepared by reacting a free base with a suitable organic or inorganic acid, or by reacting an acid with a suitable organic or inorganic base. When a compound for use according to the present invention contains a free base functionality, such salts are prepared in a conventional manner by treating a solution or suspension of the compound with a chemical equivalent of a pharmaceutically acceptable acid. When a compound for use according to the present invention contains a free acid functionality, such salts are prepared in a conventional manner by treating a solution or suspension of the compound with a chemical equivalent of a pharmaceutically acceptable base. Physiologically acceptable salts of a compound with a hydroxy group include the anionic form of the compound in combination with a suitable cation, such as sodium or ammonium ion. Other salts which are not pharmaceutically acceptable may be useful in the preparation of compounds of the invention, and these form a further aspect of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, trifluoroacetate, trichloroacetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts.

In one embodiment of the present invention, the peptides of the present invention are on crystalline forms, for example co-crystallized forms or hydrates of crystalline forms.

The term "prodrug" refers to peptides that are rapidly transformed in vivo to yield the parent compound of the above formulae, for example, by hydrolysis in blood or by metabolism in cells, such as for example the cells of the basal ganglia. A thorough discussion is provided in T. Higuchi and V Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference. Examples of prodrugs include pharmaceutically acceptable, non-toxic esters of the compounds of the present invention. Esters of the compounds of the present invention may be prepared according to conventional methods "March's Advanced Organic Chemistry, 5$^{th}$ Edition". M. B. Smith & J. March, John Wiley & Sons, 2001.

In one embodiment, for parenteral administration, solutions of peptides according to the present invention in sterile aqueous solution, in aqueous propylene glycol or in sesame or peanut oil are employed. Aqueous solutions should be suitably buffered where appropriate, and the liquid diluent rendered isotonic with, e.g., sufficient saline or glucose. Aqueous solutions are particularly suitable for intravenous, intramuscular, subcutaneous and intraperitoneal administration. The sterile aqueous media to be employed are all readily available by standard techniques known to those skilled in the art.

Suitable pharmaceutical carriers include inert solid diluents or fillers, sterile aqueous solutions and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water. Moreover, the carrier or diluent may include any sustained release material known in the art, such as glyceryl monostearate or glyceryl distearate, alone or mixed with a wax. The pharmaceutical compositions formed by combining the compounds according to the present invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units, such as capsules or tablets, which each contain a predetermined amount of the active ingredient, and which may include a suitable excipient.

Furthermore, the orally available formulations may be in the form of a powder or granules, a solution or suspension in an aqueous or non-aqueous liquid, or an oil-in-water or water-in-oil liquid emulsion.

Compositions intended for oral use may be prepared according to any known method, and such compositions may contain one or more agents selected from the group consisting of sweetening agents, flavouring agents, colouring agents and preserving agents in order to provide pharmaceutically elegant and palatable preparations. Tablets may contain the active ingredient(s) in admixture with non-toxic pharmaceutically acceptable excipients which are suitable for the manufacture of tablets. These excipients may, for example, be: inert diluents, such as calcium carbonate, sodium carbonate, lactose, calcium phosphate or sodium phosphate; granulating and disintegrating agents, for example corn starch or alginic acid; binding agents, for example, starch, gelatine or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, the contents of which are incorporated herein by reference, to form osmotic therapeutic tablets for controlled release.

Formulations for oral use may also be presented as hard gelatine capsules where the active ingredient is mixed with an inert solid diluent, for example, calcium carbonate, calcium phosphate or kaolin, or a soft gelatine capsules wherein the active ingredient is mixed with water or an oil medium, for example peanut oil, liquid paraffin, or olive oil.

Aqueous suspensions may contain the compound for use according to the present invention in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavouring, and colouring agents may also be present.

The pharmaceutical compositions comprising peptides for use according to the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agent. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the invention. These compositions can be prepared by mixing the compound with a suitable non-irritating excipient which is solid at ordinary temperatures but liquid at the rectal temperature and will thus melt in the rectum to release the drug. Such materials include, for example, cocoa butter and polyethylene glycols.

Peptides of the present invention may also be administered in the form of liposome delivery systems, such as small unilamellar vesicles, large unilamellar vesicles, and multi-lamellar vesicles. Liposomes may be formed from a variety of phospholipids, such as but not limited to cholesterol, stearylamine or phosphatidylcholines.

In addition, some peptides of the present invention may form solvates with water or common organic solvents. Such solvates are also encompassed within the scope of the invention.

Thus, a further embodiment provides a pharmaceutical composition comprising a peptide for use according to the present invention, or a pharmaceutically acceptable salt, solvate, or prodrug thereof, and one or more pharmaceutically acceptable carriers, excipients, or diluents.

The present invention also encompass pharmaceutical compositions comprising the α-MSH, the γ-MSH analogues, the GLP-1 analogues, the GLP-2 analogues and the analogues of N-terminus of Annexin A1 of the present invention, as well as the α-MSH and γ-MSH analogues, the GLP-1 analogues, the GLP-2 analogues or the analogues and of N-terminus of Annexin A1 of the present invention for use as a medicament.

Specifically, the α-MSH and γ-MSH analogues α-MSH, the γ-MSH analogues, the GLP-1 analogues, the GLP-2 analogues and the analogues of N-terminus of Annexin A1 according to the present invention are potentially suitable for use in the treatment of an ischemic and/or inflammatory condition in the tissue of one or more organs of a mammal, wherein said treatment may be prophylactic, ameliorative or curative.

Said ischemic conditions concerned may in one embodiment be due to or caused by underlying conditions such as stroke, injury, septic shock, systemic hypotension, cardiac arrest due to heart attack, cardiac arrhythmia, atheromatous disease with thrombosis, embolism from the heart or from blood vessel from any organ, vasospasm, aortic aneurysm or aneurisms in other organs, coronary stenosis, myocardial infarction, angina pectoris, pericarditis, myocarditis, myxodemia, or endocarditis.

Further, said ischemic and/or inflammatory condition may in one embodiment be associated with surgery, such as major surgery, wherein said surgery may include cardiothoracic surgery, abdominal surgery, surgery on the aorta and/or other major blood vessels, repair of one or more cardiac valves, cardiac artery bypass grafting (CABG), surgery on the aortic root or the aortic branch including the common carotid arteries, and combined cardiac surgery such as valve(s) replacement and CABG and/or aortic root surgery.

Furthermore, said ischemic and/or inflammatory condition may in one embodiment be associated with organ transplantation, such as solid organ transplantation, including heart transplantation, lung transplantation, combined heart and lung transplantation, liver transplantation and kidney transplantation.

In one embodiment, said ischemic and/or inflammatory condition is post-surgical systemic inflammatory response syndrome (SIRS) or post-surgical organ dysfunction, including post-surgical renal failure such as acute kidney injury (AKI), neprotoxicity and/or chronic renal failure (CRF).

In one embodiment, said ischemic and/or inflammatory condition is reperfusion injury.

Also, said ischemic and/or inflammatory condition may be an inflammatory disease, including but not limited to arthropathy (joint disease), rheumatoid arthritis (RA), gout, inflammatory diseases of the gastrointestinal system, and multiple sclerosis.

In addition to the ischemic and/or inflammatory conditions, the α-MSH and γ-MSH analogues α-MSH, the γ-MSH analogues, the GLP-1 analogues, the GLP-2 analogues and the analogues of N-terminus of Annexin A1 according to the present invention are potentially suitable for use in the treatment of an metabolic condition including Type 1 or Type 2 diabetes mellitus, prediabetic conditions including glucose intolerance, obesity, overweight, metabolic syndrome, gestational diabetes mellitus, or metabolic disease associated with polycystic ovarian syndrome wherein said treatment may be prophylactic, ameliorative or curative.

The modified peptides according to this invention may be used to treat the same diseases and conditions for which the parent peptide has been indicated.

EXAMPLES

Example 1—Synthesis of BAP-Modified α-MSH Peptide Analogues.

```
α-MSH analogue 1:
Ac-(Ac-Lys-Lys-)Lys-Ser-Tyr-Ser-Met-Glu-His-Phe-
Arg-Trp-Gly-Lys-Pro-Val-NH2

γ-MSH analogue 1:
Ac-(Ac-Lys-Lys-)Lys-Tyr-Val-Met-Gly-His-Phe-Arg-
(D-Trp)-Asp-Arg-Phe-Gly-NH2.
```

The peptides are manufactured using Fmoc (9-fluorenylmethyloxycarbonyl) chemistry. Peptides are made using a polystyrene resin, functionalized with an appropriate linker, and the peptides are then manufactured using an Intavis Peptide Synthesizer. A 4-fold excess of amino acid is added relative to the resin and either HATU (O-(7-azabenzotriazol-1-yl)-N,N,N',N'-tetramethyluronium hexafluorophosphate) or HCTU (2-(6-Chloro-1H-benzotriazole-1-yl)-1,1,3,3-tetramethylaminium hexafluorophosphate) were used at a 3.95-fold excess to create the active ester. Along with an 8-fold excess of DIPEA (N,N-Diisopropylethylamine) as the base, these reagents catalyze the addition of the next amino acid. Once the amino acid is coupled (each cycle includes a double coupling cycle to insure efficient coupling) the resin is exposed to 20% acetic anhydride to terminate ("cap-off") any peptide chains that have not added the next amino acid.

The amino acids are dissolved in NMP (N-Methyl-2-pyrrolidone) or DMF (Dimethylformamide) For washing. Piperidine is used to remove the Fmoc group at the end of each coupling cycle which allows the next amino acid to be added.

α-MSH analogue 1 was made with Lys(Mtt) on the end; the peptide was acetylated, the Mtt was removed, added Lys, added Lys and then acetylate again.

For γ-MSH analogue 1 the addition of one or more pseudoproline (oxazolidine) dipeptides during the synthesis of serine- and/or threonine-containing peptides resulted in improvements in peptide quality and an increase in the yield of full length crude peptide. In this case the peptide was made up to the MEHF, a pseudoproline dipeptide (Fmoc-YS) was added, the next amino acid "Ser" was coupled 3 times to insure it went to completion, and the peptide finished manually by adding the Lys(Mtt), acetylating, and then finishing as above.

In each case the peptides were dried using MeOH (3X), DCM (3X), cleaved using 92% TFA, 2% water, 2% triisopropylsilane, 2% thioanisole and 2% ethanedithiol for 3-4 h at room temperature. Peptides were precipitated in cold diethyl ether, centrifuged (2,000 RPM) and the pellets washed 2× with cold ether. After drying the peptides were solubilized in water containing 0.1% TFA (buffer A) and subjected to RP-HPLC using $C_{18}$ columns (buffer B=95% acetonitrile/0.1% TFA).

The purity was determined by analytical HPLC and theoretical mono isotopic molecular masses we confirmed by MS. The sequence integrity was verified by CID tandem MS/MS sequencing.

Example 2: Pharmacological Characterization of BAP-Modified α-MSH Analogues

Method:

Murine B16-F1 cells expressing MCr1 are used for determination of binding affinity to and agonist activity against the MC1r. Human recombinant CHO cells expressing MC3r, MC4r or MC5r are used for determination of affinity to or agonist activity against the MC3r, MC4r and MC5r, respectively. The binding affinity is determined in experiments conducted as described in the procedures for radioligand binding study catalogue no 0644 (MC1r); no 0447 (MC3r); no 0420 (MC3r) and no 0448 (Mc5r) Cerep, France. In all experiments the Ki values are calculated based on the ability of the test compound to displace $^{125}$I-NDP-αMSH. The test items are tested in a concentration range of $10^{-13}$ to $10^{-5}$M.

For agonist activity against the MCRs the following procedures are conducted: The cells are incubated with test item at concentrations from $10^{-13}$ to $10^{-5}$M. In all assays cAMP accumulation is determined after incubation and the response at a given concentration is expressed as a percent of the maximal control specific agonist response (measured specific response/control specific agonist response)×100) when NDP-αMSH is used as positive control. The $EC_{50}$ values (concentration producing a half-maximal specific response) are determined by non-linear regression analysis of the concentration-response curves generated with mean replicate values using Hill equation curve fitting (Y=D+[A−D]/(1±(C/$C_{50}$)nH)], where Y=specific response, D= minimum specific response, A=maximum specific response, C=compound concentration, and $C_{50}$=$EC_{50}$, and nH=slope factor). For further details see the specific protocols for Cerep study protocol no 2147 (MC1r); no 0959 (MC3r), no 0699 (MC4r) and no 1869 (MC5r).

Test Peptide Analogues:

```
Analogue 1:
Ac-(Ac-Lys-Lys)Lys-Ser-Tyr-Ser-Met-Glu-His-Phe-
Arg-Trp-Gly-Lys-Pro-Val-NH₂

Analogue 2:
Ac-(Ac-Lys-Lys)Lys-Ser-Tyr-Ser-Met-Glu-His-Phe-
Arg-Trp-Gly-Lys-Pro-(D-Val)-NH₂

Analogue 3:
Ac-(Ac-Lys-Lys)Lys-Ser-Tyr-Ser-Nle-Glu-His-DPhe-
Arg-Trp-Gly-Lys-Pro-Val-NH₂

Analogue 4:
Ac-(Ac-Lys-Lys)Lys-Ser-Ser-Ile-Ile-Ser-His-DPhe-
Arg-Trp-Gly-Lys-Pro-Val-NH₂

Control peptide:
Control peptide 1 (αMSH):
                                        (SEQ ID NO: 1)
Ac-Ser-Tyr-Ser-Met-Glu-His-Phe-Arg-Trp-Gly-Lys-
Pro-Val-NH₂

Control peptide 2 (NDP-αMSH):
                                       (SEQ ID NO: 30)
Ac-Ser-Tyr-Ser-Nle-Glu-His-DPhe-Arg-Trp-Gly-Lys-
Pro-Val-NH₂
```

Results
Ki values (nM):

|  | MC1r | MC3r | MC4r | MC5r |
| --- | --- | --- | --- | --- |
| Control peptide 1 | 4.6 | 114 | 128 | 404 |
| Control peptide 2 | 1.5 | 8.8 | 7.1 | 14 |
| Analogue 1 | 1.2 | 24 | 26 | 193 |

MCr binding relative to control peptide 1:

|  | MC1r | MC3r | MC4r | MC5r |
| --- | --- | --- | --- | --- |
| Analogue 1 | 4x | 5x | 5x | 2x |
| Analogue 2 |  | 3.3x | 8.5x |  |
| Analogue 3 |  | 41x | 47x |  |
| Analogue 4 | 9.4x | 42x | 53x |  |

$EC_{50}$ values (nM):

|  | MC1r | MC3r | MC4r | MC5r |
| --- | --- | --- | --- | --- |
| Control peptide 1 | 13 | 62 | 28 | 1104 |
| Control peptide 2 | 15 | 24 | 10 | 40 |
| Analogue 1 | 8.9 | 53 | 18 | 625 |

Example 3: Pharmacological Characterization of BAP-Modified γ-MSH Analogues

Test peptide analogues:

```
Analogue 1:
Ac-(Ac-Lys-Lys)Lys-Tyr-Val-Met-Gly-His-Phe-Arg-
DTrp-Asp-Arg-Phe-Gly-NH2

Analogue 2:
Ac-(Ac-Lys-Lys)Lys-Tyr-Val-Met-Gly-His-Phe-Arg-
Trp-Asp-Arg-Phe-Gly-NH2

Analogue 3:
Ac-(Ac-Lys-Lys)Lys -Tyr-Val-Met-Gly-His-DPhe-Arg-
DTrp-Asp-Arg-Phe-Gly-NH2

Analogue 4:
Ac-(Ac-Lys-Lys)Lys-Tyr-Val-Met-Gly-His-Phe-Arg-
DTrp-Asp-Arg-DPhe-Gly-NH2

Analogue 5:
Ac-(Ac-Lys-Lys)Lys-Tyr-Val-Nle-Gly-His-Phe-Arg-
DTrp-Asp-Arg-Phe-Gly-NH2

Analogue 6:
Ac-(Ac-Lys-Lys)Lys-Tyr-Val-Nle-Gly-His-Phe-Arg-
Trp-Asp-Arg-Phe-Gly-NH2

Analogue 7:
Ac-(Ac-Lys-Lys)Lys-Tyr-Val-Nle-Gly-His-DPhe-Arg-
Trp-Asp-Arg-Phe-Gly-NH2

Analogue 8:
Ac-(Ac-Lys-Lys)Lys-Tyr-Val-Nle-Gly-His-DPhe-Arg-
DTrp-Asp-Arg-Phe-Gly-NH2

Control peptides:
Control peptide 1 (γ2-MSH):
                                        (SEQ ID NO: 2)
Ac-Tyr-Val-Met-Gly-His-Phe-Arg-Trp-Asp-Arg-Phe-
Gly-NH2

Control peptide 2 (DTrp-γ2-MSH):
                                        (SEQ ID NO: 59)
Ac-Tyr-Val-Met-Gly-His-Phe-Arg-DTrp-Asp-Arg-Phe-
Gly-NH2
```

Results
Ki values (nM):

|  | MC1r | MC3r | MC4r | MC5r |
| --- | --- | --- | --- | --- |
| γ2MSH | 104 | 37 | 328 | 1022 |
| DTrp-γ2MSH | 28 | 34 | 173 | 369 |
| Analogue 1 | 3.8 | 15 | 150 | 215 |

MCr binding affinity relative to control peptide 1:

|  | MC1r | MC3r | MC4r | MC5r |
| --- | --- | --- | --- | --- |
| Analogue 1 | 27x | 5x | 2x | 5x |

MCr binding affinity relative to control peptide 2:

|  | MC1r | MC3r | MC4r | MC5r |
| --- | --- | --- | --- | --- |
| Analogue 1 | 4x | 2x | 2x | 3x |

MCr binding affinity relative to αMSH (Ac-Ser-Tyr-Ser-Met-Glu-His-Phe-Arg-Trp-Gly-Lys-Pro-Val-NH$_2$) (SEQ ID NO: 1):

|  | MC1r | MC3r | MC4r | MC5r |
| --- | --- | --- | --- | --- |
| Control peptide 1 | 0.04x | 1.5x | 0.1x | 0.4x |
| Control peptide 2 | 0.16x | 0.36x | 0.74x | 1.1x |
| Analogue 1 | 1.2x | 7.6x | 0.9x | 2x |
| Analogue 2 | 0.5x | 11.6x | 1.2x |  |
| Analogue 3 |  | 20x | 8.5x |  |
| Analogue 4 | 7.7x | 4.8x | 1.3x |  |
| Analogue 5 | 1.9x | 38x | 2.8x |  |
| Analogue 6 |  | 4.6x | 2.9x |  |
| Analogue 7 |  | 46x | 37x |  |
| Analogue 8 | 7.3x | 37x | 10.7x |  |

$EC_{50}$ values (nM):

|  | MC1r | MC3r | MC4r | MC5r |
| --- | --- | --- | --- | --- |
| Control peptide 1 | 141 | 46 | 279 | 1787 |
| Control peptide 2 | 167 | 170 | 56 | 505 |
| Analogue 1 | 68 | 2.0 | 252 | 555 |

Example 4: Synthesis of BAP Modified Peptides

Similarly the synthesis of BAP modified α-MSH peptide analogues (Example 1) peptides were synthesized using standard Fmoc chemistry using 1-[Bis(dimethylamino)methylene]-1H-1,2,3-triazolo[4,5-b]pyridinium 3-oxid hexafluorophosphate (HATU) or 2-(6-Chloro-1H-benzotriazole-1-yl)-1,1,3,3-tetramethylaminium hexafluorophosphate (HCTU) as the coupling reagents with Hunig's Base (N,N-diisopropylethylamine, DIPEA). For the lysine branching as described in more detail below, combination of orthogonally protected lysines were used including Fmoc-Lys(MTT)-OH, Fmoc-Lys(ivDde)-OH, and Fmoc-Lys(Boc)-OH.

Peptides were cleaved with standard cleavage cocktails including trifluoroacetic acid, triisopropoylsilane, and water and precipitated with ice-cold ether. All crude peptides were purified by reversed-phase chromatography on columns with C-18 functionality and using gradients of acetonitrile, deionized water, and trifluoroacetic acid as running buffers. Purity was determined by high-pressure liquid chromatography and mass (MS) and sequence (tandem MS) information was obtained using a nanospray mass spectrometer.

BAP Attached in the C-Terminus of the Sequence

Branching on the C-terminal lysine (METHOD 1): N-α-Fmoc-N-ε-4-methyltrityl-L-lysine was added to Rink amide resin after piperidine deprotection. The remaining sequence of the target peptide was added and the full length sequence was acetylated with acetic anhydride. The methyltrityl group was then removed using 1% trifluoroacetic acid in dichloromethane. Additional Nα-Fmoc-Nε-Boc-L-lysine was then added to the side chain and acetylated when desired.

Branching on other than the C-terminal lysine: analogously to attaching BAP to lysines in the sequence between the N- and C-termini (METHOD 2).

BAP Attached to Lysines in the Sequence Between the N- and C-Termini

METHOD 2: N-α-Fmoc-N-ε-4-methyltrityl-L-lysine was added to the peptide sequence, methytrityl was removed after finalizing the sequence and optionally N-terminal acetylation. Appropriate lysine analogues such as Fmoc-Lys(MTT)-OH, Fmoc-Lys(ivDde)-OH and Fmoc-Lys(Boc)-OH were sequentially added and selectively deprotected, before acetylation to ensure appropriate side chain and acetyl addition.

BAP Attached in the N-Terminus of the Sequence

Branching on the N-terminal lysine (METHOD 3): N-α-Fmoc-N-ε-4-methyltrityl-L-lysine was added to N-terminal of the sequence, Fmoc was removed, the sequence acetylated at the N-terminus, and the metyltrityl group was removed. Additional Na-Fmoc-Nc-Boc-L-lysine was then added to the side chain and acetylated when desired.

Branching on other than the N-terminal lysine: analogously to attaching BAP to lysines in the sequence between the N- and C-termini (METHOD 2).

Peptides

```
Analogue 1 (by METHOD 1):
Ac-His-Ala-Glu-Gly-Thr-Phe-Thr-Ser-Asp-Val-Ser-

Ser-Tyr-Leu-Glu-Gly-Gln-Ala-Ala-Lys-Glu-Phe-Ile-

Ala-Trp-Leu-Val-Lys-Gly-Arg-Gly-(Lys-Lys-Ac)Lys-

NH2

Purity: 99.1%

MS: 546.9, 637.8, 765.2

Analogue 2 (by METHOD 1):
Ac-His-Gly-Glu-Gly-Thr-Phe-Thr-Ser-Asp-Val-Ser-

Ser-Tyr-Leu-Glu-Gly-Gln-Ala-Ala-Lys-Glu-Phe-Ile-

Ala-Trp-Leu-Val-Lys-Gly-Arg-Gly-(Lys-Lys-Ac)Lys-

NH2

Purity: 99.3%

MS: 635.5, 762.4, 952.7
```

```
-continued
Analogue 3 (by METHOD 1):
Ac-His-Ala-Asp-Gly-Ser-Phe-Ser-Asp-Glu-Met-Asn- Thr-Ile-Leu-Asp-Asn-Leu-Ala-Ala-Arg-Asp-Phe-Ile- Asn-Trp-Leu-Ile-Gln-Thr-Lys-Ile-Thr-Asp-(Lys-Lys- Ac)Lys-NH2

Purity: 96.2%

MS: 605.5, 706.2, 847.2, 1058.8

Analogue 4 (by METHOD 1):
Ac-His-Gly-Asp-Gly-Ser-Phe-Ser-Asp-Glu-Met-Asn-

Thr-Ile-Leu-Asp-Asn-Leu-Ala-Ala-Arg-Asp-Phe-Ile-

Asn-Trp-Leu-Ile-Gln-Thr-Lys-Ile-Thr-Asp-(Lys-Lys-

Ac)Lys-NH2

Purity: 95.1%

MS: 603.5, 703.9, 844.4, 1055.3

Analogue 5 (by METHOD 1):
Ac-His-(D-Ala)-Asp-Gly-Ser-Phe-Ser-Asp-Glu-Met-

Asn-Thr-Ile-Leu-Asp-Asn-Leu-Ala-Ala-Arg-Asp-Phe-

Ile-Asn-Trp-Leu-Ile-Gln-Thr-Lys-Ile-Thr-Asp-(Lys-

Lys-Ac)Lys-NH2

Purity: 96.9%

MS: 706.2, 847.2, 1058.8

Analogue 6 (by METHOD 1):
Ac-Ala-Met-Val-Ser-Glu-Phe-Leu-Lys-Gln-(D-Ala)-

Trp-Phe-Ile-Glu-Asn-Glu-Glu-Gln-Glu-Tyr-Val-Gln-

Thr-Val-Lys-Lys-(Lys-Ac)Lys-NH2

Purity: 96.0

MS: 879.2

Analogue 7 (by METHOD 2):
Ac-Ala-Met-Val-Ser-Glu-Phe-Leu-(Ac-(Lys-Ac)Lys-

Lys)Lys-Gln-Ala-Trp-NH2

Purity: 97.3

MS: 442.2, 662.9
```

Example 5: Pharmacological characterization of BAP- modified GLP-1 analogues

Method:

CHO-K1 cells expressing the human GLP-1 receptor grown in media without antibiotic were detached by gentle flushing with PBS-EDTA (5 mM EDTA), recovered by centrifugation and resuspended in assay buffer (KRH: 5 mM KCl, 1.25 mM MgSO4, 124 mM NaCl, 25 mM HEPES, 13.3 mM Glucose, 1.25 mM KH2PO4, 1.45 mM CaCl2, 0.5 g/l BSA).

12 μl of cells were mixed with 12 μl of the test compound (solubilized in PBS/0.5% BSA and finally diluted from a stock solution of 1 mM) at increasing concentrations in 96 wells plates and then incubated 30 min at room temperature. cAMP production was determined after addition of a lysis buffer and 1 hour incubation, by use of competitive immunoassay using cryptate-labeled anti-cAMP and d2-labeled cAMP (HTRF kit from CisBio) with Delta F percentage values calculated according to the manufacturer specification. Dose response curves were performed in parallel with test compounds, and reference compounds.

The HTRF technology is a titration assay based on a competition between labeled cAMP (exogenous) and cAMP produced by the cell after activation of the MCr. The dynamic range of the assay was 3-4 fold meaning that the linear range (which enables conversion from raw data to nM of cAMP) is within that range. The window between top and bottom of the curve is higher (around 100) which means that converting into nM of cAMP, the assay window of cAMP goes from 1 nM (basal) to around 30 nM ($E_{max}$). All experiments were conducted in the presence of the non-selective phosphodiesterase inhibitor IBMX (1 mM in final concentration).

The test compounds were tested in a concentration range from $10^{-14}$ to $10^{-7}$ M Data is presented as mean values. The $EC_{50}$ (ie the concentration induced 50% of max response) and the hill slope were determined by best fit analyses after logarithmic transformation using the graph pad software (version 6.0).

Control peptide:

GLP-1 (7-36):
(SEQ ID NO: 112)
H-His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly-OH

Results:

|  | GLP-1 (7-36) | Analogue 1 | Analogue 2 |
|---|---|---|---|
| Max efficacy in % of control peptide |  | 101.3 | 102.4 |
| $EC_{50}$ (nM) | 0.016 | 0.016 | 0.040 |
| Hill Slope | 1.28 | 0.73 | 0.80 |

Both analogue 1 and 2 showed full agonist activity when compared to the control peptide GLP-1 (7-36) with sub-nano molar $EC_{50}$ values comparable to the control peptide GLP-1 (7-37). The lower Hill Slope indicates that agonist activity can be obtained at lower concentrations than what would be seen with the control peptide.

Example 6: Pharmacological characterization of BAP- modified GLP-2 analogues Method:

CHO-K1 cells expressing the human GLP-2 receptor grown in media without antibiotic were detached by gentle flushing with PBS-EDTA (5 mM EDTA), recovered by centrifugation and resuspended in assay buffer (KRH: 5 mM KCl, 1.25 mM MgSO4, 124 mM NaCl, 25 mM HEPES, 13.3 mM Glucose, 1.25 mM KH$_2$PO$_4$, 1.45 mM CaCl$_2$), 0.5 g/l BSA).

12 µl of cells were mixed with 12 µl of the test compound (solubilized in PBS/0.5% BSA and finally diluted from a stock solution of 1 mM) at increasing concentrations in 96 wells plates and then incubated 30 min at room temperature. cAMP production was determined after addition of a lysis buffer and 1 hour incubation, by use of competitive immunoassay using cryptate-labeled anti-cAMP and d2-labeled cAMP (HTRF kit from CisBio) with Delta F percentage values calculated according to the manufacturer specification. Dose response curves were performed in parallel with test compounds, and reference compounds.

The HTRF technology is a titration assay based on a competition between labeled cAMP (exogenous) and cAMP produced by the cell after activation of the MCr. The dynamic range of the assay was 3-4 fold meaning that the linear range (which enables conversion from raw data to nM of cAMP) is within that range. The window between top and bottom of the curve is higher (around 100) which means that converting into nM of cAMP, the assay window of cAMP goes from 1 nM (basal) to around 30 nM ($E_{max}$). All experiments were conducted in the presence of the non-selective phosphodiesterase inhibitor IBMX (1 mM in final concentration).

The test compounds were tested in a concentration range from $10^{14}$ to $10^{-7}$M Data is presented as mean values. The $EC_{50}$ (ie the concentration induced 50% of max response) and the Hill slope were determined by best fit analyses after logarithmic transformation using the graph pad software (version 6.0).

Control peptide:

GLP-2 (1-34):
(SEQ ID NO: 113)
H-His-Ala-Asp-Gly-Ser-Phe-Ser-Asp-Glu-Met-Asn-Thr-Ile-Leu-Asp-Asn-Leu-Ala-Ala-Arg-Asp-Phe-Ile-Asn-Trp-Leu-Ile-Gln-Thr-Lys-Ile-Thr-Asp-Arg-OH

Results:

|  | GLP-2 (1-34) | Analogue 3 | Analogue 4 | Analogue 5 |
|---|---|---|---|---|
| Max efficacy in % of control peptide |  | 101.3 | 101.5 | 95.1 |
| $EC_{50}$ (nM) | 0.36 | 3.4 | 5.9 | 8.9 |
| Hill Slope | 0.78 | 0.97 | 0.96 | 1.03 |

All three analogues showed full agonist activity when compared to the control peptide GLP-2 (1-34) with $EC_{50}$ values in the nM range. Consequently the current examples of BAP modified GLP-2 analogues are full and potent agonists against the human GLP-2 receptor.

Example 7: Pharmacological Characterization of BAP- Modified AnxA1 N-Terminal Fragments Method:

Recombinant cells co-expressing mitochondrial apoaequirin and recombinant human type 2 Formyl peptide receptor (FPR2) were grown for 18 hours prior to testing in media without antibiotics were detached by gentle flushing with PBS-EDTA (5 mM EDTA), recovered by centrifugation and re-suspended in assay buffer (DHEM/HAM's F12 with HEPES and 0.1% protease free BSA). Cells were then incubated for at least 4 hours at room temperature coelenterazine h (from Molecular Probes) before DR studies were conducted.

50 μl of cell suspension was injected on 50 μl of the test or control compound (solubilized in PBS/0.5% BSA and finally diluted from a stock solution of 1 mM) at increasing concentrations in 96 wells plates and then incubated 30 min at room temperature. The resulting light emission was recorded using the Hamamatsu functional drug Screening system 6000 (FDSS6000). For standardization of emission of recoded light across plates and between experiments 100 μM digitonin or 20 μM ATP were added to some of the wells.

Agonist activity was expressed as % of the maximal activity obtained with the internal control compound Trp-Lys-Tyr-Met-Val-Met (SEQ ID NO: 114)

The test compounds were tested in a concentration range from $10^{-11}$ to $10^{-5}$M Data is presented as mean values. When possible the $EC_{50}$ (ie the concentration induced 50% of max response) was determined by best fit analyses after logarithmic transformation using the graph pad software (version 6.0).

```
Control peptide 1:
AnxA1 (2-26):
                                               (SEQ ID NO: 115)
Ac-Ala-Met-Val-Ser-Glu-Phe-Leu-Lys-Gln-Ala-Trp-
Phe-Ile-Glu-Asn-Glu-Glu-Gln-Glu-Tyr-Val-Gln-Thr-
Val-Lys-OH Control peptide 2:
AnxA1 (2-12):
                                               (SEQ ID NO: 116)
Ac-Ala-Met-Val-Ser-Glu-Phe-Leu-Lys-Gln-Ala-Trp-NH2
```

Results:

In the literature both the AnxA1 (2-12) and the AnxA1 (2-26)N-terminal fragments of the AnxA1 protein are described as agonist to the FPR2 receptor- none of them as significantly potent, but the in the setting neither control peptide 1 or 2 were able to induce agonist activity in the applied concentration range. In contrast to this both analogue 6 and analogue 7 showed agonist activity. For Analogue 6 the agonist activity reached 33% of the max response seen with the internal control compound Trp-Lys-Tyr-Met-Val-Met (SEQ ID NO: 114). The corresponding maximal activity of control compound 1 was less than 1%. For analogue 7, $EC_{50}$ was determined to 1.56 μM. The maximal agonist response obtained at the highest tested dose was 85% of the max response obtained with the Trp-Lys-Tyr-Met-Val-Met (SEQ ID NO: 114) hexapeptide, whereas the maximal activity of control peptide was less than 1%.

---

What is claimed is:

1. A peptide analogue comprising a peptide and one or more branched amino acid probes,
   wherein said peptide is selected from the group consisting of glucagon-like peptide-1 (GLP-1), GLP-1 (7-37), GLP-1 (7-33) and exendin-4,
   wherein said one or more branched amino acid probes comprises a first amino-alkyl amino acid residue,
   said first amino-alkyl amino acid residue optionally being covalently linked to a second amino-alkyl amino acid residue, or to a second and a third amino-alkyl amino acid residue, to form a linear chain of 2 or 3 amino-alkyl amino acid residues,
   wherein the side chain of one or more of said first, second and/or third amino-alkyl amino acid residues are each modified by attaching to the side chain amino group a molecule independently selected from the group consisting of $AAA_q$-AAA (SEQ ID NO: 168); $(aa_3)_p$-$AAA_q$ (SEQ ID NOs: 169-174); $AAA_q$-$(aa_3)_p$ (SEQ ID NOs: 175-180); $[(aa_3)$-AAA$]_p$ (SEQ ID NOs: 181 and 182); and $[AAA$-$(aa_3)]_p$ (SEQ ID NOs: 183 and 184);
   wherein q is a number selected from 0, 1, 2 and 3; p is a number selected from 1, 2 and 3; AAA is an amino-alkyl amino acid residue; and $(aa_3)$ is an amino acid residue independently selected from Arg, His, Gly and Ala,
   wherein said amino-alkyl amino acid residues are optionally acetylated,
   wherein said first amino-alkyl amino acid residue is covalently linked to the N-terminus of said peptide, covalently linked to the C-terminus of said peptide, or attached to the side chain amino group of an amino-alkyl amino acid residue within said peptide,
   with the proviso that said one or more branched amino acid probes consists of 2 to 9 amino acid residues.

2. The peptide analogue according to claim 1, wherein the one or more branched amino acid probes comprises a first amino-alkyl amino acid residue, said first amino-alkyl amino acid residue being optionally acetylated,
   wherein the side chain amino group of said first amino-alkyl amino acid residue is modified by attaching a molecule independently selected from the group consisting of $AAA_T$-AAA (SEQ ID NO: 168); $(aa_3)_p$-$AAA_q$ (SEQ ID NOs: 169-174); $AAA_q$-$(aa_3)_p$ (SEQ ID NOs: 175-180); $[(aa_3)$-AAA$]_p$ (SEQ ID NOs: 181 and 182); and $[AAA$-$(aa_3)]_p$ (SEQ ID NOs: 183 and 184);
   wherein q is a number selected from 0, 1, 2 and 3; p is a number selected from 1, 2 and 3; AAA is an amino-alkyl amino acid residue which is optionally acetylated; and $(aa_3)$ is an amino acid residue independently selected from Arg, His, Gly and Ala.

3. The peptide analogue according to claim 1, wherein the one or more branched amino acid probes comprises a first amino-alkyl amino acid residue covalently linked to a second amino-alkyl amino acid residue, to form a linear chain of 2 amino-alkyl amino acid residues,
   said first and/or second amino-alkyl amino acid residues optionally acetylated,
   wherein the side chain amino group of said first and/or said second amino-alkyl amino acid residue is modified by attaching a molecule independently selected from the group consisting of $AAA_q$-AAA (SEQ ID NO: 168); $(aa_3)_p$-$AAA_q$ (SEQ ID NOs: 169-174); $AAA_T$-$(aa_3)_p$ (SEQ ID NOs: 175-180); $[(aa_3)$-AAA]p (SEQ ID NOs: 181 and 182); and $[AAA$-$(aa_3)]_p$ (SEQ ID NOs: 183 and 184); wherein q is a number selected from 0, 1, 2 and 3; p is a number selected from 1, 2 and 3; AAA is an amino-alkyl amino acid residue which is optionally acetylated; and $(aa_3)$ is an amino acid residue independently selected from Arg, His, Gly and Ala.

4. The peptide analogue according to claim 1, wherein said amino-alkyl amino acid residues are individually selected from the group consisting of L-lysine, D-lysine, L-ornithine and D-ornithine.

5. The peptide analogue according to claim 1, wherein each of the first, second and/or third amino-alkyl amino acids of the one or more_branched amino acid probes are individually selected from the group consisting of L-lysine, D-lysine, L-ornithine and D-ornithine.

6. The peptide analogue according to claim 1, wherein each AAA of the molecules $AAA_q$-AAA (SEQ ID NO: 185); $(aa_3)_p$-$AAA_q$ (SEQ ID NOs: 186-191); $AAA_q$-$(aa_3)_p$ (SEQ ID NOs: 192-197); $[(aa_3)$-AAA$]_p$ (SEQ ID NOs: 198 and 199); and $[AAA$-$(aa_3)]p$ (SEQ ID NOs; 200-201) are individually selected from the group consisting of L-lysine, D-lysine, L-ornithine and D-ornithine.

7. The peptide analogue according to claim 1, wherein the molecule to be attached to said side chain amino group is independently selected from the group consisting of $Lys_q$-Lys (SEQ ID NO: 117); $(aa_3)_p$-$Lys_q$ (SEQ ID NOs: 119-124); $Lys_q$-$(aa_3)_p$ (SEQ ID NOs: 125-130); $[(aa_3)$-Lys$]_p$ (SEQ ID NOs: 131 and 132); $[Lys$-$(aa_3)]_p$ (SEQ ID NOs: 133 and 134); $Orn_q$-Orn (SEQ ID NO: 135); $(aa_3)_p$-$Orn_q$ (SEQ ID NOs: 136-141); $Orn_q$-$(aa_3)_p$ (SEQ ID NOs: 142-147); $[(aa_3)$-Orn]p (SEQ ID NOs: 148 and 149); $[Orn$-$(aa_3)]_p$ (SEQ ID NOs: 150 and 151); $Orn_p$-$Lys_q$ (SEQ ID NOs: 152-157); $Lys_p$-$Orn_p$ (SEQ ID NOs: 158-163); $[Orn$-$Lys]_p$ (SEQ ID NOs: 164 and 165); and $[Lys$-$Orn]_p$ (SEQ ID NOs: 166 and 167), wherein q is a number selected from 0, 1, 2 and 3; p is a number selected from 1, 2 and 3; $(aa_3)$ is an amino acid residue independently selected from Arg, His, Gly and Ala; and each of said Lys, Orn and $(aa)_3$ amino acid residues are optionally acetylated.

8. The peptide analogue according to claim 1, wherein the molecule to be attached to said side chain amino group is independently selected from the group consisting of $Lys_q$-Lys (SEQ ID NO: 117); $(aa_3)_p$-$Lys_q$ (SEQ ID NOs: 119-124); $Lys_q$-$(aa_3)_p$ (SEQ ID NOs: 125-130); $[(aa_3)$-Lys]p (SEQ ID NOs: 131 and 132); and $[Lys$-$(aa_3)]_p$ (SEQ ID NOs: 133 and 134); and each of said Lys residues are optionally acetylated.

9. The peptide analogue according to claim 1, wherein each amino-alkyl amino acid residue is individually selected from the group consisting of L-lysine and D-lysine.

10. The peptide analogue according to claim 1, wherein the molecule to be attached to said side chain amino group is $Lys_q$-Lys; wherein q is a number selected from 0, 1, 2 and 3 and each of said Lys residues are optionally acetylated.

11. The peptide analogue according to claim 1, wherein the molecule to be attached to said side chain amino group is independently selected from the group consisting of Ac-$AAA_q$-AAA (SEQ ID NO: 168); Ac-$(aa_3)_p$-$AAA_q$ (SEQ ID NOs: 169-174); Ac-$AAA_q$-$(aa_3)_p$ (SEQ ID NOs: 175-180); Ac-$[(aa_3)$-AAA$]_p$ (SEQ ID NOs: 181 and 182); Ac-$[AAA$-$(aa_3)]p$ (SEQ ID NOs: 183 and 184); Ac-$Lys_q$-Lys (SEQ ID NO: 118); Ac-$(aa_3)_p$-$Lys_q$ (SEQ ID NOs: 119-124); Ac-$Lys_q$-$(aa_3)_p$ (SEQ ID NOs: 125-130); Ac-$[(aa_3)$-Lys$]_p$ (SEQ ID NOs: 131 and 132); Ac-$[Lys$-$(aa_3)]_p$ (SEQ ID NOs: 133 and 134); Ac-$Orn_q$-Orn (SEQ ID NO: 135); Ac-$(aa_3)_p$-$Orn_q$ (SEQ ID NOs: 136-141); Ac-$Orn_q$-$(aa_3)_p$ (SEQ ID NOs: 142-147); Ac-$[(aa_3)$-Orn]p (SEQ ID NOs: 148 and 149); Ac-$[Orn$-$(aa_3)]_p$ (SEQ ID NOs: 150 and 151); Ac-$Orn_p$-$Lys_p$ (SEQ ID NOs: 152-157); Ac-$Lys_p$-$Orn_p$ (SEQ ID NOs: 158-163); Ac-$[Orn$-$Lys]_p$ (SEQ ID NOs: 164 and 165);

and Ac-[Lys-Orn]$_p$ (SEQ ID NOs: 166 and 167), wherein q is a number selected from 0, 1, 2 and 3; p is a number selected from 1, 2 and 3; and (aa$_3$) is an amino acid residue independently selected from Arg, His, Gly and Ala.

12. The peptide analogue according to claim 1, wherein the molecule to be attached to the side chain amino group of one or more of the first, second and/or third amino-alkyl amino acid residues is selected from the group consisting of AAA, Ac-AAA, AAA-AAA, Ac-AAA-AAA, AAA-AAA-AAA, Ac-AAA-AAA-AAA, AAA-AAA-AAA-AAA (SEQ ID NO: 168), Ac-AAA-AAA-AAA-AAA (SEQ ID NO: 168), AAA-Gly-AAA, Ac-AAA-Gly-AAA, AAA-AAA-Gly, Ac-AAA-AAA-Gly, AAA-Gly, Ac-AAA-Gly, AAA-Ala-AAA, Ac-AAA-Ala-AAA, AAA-AAA-Ala, Ac-AAA-AAA-Ala, AAA-Ala, Ac-AAA-Ala, AAA-His-AAA, Ac-AAA-His-AAA, AAA-AAA-His, Ac-AAA-AAA-His, AAA-His, Ac-AAA-His, AAA-Arg-AAA, Ac-AAA-Arg-AAA, AAA-AAA-Arg, Ac-AAA-AAA-Arg, AAA-Arg and Ac-AAA-Arg; wherein AAA is an amino-alkyl amino acid residue, optionally acetylated.

13. The peptide analogue according to claim 1, wherein the molecule to be attached to the side chain amino group of one or more of the first, second and/or third amino-alkyl amino acid residues is selected from the group consisting of Lys, Ac-Lys, Lys-Lys, Ac-Lys-Lys, Lys-Lys-Lys, Ac-Lys-Lys-Lys, Lys-Lys-Lys-Lys (SEQ ID NO: 117), Ac-Lys-Lys-Lys-Lys (SEQ ID NO: 118), Lys-Gly-Lys, Ac-Lys-Gly-Lys, Lys-Lys-Gly, Ac-Lys-Lys-Gly, Lys-Gly, Ac-Lys-Gly, Lys-Ala-Lys, Ac-Lys-Ala-Lys, Lys-Lys-Ala, Ac-Lys-Lys-Ala, Lys-Ala, Ac-Lys-Ala, Lys-His-Lys, Ac-Lys-His-Lys, Lys-Lys-His, Ac-Lys-Lys-His, Lys-His, Ac-Lys-His, Lys-Arg-Lys, Ac-Lys-Arg-Lys, Lys-Lys-Arg, Ac-Lys-Lys-Arg, Lys-Arg and Ac-Lys-Arg.

14. The peptide analogue according to claim 1, wherein the one or more branched amino acid probes are selected from the group consisting of Ac-(Ac-Lys)Lys-Lys-; (Ac-Lys)Lys-Lys-; Ac-(Lys)Lys-Lys-; (Lys)Lys-Lys-; Ac-Lys-(Ac-Lys)Lys-; Lys-(Ac-Lys)Lys-; Ac-Lys-(Lys)Lys-; Lys-(Lys)Lys-; Ac-(Ac-Lys-Lys)-Lys-; (Ac-Lys-Lys)-Lys-; Ac-(Lys-Lys)-Lys-; and (Lys-Lys)-Lys-.

15. The peptide analogue according to claim 1, wherein the one or more branched amino acid probes are selected from the group consisting of Ac-(Ac-Lys)Lys-, Ac-(Lys)Lys- and (Lys)Lys-.

16. The peptide analogue according to claim 1, wherein said first amino-alkyl amino acid residue is attached to the ε-amino group of a lysine residue within said peptide.

17. A method for treatment of ischemia, inflammation, and/or a metabolic condition, said method comprising administering an effective amount of a peptide analogue according to claim 1 to an individual in need thereof, wherein said treatment is prophylactic or ameliorative.

18. The method for treatment according to claim 17, wherein the metabolic condition is selected from diabetes mellitus, prediabetic conditions, glucose intolerance, obesity, overweight, metabolic syndrome, gestational diabetes mellitus and metabolic disease associated with polycystic ovarian syndrome.

* * * * *

UNITED STATES PATENT AND TRADEMARK OFFICE
CERTIFICATE OF CORRECTION

PATENT NO. : 11,141,455 B2
APPLICATION NO. : 15/917223
DATED : October 12, 2021
INVENTOR(S) : Thomas Boesen It is certified that error appears in the above-identified patent and that said Letters Patent is hereby corrected as shown below:

In the Claims

Column 155, Claim 2, Line 43: "$AAA_T AAA$" should read --$AAA_q$-AAA--

Signed and Sealed this
Seventeenth Day of October, 2023

Katherine Kelly Vidal
*Director of the United States Patent and Trademark Office*